(12) United States Patent
Gant et al.

(10) Patent No.: US 10,421,710 B2
(45) Date of Patent: Sep. 24, 2019

(54) SUBSTITUTED PHENETHYLAMINES WITH SEROTONINERGIC AND/OR NOREPINEPHRINERGIC ACTIVITY

(71) Applicant: Auspex Pharmaceuticals, Inc., La Jolla, CA (US)

(72) Inventors: Thomas G. Gant, La Jolla, CA (US); Sepehr Sarshar, La Jolla, CA (US); Soon Hyung Woo, La Jolla, CA (US)

(73) Assignee: AUSPEX PHARMACEUTICALS, INC., Vista, CA (US)

( * ) Notice: Subject to any disclaimer, the term of this patent is extended or adjusted under 35 U.S.C. 154(b) by 0 days.

(21) Appl. No.: 14/559,520

(22) Filed: Dec. 3, 2014

(65) Prior Publication Data

US 2015/0152042 A1 Jun. 4, 2015

Related U.S. Application Data

(63) Continuation of application No. 12/048,012, filed on Mar. 13, 2008, now abandoned.
(Continued)

(51) Int. Cl.
*C07C 211/64* (2006.01)
*C07B 59/00* (2006.01)
(Continued)

(52) U.S. Cl.
CPC ............ *C07C 211/64* (2013.01); *C07B 59/00* (2013.01); *C07C 215/64* (2013.01);
(Continued)

(58) Field of Classification Search
None
See application file for complete search history.

(56) References Cited

U.S. PATENT DOCUMENTS

| 4,535,186 A | 8/1985 | Husbands |
|---|---|---|
| 5,916,923 A | 6/1999 | Rudolph |

(Continued)

FOREIGN PATENT DOCUMENTS

| EP | 0112669 A2 | 7/1984 |
|---|---|---|
| EP | 0654264 B1 | 5/2001 |

(Continued)

OTHER PUBLICATIONS

Gant, Thomas G. Prosecution History for U.S. Appl. No. 12/234,236, Substituted Phenethylamines With Serotoninergic and/or Norepinephrinergic Activity.
(Continued)

*Primary Examiner* — Clinton A Brooks
(74) *Attorney, Agent, or Firm* — BakerHostetler

(57) ABSTRACT

Chemical syntheses and medical uses of novel inhibitors of the uptake of monoamine neurotransmitters and pharmaceutically acceptable salts and prodrugs thereof, for the treatment and/or management of psychotropic disorders, anxiety disorder, generalized anxiety disorder, depression, post-traumatic stress disorder, obsessive-compulsive disorder, panic disorder, hot flashes, senile dementia, migraine, hepatopulmonary syndrome, chronic pain, nociceptive pain, neuropathic pain, painful diabetic retinopathy, bipolar depression, obstructive sleep apnea, psychiatric disorders, premenstrual dysphoric disorder, social phobia, social anxiety disorder, urinary incontinence, anorexia, bulimia nervosa, obesity, ischemia, head injury, calcium overload in brain cells, drug dependence, attention deficit hyperactivity disorder, fibromyalgia, irritable bowel syndrome, and/or premature ejaculation are described.

(Continued)

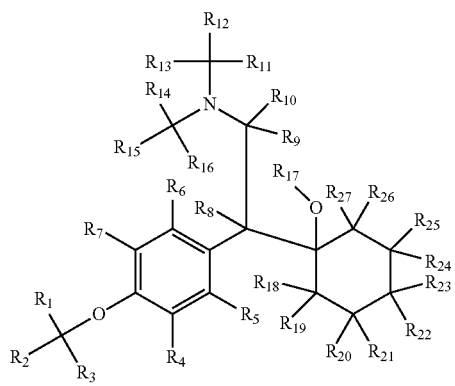

Formula I

20 Claims, 15 Drawing Sheets

Related U.S. Application Data

(60) Provisional application No. 60/895,049, filed on Mar. 15, 2007, provisional application No. 60/944,399, filed on Jun. 15, 2007.

(51) Int. Cl.
    *C07C 215/64*     (2006.01)
    *C07C 217/74*     (2006.01)
    *C07D 265/16*     (2006.01)

(52) U.S. Cl.
    CPC .......... *C07C 217/74* (2013.01); *C07D 265/16* (2013.01); *C07B 2200/05* (2013.01); *C07B 2200/07* (2013.01); *C07B 2200/13* (2013.01); *C07C 2601/14* (2017.05)

(56) References Cited

U.S. PATENT DOCUMENTS

| | | | |
|---|---|---|---|
| 6,071,918 A | 6/2000 | Cook | |
| 6,221,335 B1 | 4/2001 | Foster | |
| 6,274,171 B1 | 8/2001 | Sherman | |
| 6,310,101 B1 | 10/2001 | Rudolph | |
| 6,395,788 B1 | 5/2002 | Iglehart | |
| 6,403,120 B1 | 6/2002 | Sherman | |
| 6,419,958 B2 | 7/2002 | Sherman | |
| 6,440,457 B1 | 8/2002 | Edgren | |
| 6,444,708 B2 | 9/2002 | Rudolph | |
| 6,579,899 B1 | 6/2003 | Wurtman | |
| 6,541,523 B2 | 8/2003 | Iglehart | |
| 6,603,008 B1 | 8/2003 | Ando et al. | |
| 6,673,838 B2 | 1/2004 | Hadfield | |
| 6,924,393 B2 * | 8/2005 | Dolitzky ............... | C07C 213/10 564/336 |
| 7,291,347 B2 | 11/2007 | Hadfield | |
| 7,456,317 B2 * | 11/2008 | Gant ..................... | C07C 217/74 564/305 |
| 7,517,990 B2 | 4/2009 | Ito et al. | |
| 2001/0046988 A1 | 11/2001 | Iglehart | |
| 2002/0013372 A1 | 1/2002 | Ekins | |
| 2002/0094995 A1 | 7/2002 | Foster | |
| 2003/0215507 A1 | 11/2003 | Sherman | |
| 2004/0029869 A1 | 2/2004 | Iglehart | |
| 2005/0054942 A1 | 3/2005 | Melker | |
| 2005/0118264 A1 | 6/2005 | Sela | |
| 2005/0181071 A1 | 8/2005 | Binder | |
| 2005/0233459 A1 | 10/2005 | Melker | |
| 2005/0261278 A1 | 11/2005 | Weiner | |
| 2007/0149622 A1 | 6/2007 | Gant | |
| 2007/0197695 A1 | 8/2007 | Potyen et al. | |
| 2008/0033011 A1 | 2/2008 | Tung | |
| 2008/0280991 A1 | 11/2008 | Gant | |
| 2008/0287774 A1 | 11/2008 | Katz-Brull | |
| 2009/0018207 A1 | 1/2009 | Gant | |
| 2009/0023765 A1 | 1/2009 | Gant | |
| 2009/0028873 A1 | 1/2009 | Gant | |
| 2009/0069431 A1 | 3/2009 | Czarnik | |
| 2009/0076162 A1 | 3/2009 | Czarnik | |
| 2009/0312435 A1 | 12/2009 | Gant | |
| 2010/0007087 A1 | 3/2010 | Gant | |

FOREIGN PATENT DOCUMENTS

| | | |
|---|---|---|
| EP | 1202722 B1 | 7/2005 |
| WO | WO 1995/26325 A2 | 10/1995 |
| WO | WO 2001/12175 A1 | 2/2001 |
| WO | WO 2001/54681 A2 | 8/2001 |
| WO | WO 2002/085297 A2 | 10/2002 |
| WO | WO 2005/058796 A2 | 6/2005 |
| WO | WO 2005/112927 A1 | 12/2005 |
| WO | WO 2006/034343 A2 | 3/2006 |
| WO | WO 2006/044916 A2 | 4/2006 |
| WO | WO 2007/016315 A2 | 2/2007 |
| WO | WO 2007/064697 A1 | 6/2007 |
| WO | WO 2008/140859 A1 | 11/2008 |
| WO | WO 2009/018169 A1 | 2/2009 |
| WO | WO 2010/028130 A2 | 3/2010 |
| WO | WO 2010/120797 A2 | 10/2010 |
| WO | WO 2010/120797 A3 | 10/2010 |

OTHER PUBLICATIONS

Gant, Thomas G., Response to Non-Final Office Action for U.S. Appl. No. 12/234,236, Substituted Phenethylamines With Serotoninergic and/or Norepinephrinergic Activity, Response filed in PTO on Apr. 12, 2010.
Gant, Thomas G., Prosecution History for U.S. Appl. No. 12/095,598, Substituted Phenethylamines With Serotoninergic and/or Norepinephrinergic Activity.
Gant, Thomas G., Prosecution History for U.S. Appl. No. 12/234,318, Substituted Phenethylamines With Serotoninergic and/or Norepinephrinergic Activity.
Yang, et al, Synthesis of 3-deuterated diazepam and nordiazepam 4-oxides and their use in the synthesis of other 3-deuterated derivatives, J. Label. Comp. Radiopharm., 38(8), 753-759, 1996.
Gant, Thomas G., U.S. Appl. No. 11/565,451—Prosecution History, Substituted Phenethylamines With Serotoninergic and/or Norepinephrinergic Activity.
Gant, Thomas G., PCT/US10/30913, Methods of Reduction of Interpatient Variability, publication pending.
Gant, Thomas G., U.S. Appl. No. 12/234,236—Prosecution History, Substituted Phenethylamines With Serotoninergic and/or Norepinephrinergic Activity.
Gant, Thomas G., U.S. Appl. No. 12/234,236—Response to non-final office action, Substituted Phenethylamines With Serotoninergic and/or Norepinephrinergic Activity, response filed in PTO on Jul. 29, 2010.
Browne et al., Pharmacokinetic Equivalence of Stable-Isotope-Labeled and Unlabeled Drugs. Phenobarbital in Man, J Clin Pharmacol, Jul. 1982, 22, 309-315.
Dent, Certificate of Analysis—O-Desmethylvenlafaxine D6; Bog Synthesis 2006.
Dent, Certificate of Analysis—Venlafaxine D6—HCl; Bog Synthesis 2006.
Lee et al., Deuterium Magic Angle Spinning Studies of Substrates Bound to Cytochrome P450, Biochemistry, Aug. 1999, 38, 10808-10813.
Basappa et al., Simple and an Efficient Method for the Synthesis of 1-[2-Dimethylamino-1-(4-Methoxyphenyl)-Ethyl]-Cyclohexanol Hydrochloride: (+/−) Venlafaxine Racemic Mixtures, Bioorganic & Medicinal Chemistry Letters (2004), 14(12), 3279-3281.

(56) References Cited

OTHER PUBLICATIONS

Burm et al., Pharmacokinetics of Lidocaine and Bupivacaine and Stable Isotope-Labeled Analogs: A Study in Healthy Volunteers, Biopharmaceutics and Drug Disposition, Jan.-Feb. 1988, 9, 85-95.

Kushner et al., Pharmacological Uses and Perspectives of Heavy Water and Deuterated Compounds, Canadian Journal of Physiology and Pharmacology, Feb. 1999, 77(2), 79-88.

Bauer et al., Influence of Long-Term Infusions on Lidocaine Kinetics, Clin. Pharmacol. Ther. 1982, 433-7.

Fisher et al., The Complexities Inherent in Attempts to Decrease Drug Clearance by Blocking Sites of Gyp-Mediated Metabolism, Curr Opin Drug Discov Develop, Jan. 2006, 9(1), 101-9.

Nelson et al., The Use of Deuterium Isotope Effect to Probe the Active Site Properties, Mechanism of Cytochrome P450-Catalyzed Reactions, and Mechanisms of Metabolically Dependent Toxicity, Drug Metabolism and Disposition, Dec. 2003, 31:1481-1498.

Mamada et al., Pharmacokinetic Equivalence of Deuterium-Labeled and Unlabeled Phenytoin, Drug Metabolism and Disposition, Jul.-Aug. 1986, 14(4), 509-11.

Pohl et al., Determination of Toxic Pathways of Metabolism by Deuterium Substitution, Drug Metabolism Reviews 1984-1985, 15(7), 1335-51.

Rampe et al. Deuterated Analogs of Verapamil and Nifedipine. Synthesis and Biological Activity, Eur J Med Chem, 1993, 28, 259-263.

Helfenbein et al., Isotopic Effect Study of Propofol Deuteration on the Metabolism, Activity, and Toxicity of the Anesthetic, J Med Chem, Dec. 2002, 45, 5806-5808.

Wen et al., Simultaneous Stereoselective Analysis of Venlafaxine and O-Desmethylvenlafaxine Enantiomers in Human Plasma by HPLC-ESL/MS Using a Vancomycin Chiral Column, J Chromatography B, May 2007, 850, 183-9.

Yardley et al., 2-Phenyl-2-(1-Hydroxycycloalkyl)Ethylamine Derivatives: Synthesis and Antidepressant Activity, J Med Chem, Oct. 1990, 33(10), 2899-905.

Nelson et al., Primary and B-Secondary Deuterium Isotope Effects in N-Deethylation Reactions, J Med Chem, Nov. 1975, 18(11), 1062-5.

Farmer et al., Synthesis, Metabolism, and Antitumor Activity of Deuterated Analogues of 1-(2-Choloroethyl)-3-Cyclohexyl-1-Nitrosourea, J Med Chem, Jun. 1978, 21(6), 514-20.

Borgstrom et al, Comparative Pharmacokinetics of Unlabeled and Deuterium-Labeled Terbutaline: Demonstration of a Small Isotope Effect, Pharm Sci, 1988, 77(11), 952-4.

Browne, Isotope Effect: Implications for Pharmaceutical Investigations, Stable Isotopes in Pharmaceutical Research, Pharmacochemistry Library (1997), 26, 13-18.

Lessard et al., Influence of Cyp2d6 Activity on the Disposition and Cardiovascular Toxicity of the Antidepressant Agent Venlafaxine in Humans, Pharmacogenetics, Aug. 1999, 9(4), 435-443.

Elison et al., Effect of Deuteration of N-CH3 Group on Potency and Enzymatic N-Demethylation of Morphine, Science, Oct. 1961, 134(3485), 1078-9.

Chavan et al., An Efficient and Green Protocol for the Preparation of Cycloalkanols: A Practical Synthesis of Venlafaxine, Tetrahedron Letters, 2004, 45(39), 7291-7295.

Morton et al., Venlafaxine: A Structurally Unique and Novel Antidepressant, The Annals of Pharmacotherapy, Apr. 1995, 29(4), 387-95.

Reis et al. Therapeutic Drug Monitoring of Racemic Venlafaxine and Its Main Metabolites in an Everyday Clinical Setting, Therapeutic Drug Monitoring, Aug. 2002, 24(4), 545-553.

Foster, Deuterium Isotope Effects in Studies of Drug Metabolism, Trends in Pharmacological Sciences, 1984, 5 (12), 524-7.

Gant, T. G. et. al.; Substituted Phenethylamines With Serotoninergic and/or Norepinephrinergic Activity; filed on May 30, 2008; not yet published; U.S. Appl. No. 12/095,598.

Deschamps, F.; Synthese Aptochem Catalog 2007-8.

Muth et al., Study of Deuterium Isotope Effects on Protein Binding by Gas Chromatography/ Mass Spectrometry. Caffeine and Deuterated Isomers, Drug Development Research, 1991, 23, 191-199.

Dyck et al, Effects of Deuterium Substitution on the Catabolism of Beta-Phenethylamine: An In Vivo Study, J Neurochem, Feb. 1986, 46(2), 399-404.

Tonn et al., Simultaneous Analysis of Diphenhydramine and a Stable Isotope Analog (2H10) Diphenhydramine Using Capillary Gas Chromatography With Mass Selective Detection in Biological Fluids From Chronically Instrumented Pregnant Ewes, Biomedical Mass Spectrometry, Nov. 1993, 22, 633-642.

Haskins, The Application of Stable Isotopes in Biomedical Research, Biomedical Mass Spectrometry, Jul. 1982, 9(7), 269-277.

Wolen et al., The Application of Stable Isotopes to Studies of Drug Bioavailability and Bioequivalence, J Clin Pharmacol., Jul.-Aug. 1986, 26, 419-424.

Browne, Thomas, Stable Isotope Techniques in Early Drug Development: An Economic Evaluation, J Clin Pharmacol, 1998, 38, 213-220.

Baillie, The Use of Stable Isotopes in Pharmaceutical Research, Pharmacological Reviews, 1981, 33(2), 81-132.

Gouyette, Use of Deuterium-Labelled Elliptinium and Its Use in Metabolic Studies, Biomedical and Environmental Mass Spectrometry, Mar. 1988, 15, 243-247.

Cherrah et al., Study of Deuterium Isotope Effects on Protein Binding by Gas Chromatography/Mass Spectrometry. Caffeine and Deuterated Isomers, Biomedical and Environmental Mass Spectrometry, Nov. 1987, 14, 653-657.

Pieiaszek et al., Moricizine Bioavailability Via Simultaneous, Dual, Stable Isotope Administration: Bioequivalence Implications, J Clin Pharmacol, Aug. 1999, 39, 817-825.

Honma et al., The Metabolism of Roxatidine Acetate Hydrochloride, Drug Metabolism and Disposition, Jul.-Aug. 1987, 15(4), 551-559.

Kupka et al. "MS01-T03, Deuterium Disturbs the Molecular Arrangement in the Solid State", General Interest, p. 5, May 2015.

\* cited by examiner

SUBSTITUTED PHENETHYLAMINES WITH SEROTONINERGIC AND/OR NOREPHRINERGIC ACTIVITY

This application is a continuation of U.S. application Ser. No. 12/048,012 filed Mar. 13, 2008, which claims the benefit of priority of U.S. provisional application No. 60/895,049, filed Mar. 15, 2007, and No. 60/944,399, filed Jun. 15, 2007, the disclosures of which are hereby incorporated by reference as if written herein in their entirety.

FIELD

The present invention is directed to inhibitors of the uptake of monoamine neurotransmitters and pharmaceutically acceptable salts and prodrugs thereof, the chemical synthesis thereof, and the medical use of such compounds for the treatment and/or management of psychotropic disorders, anxiety disorder, generalized anxiety disorder, depression, post-traumatic stress disorder, obsessive-compulsive disorder, panic disorder, hot flashes, senile dementia, migraine, hepatopulmonary syndrome, chronic pain, nociceptive pain, neuropathic pain, painful diabetic retinopathy, bipolar depression, obstructive sleep apnea, psychiatric disorders, premenstrual dysphoric disorder, social phobia, social anxiety disorder, urinary incontinence, anorexia, bulimia nervosa, obesity, ischemia, head injury, calcium overload in brain cells, drug dependence, attention deficit hyperactivity disorder, fibromyalgia, irritable bowel syndrome, and/or premature ejaculation.

BACKGROUND

Venlafaxine (Effexor®) (1-[2-dimethylamino-1-(4-methoxy-phenyl)-ethyl]-cyclohexanol) is a therapeutic agent whose efficacy is hypothesized to act through inhibition of serotonin reuptake and, potentially, norepinephrine reuptake in neuronal cells. Norepinephrine activity modulation is purported to occur at higher doses of venlafaxine than those required for serotonin activity modulation. Venlafaxine also has the potential to modulate dopamine activity, though the interaction in vitro is weak and the clinical relevance of this interaction is unknown. The drug substance is sold as a 50/50 racemic mixture of R- and S-enantiomers.

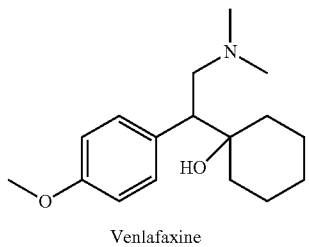 [SMILES: COc1ccc(C(CN(C)C)C2(O)CCCCC2)cc1]

Venlafaxine

Venlafaxine is converted in vivo by oxidative and conjugative degradation to multiple metabolites, at least 48 of which are documented. The major metabolic pathways include phase I metabolism leading to demethylation at the oxygen and/or nitrogen centers and cyclohexyl ring hydroxylation, as well as phase II metabolism including glucuronidation of the hydroxylated metabolites. Because venlafaxine is metabolized by polymorphically-expressed isozymes of cytochrome $P_{450}$ including CYPs 2C19 and 2D6, and because it can act as an inhibitor of CYP2D6, its application in polypharmacy is necessarily complex and has potential for adverse events. These CYPs are involved in the metabolism of medications that are typically prescribed concurrently with venlafaxine. This phenomenon increases interpatient variability in response to polypharmacy. An example of the critical need for improvement of venlafaxine is the observed interpatient variability in "poor metabolizers" having either defective CYP2D6 alleles or total lack of CYP2D6 expression. These patients fail to convert venlafaxine to its equipotent metabolite, 0-desmethylvenlafaxine. Venlafaxine also suffers from a short half-life relative to the majority of serotonin reuptake inhibitors. The half-life of venlafaxine in humans is ~5 hours, while its active metabolite has a $T_{1/2}$ of ~11 hours. As a consequence of its 5-11 hour pharmacological half-life, those taking venlafaxine are at significant risk of SRI discontinuation symptoms if the drug is abruptly discontinued. Furthermore, in order to overcome its short half-life, the drug must be taken 2 (BID) or 3 (TID) times a day. An extended release formulation of Venlafaxine is also available; however, it does not significantly increase the carryover of drug to the next day. Most other serotonin reuptake inhibitors (SRIs) have half-lives≥24 hours. The half-life of the primary active metabolite, 0-desmethylvenlafaxine ("ODV"), is longer than that of the parent compound; however, it is still desirable and beneficial to increase the half-life of ODV.

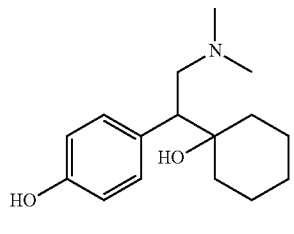

O-desmethylvenlafaxine

SUMMARY OF THE INVENTION

Disclosed herein is a pharmaceutically acceptable acid addition salt of a compound having structural formula I:

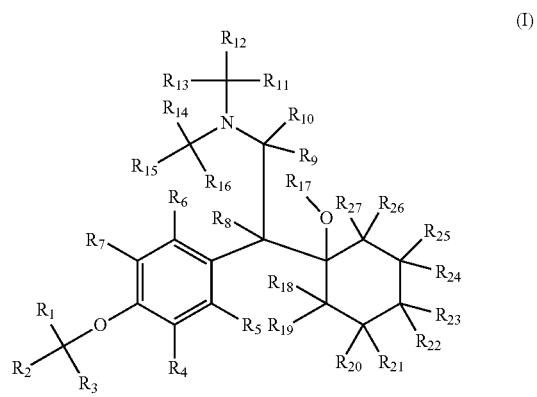

(I)

wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, and $R_{27}$ are independently selected from the group consisting of hydrogen and deuterium; and at least one of $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, and $R_{27}$ is deuterium.

Further disclosed herein is a compound having structural formula II:

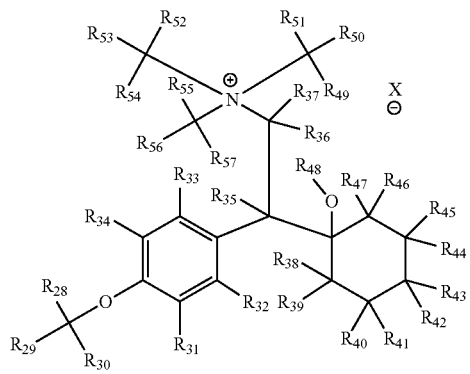

(II)

wherein $R_{28}$, $R_{29}$, $R_{30}$, $R_{31}$, $R_{32}$, $R_{33}$, $R_{34}$, $R_{35}$, $R_{36}$, $R_{37}$, $R_{38}$, $R_{39}$, $R_{40}$, $R_{41}$, $R_{42}$, $R_{43}$, $R_{44}$, $R_{45}$, $R_{46}$, $R_{47}$, $R_{48}$, $R_{49}$, $R_{50}$, $R_{51}$, $R_{52}$, $R_{53}$, $R_{54}$, $R_{55}$, $R_{56}$, and $R_{57}$ are independently selected from the group consisting of hydrogen and deuterium;

at least one of $R_{28}$, $R_{29}$, $R_{30}$, $R_{31}$, $R_{32}$, $R_{33}$, $R_{34}$, $R_{35}$, $R_{36}$, $R_{37}$, $R_{38}$, $R_{39}$, $R_{40}$, $R_{41}$, $R_{42}$, $R_{43}$, $R_{44}$, $R_{45}$, $R_{46}$, $R_{47}$, $R_{48}$, $R_{49}$, $R_{50}$, $R_{51}$, $R_{52}$, $R_{53}$, $R_{54}$, $R_{55}$, $R_{56}$, and $R_{57}$ is deuterium; and X is a leaving group anion.

Further disclosed herein is a compound having structural formula III:

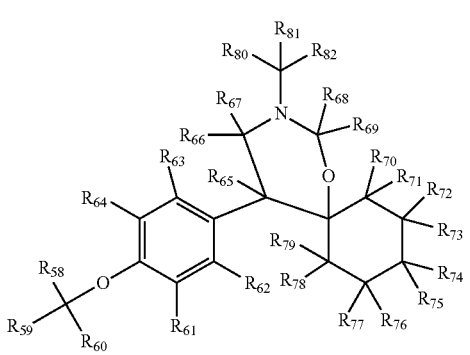

(III)

wherein $R_{58}$, $R_{59}$, $R_{60}$, $R_{61}$, $R_{62}$, $R_{63}$, $R_{64}$, $R_{65}$, $R_{66}$, $R_{67}$, $R_{68}$, $R_{69}$, $R_{70}$, $R_{71}$, $R_{72}$, $R_{73}$, $R_{74}$, $R_{75}$, $R_{76}$, $R_{77}$, $R_{78}$, $R_{79}$, $R_{80}$, $R_{81}$, and $R_{82}$ are independently selected from the group consisting of hydrogen and deuterium; and at least one of $R_{58}$, $R_{59}$, $R_{60}$, $R_{61}$, $R_{62}$, $R_{63}$, $R_{64}$, $R_{65}$, $R_{66}$, $R_{67}$, $R_{68}$, $R_{69}$, $R_{70}$, $R_{71}$, $R_{72}$, $R_{73}$, $R_{74}$, $R_{75}$, $R_{76}$, $R_{77}$, $R_{78}$, $R_{79}$, $R_{80}$, $R_{81}$, and $R_{82}$ is deuterium.

Further disclosed herein is a compound having structural formula IV:

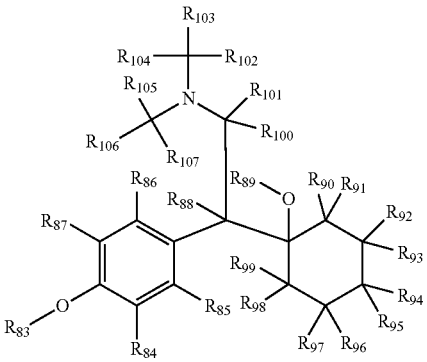

(IV)

wherein $R_{83}$, $R_{84}$, $R_{85}$, $R_{86}$, $R_{87}$, $R_{88}$, $R_{89}$, $R_{90}$, $R_{91}$, $R_{92}$, $R_{93}$, $R_{94}$, $R_{95}$, $R_{96}$, $R_{97}$, $R_{98}$, $R_{99}$, $R_{100}$, $R_{101}$, $R_{102}$, $R_{103}$, $R_{104}$, $R_{105}$, $R_{106}$, and $R_{107}$ are independently selected from the group consisting of hydrogen and deuterium; and at least one of $R_{83}$, $R_{84}$, $R_{85}$, $R_{86}$, $R_{87}$, $R_{88}$, $R_{89}$, $R_{90}$, $R_{91}$, $R_{92}$, $R_{93}$, $R_{94}$, $R_{95}$, $R_{96}$, $R_{97}$, $R_{98}$, $R_{99}$, $R_{100}$, $R_{101}$, $R_{102}$, $R_{103}$, $R_{104}$, $R_{105}$, $R_{106}$, and $R_{107}$ is deuterium.

Also disclosed herein are pharmaceutical compositions comprising at least one compound as disclosed herein or a pharmaceutically acceptable salt, solvate, or prodrug thereof in combination with one or more pharmaceutically acceptable excipients or carriers.

Further disclosed herein is a method for treating, preventing, or ameliorating one or more symptoms of a monoamine-mediated disorder, which comprises administering to a subject a therapeutically effective amount of at least one compound as disclosed herein or a pharmaceutically acceptable salt, solvate, or prodrug thereof.

Additionally provided herein is a method for treating, preventing, or ameliorating one or more symptoms of the following disorders, including, but not limited to: psychotropic disorders, anxiety disorders, generalized anxiety disorder, depression, post-traumatic stress disorder, obsessive-compulsive disorder, panic disorder, hot flashes, senile dementia, migraine, hepatopulmonary syndrome, chronic pain, nociceptive pain, neuropathic pain, painful diabetic retinopathy, bipolar depression, obstructive sleep apnea, psychiatric disorders, premenstrual dysphoric disorder, social phobia, social anxiety disorder, urinary incontinence, anorexia, bulimia nervosa, obesity, ischemia, head injury, calcium overload in brain cells, drug dependence, Gilles de la Tourette syndrome, Shy Drager syndrome, vasomotor flushing, chronic fatigue syndrome, cognition enhancement, attention deficit hyperactivity disorder, fibromyalgia, irritable bowel syndrome, and/or premature ejaculation, which comprises administering to a subject a therapeutically effective amount of at least one compound as disclosed herein or a pharmaceutically acceptable salt, solvate, or prodrug thereof.

Further, disclosed herein are methods of modulating a target selected from the group consisting of a serotonin receptor, a norepinephrine receptor, a serotonin transporter, and a norepinephrine transporter.

In another aspect are processes for preparing a compound having structural formula I as serotonin and/or norepinephrine receptor and/or transporter modulators, or other pharmaceutically acceptable derivatives such as prodrug derivatives, or individual isomers and mixture of isomers or enantiomers thereof.

In another aspect are processes for preparing a pharmaceutically acceptable salt of a compound having structural formula I.

In another aspect are processes for preparing a compound having structural formula II.

In another aspect are processes for preparing a compound having structural formula III.

Additionally disclosed herein is the use of a compound having structural formula II for the manufacture of a compound having structural formula I.

Additionally disclosed herein is the use of a compound having structural formula III for the manufacture of a compound having structural formula I.

Also disclosed herein are articles of manufacture and kits containing compounds as disclosed herein. By way of example only, a kit or article of manufacture can include a container (such as a bottle) with a desired amount of at least one compound (or pharmaceutical composition of a compound) as disclosed herein. Further, such a kit or article of manufacture can further include instructions for using said compound (or pharmaceutical composition of a compound) as disclosed herein. The instructions can be attached to the container, or can be included in a package (such as a box or a plastic or foil bag) holding the container.

In another aspect is the use of at least one compound as disclosed herein in the manufacture of a medicament for treating a disorder in an animal in which serotonin and/or norepinephrine receptors contribute to the pathology and/or symptomology of the disorder. In a further or alternative embodiment, said disorder is, but is not limited to, a psychotropic disorder, anxiety disorder, generalized anxiety disorder, depression, post-traumatic stress disorder, obsessive-compulsive disorder, panic disorder, hot flashes, senile dementia, migraine, hepatopulmonary syndrome, chronic pain, nociceptive pain, neuropathic pain, painful diabetic retinopathy, bipolar depression, obstructive sleep apnea, psychiatric disorders, premenstrual dysphoric disorder, social phobia, social anxiety disorder, urinary incontinence, anorexia, bulimia nervosa, obesity, ischemia, head injury, calcium overload in brain cells, drug dependence, Gilles de la Tourette syndrome, Shy Drager syndrome, vasomotor flushing, chronic fatigue syndrome, cognition enhancement, attention deficit hyperactivity disorder, fibromyalgia, irritable bowel syndrome, and/or premature ejaculation.

It has been found that the hydrochloride salt Forms A-F of the compound of formula I have high crystallinity, i.e., substantially free of amorphous material. Such salts have the advantage that they provide more reproducible dosing results. The hydrochloride salt Forms A-F of the compound of formula I are substantially hygroscopically stable, which alleviates potential problems associated with weight changes of the active ingredient during the manufacture of capsules or tablets. The hydrochloride Forms A-F of the compound of formula I have the additional advantage that they have a low tendency for concentrated aqueous solution to form viscous mixtures upon standing. The hydrochloride salt Forms A-F of the compound of formula I have rapid kinetic aqueous solubility which simplifies aqueous dosing and make them suitable for injectable dosage forms. Furthermore, the hydrochloride salt Forms A-F of the compound of formula I with enhanced solubility characteristics facilitate the dissolution of solid dosage forms in a timely manner. All of these advantages are specifically described herein for all of the pharmaceutical dosage forms, treatment regimens and therapeutic uses described herein form compounds of formula I.

The hydrochloride salt Forms A-F of the compound of formula I have greater kinetic solubility than the free base of the compound of formula I. Additionally, the hydrochloride salt Forms A-F of the compound of formula I are more stable in air and can be used without deliquescence. In one aspect are compounds of formula I which can be stored in air and used without deliquescence, including for periods of more than 1 week, more than 2 weeks, more than 1 month, more than 2 months, more than 3 months and more than 6 months.

INCORPORATION BY REFERENCE

Figure 1:
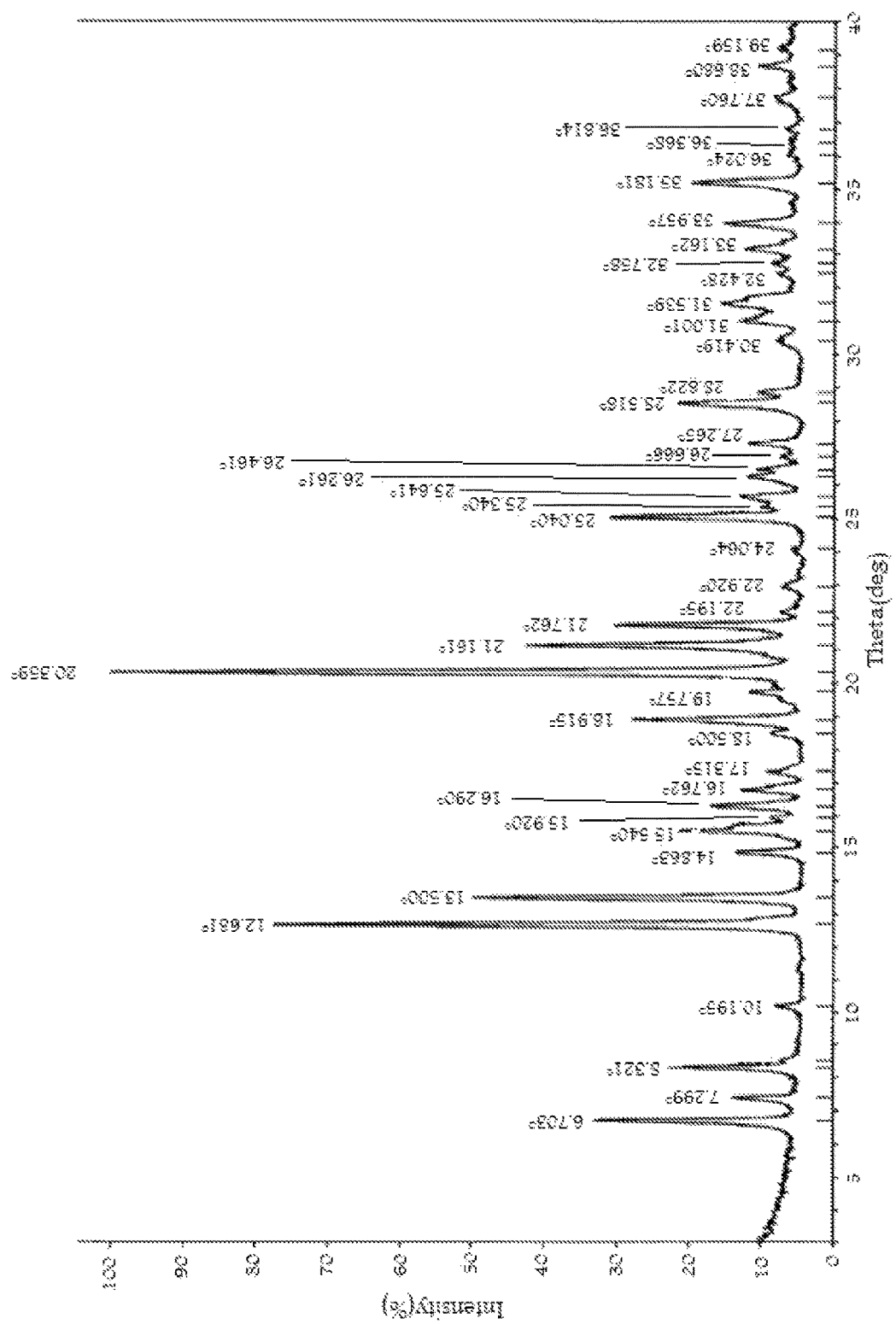
FIG. 1 is an X-ray powder diffraction spectrum of $d_9$-1-[2-dimethylamino-1-(4-methoxyphenyl)-ethyl]-cyclohexanol hydrochloride ($d_9$-venlafaxine hydrochloride, Form A) which was prepared and isolated according to the process disclosed in Example 34.

All publications (including WO07064697A1 and US20070149622A1) and references cited herein, including those in the background section, are expressly incorporated herein by reference in their entirety. However, with respect to any similar or identical terms found in both the incorporated publications or references and those explicitly put forth or defined in this document, then those terms definitions or meanings explicitly put forth in this document shall control in all respects.

DETAILED DESCRIPTION

To facilitate understanding of the disclosure set forth herein, a number of terms are defined below. Generally, the nomenclature used herein and the laboratory procedures in organic chemistry, medicinal chemistry, and pharmacology described herein are those well known and commonly employed in the art. In the event that there is a plurality of definitions for a term used herein, those in this section prevail unless stated otherwise.

As used herein, the singular forms "a," "an," and "the" may refer to plural articles unless specifically stated otherwise.

The term "subject" refers to an animal, including, but not limited to, a primate (e.g., human, monkey, chimpanzee, gorilla, and the like), rodents (e.g., rats, mice, gerbils, hamsters, ferrets, and the like), lagomorphs, swine (e.g., pig, miniature pig), equine, canine, feline, and the like. The terms "subject" and "patient" are used interchangeably herein in reference, for example, to a mammalian subject, such as a human patient.

The terms "treat," "treating," and "treatment" are meant to include alleviating or abrogating a disorder; or one or more of the symptoms associated with the disorder; or alleviating or eradicating the cause(s) of the disorder itself.

The terms "prevent," "preventing," and "prevention" refer to a method of delaying or precluding the onset of a disorder; and/or its attendant symptoms, barring a subject from acquiring a disorder or reducing a subject's risk of acquiring a disorder.

The term "therapeutically effective amount" refers to the amount of a compound that, when administered, is sufficient to prevent development of, or alleviate to some extent, one or more of the symptoms of the disorder being treated. The term "therapeutically effective amount" also refers to the amount of a compound that is sufficient to elicit the biological or medical response of a cell, tissue, system, animal, or human that is being sought by a researcher, veterinarian, medical doctor, or clinician.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, excipient, solvent, or encapsulating material. Each component must be "pharmaceutically acceptable" in the sense of being compatible with the other ingredients of a pharmaceutical formulation. It must also be suitable for use in contact with the tissue or organ of humans and animals without excessive toxicity, irritation, allergic response, immunogenicity, or other problems or complications, commensurate with a reasonable benefit/risk ratio. See, *Remington: The Science and Practice of Pharmacy,* 21st Edition; Lippincott Williams & Wilkins: Philadelphia, Pa., 2005; *Handbook of Pharmaceutical Excipients,* 5th Edition; Rowe et al., Eds., The Pharmaceutical Press and the American Pharmaceutical Association: 2005; and *Handbook of Pharmaceutical Additives,* 3rd Edition; Ash and Ash Eds., Gower Publishing Company: 2007; *Pharmaceutical Preformulation and Formulation,* Gibson Ed., CRC Press LLC: Boca Raton, Fla., 2004).

The term "deuterium enrichment" refers to the percentage of incorporation of deuterium at a given position in a molecule in the place of hydrogen. For example, deuterium enrichment of 1% at a given position means that 1% of molecules in a given sample contain deuterium at the specified position. Because the naturally occurring distribution of deuterium is about 0.0156%, deuterium enrichment at any position in a compound synthesized using non-enriched starting materials is about 0.0156%. The deuterium enrichment can be determined using conventional analytical methods known to one of ordinary skill in the art, including mass spectrometry and nuclear magnetic resonance spectroscopy.

The term "is/are deuterium," when used to describe a given position in a molecule such as $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$ and $R_{26}$ or the symbol "D," when used to represent a given position in a drawing of a molecular structure, means that the specified position is enriched with deuterium above the naturally occurring distribution of deuterium. In one embodiment deuterium enrichment is of no less than about 1%, in another no less than about 5%, in another no less than about 10%, in another no less than about 20%, in another no less than about 50%, in another no less than about 70%, in another no less than about 80%, in another no less than about 90%, and in another no less than about 98% of deuterium at the specified position.

The term "isotopic enrichment" refers to the percentage of incorporation of a less prevalent isotope of an element at a given position in a molecule in the place of the more prevalent isotope of the element.

The term "non-isotopically enriched" refers to a molecule in which the percentages of the various isotopes are substantially the same as the naturally occurring percentages.

The terms "substantially pure" and "substantially homogeneous" mean sufficiently homogeneous to appear free of readily detectable impurities as determined by standard analytical methods used by one of ordinary skill in the art, including, but not limited to, thin layer chromatography (TLC), gel electrophoresis, high performance liquid chromatography (HPLC), infrared spectroscopy (IR), gas chromatography (GC), Ultraviolet Spectroscopy (UV), nuclear magnetic resonance (NMR), atomic force spectroscopy and mass spectroscopy (MS); or sufficiently pure such that further purification would not detectably alter the physical and chemical properties, or biological and pharmacological properties, such as enzymatic and biological activities, of the substance. In certain embodiments, "substantially pure" or "substantially homogeneous" refers to a collection of molecules, wherein at least about 50%, at least about 70%, at least about 80%, at least about 90%, at least about 95%, at least about 98%, at least about 99%, or at least about 99.5% of the molecules are a single compound, including a racemic mixture or single stereoisomer thereof, as determined by standard analytical methods.

The term "about" or "approximately" means an acceptable error for a particular value, which depends in part on how the value is measured or determined. In certain embodiments, "about" can mean 1 or more standard deviations.

The terms "active ingredient" and "active substance" refer to a compound, which is administered, alone or in combination with one or more pharmaceutically acceptable excipients or carriers, to a subject for treating, preventing, or ameliorating one or more symptoms of a disorder.

The terms "drug," "therapeutic agent," and "chemotherapeutic agent" refer to a compound, or a pharmaceutical composition thereof, which is administered to a subject for treating, preventing, or ameliorating one or more symptoms of a disorder.

The term "disorder" as used herein is intended to be generally synonymous, and is used interchangeably with, the terms "disease," "syndrome," and "condition" (as in medical condition), in that all reflect an abnormal condition of the body or of one of its parts that impairs normal functioning and is typically manifested by distinguishing signs and symptoms.

The term "release controlling excipient" refers to an excipient whose primary function is to modify the duration or place of release of the active substance from a dosage form as compared with a conventional immediate release dosage form.

The term "nonrelease controlling excipient" refers to an excipient whose primary function do not include modifying the duration or place of release of the active substance from a dosage form as compared with a conventional immediate release dosage form.

The term "pharmaceutically acceptable acid addition salt" refers to a salt prepared by contacting a compound having a basic functional group with a pharmaceutically acceptable acid.

The term "SNRI," and "serotonin and/or norepinephrine receptor and/or transporter modulator" are interchangeable and refer to a compound that can act as an inhibitor, or an antagonist of a serotonin receptor and/or transporter, and/or norepinephrine receptor and/or transporter.

The term "monoamine-mediated disorder" refers to a disorder that is characterized by abnormal serotonin and/or norepinephrine levels, and when the levels of these neurotransmitters are modified, leads to the amelioration of other abnormal biological processes. A monoamine-mediated disorder may be completely or partially mediated by abnormal serotonin, and/or norepinephrine receptors and/or transporters. In particular, a monoamine-mediated disorder is one in which modulation of serotonin-norepinephrine reuptake activity results in some effect on the underlying condition, disorder, or disease, e.g., administration of an SNRI results in some improvement in at least some of the patients being treated.

The term "halogen", "halide" or "halo" includes fluorine, chlorine, bromine, and iodine.

The term "leaving group" (LG) refers to any atom (or group of atoms) that is stable in its anion or neutral form after it has been displaced by a nucleophile and as such would be obvious to one of ordinary skill and knowledge in the art. The definition of "leaving group" includes but is not limited to: water, methanol, ethanol, chloride, bromide, iodide, an alkyl sulfonate, for example methanesulfonate, ethane sulfonate and the like, an arylsulfonate, for example benzenesulfonate, tolylsulfonate and the like, a perhaloalkanesulfonate, for example trifluoromethanesulfonate, trichloromethanesulfonate and the like, an alkylcarboxylate, for example acetate and the like, a perhaloalkylcarboxylate, for example trifluoroacetate, trichloroacetate and the like, an arylcarboxylate, for example benzoate and the like, an N-hydroxyimide anion, for example N-hydroxyrnaleimide anion, Nhydroxysuccinimide anion, N-hydroxyphthalimide anion, N-hydroxysulfosuccinimide anion and the like.

The term "protecting group" or "removable protecting group" refers to a group which, when bound to a functionality, such as the oxygen atom of a hydroxyl or carboxyl group, or the nitrogen atom of an amino group, prevents reactions from occurring at that functional group, and which can be removed by a conventional chemical or enzymatic step to reestablish the functional group (Greene and Wuts, Protective Groups in Organic Synthesis, $3^{rd}$ Ed., John Wiley & Sons, New York, N.Y., 1999).

In light of the purposes described in the present disclosure, all references to "alkyl" and "aryl" groups or any groups ordinarily containing C—H bonds may include partially or fully deuterated versions as required to affect the improvements outlined herein.

When the notation $R_n$-$R_{(n+x)}$ is used to represent a span of consecutive R groups, what is mean is that all R groups between and including said R groups are comprised by said notation. For example, $R_1$-$R_{27}$ is equivalent to $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, and $R_{27}$.

When the term "increased" is used to compare a certain effect or property of an isotopically enriched (e.g., deuterated) compound to a corresponding non-isotopically enriched compound, what is meant is that said effect or property is increased by greater than about 5%, greater than about 10%, greater than about 20%, greater than about 30%, greater than about 40%, or by greater than about 50% as compared to the corresponding non-isotopically enriched compound. Similarly, when the term "decreased" is used to compare a certain effect or property of an isotopically enriched (e.g., deuterated) compound to a corresponding non-isotopically enriched compound, what is meant is that said effect or property is decreased by greater than about 5%, greater than about 10%, greater than about 20%, greater than about 30%, greater than about 40%, or by greater than about 50% as compared to the corresponding non-isotopically enriched compound.

Deuterium Kinetic Isotope Effect

In an attempt to eliminate foreign substances, such as therapeutic agents, from its circulation system, the animal body expresses various enzymes, such as the cytochrome $P_{450}$ enzymes or CYPs, esterases, proteases, reductases, dehydrogenases, and monoamine oxidases, to react with and convert these foreign substances to more polar intermediates or metabolites for renal excretion. Some of the most common metabolic reactions of pharmaceutical compounds involve the oxidation of a carbon-hydrogen (C—H) bond to either a carbon-oxygen (C—O) or carbon-carbon (C—C) π-bond. The resultant metabolites may be stable or unstable under physiological conditions, and can have substantially different pharmacokinetic, pharmacodynamic, and acute and long-term toxicity profiles relative to the parent compounds. For most drugs, such oxidations are generally rapid and ultimately lead to administration of multiple or high daily doses.

The relationship between the activation energy and the rate of reaction may be quantified by the Arrhenius equation, $k=Ae^{-Eact/RT}$, where $E_{act}$ is the activation energy, T is temperature, R is the molar gas constant, k is the rate constant for the reaction, and A (the frequency factor) is a constant specific to each reaction that depends on the probability that the molecules will collide with the correct orientation. The Arrhenius equation states that the fraction of molecules that have enough energy to overcome an energy barrier, that is, those with energy at least equal to the activation energy, depends exponentially on the ratio of the activation energy to thermal energy (RT), the average amount of thermal energy that molecules possess at a certain temperature.

The transition state in a reaction is a short lived state (on the order of $10^{-14}$ sec) along the reaction pathway during which the original bonds have stretched to their limit. By definition, the activation energy $E_{act}$ for a reaction is the energy required to reach the transition state of that reaction. Reactions that involve multiple steps will necessarily have a number of transition states, and in these instances, the activation energy for the reaction is equal to the energy difference between the reactants and the most unstable transition state. Once the transition state is reached, the molecules can either revert, thus reforming the original reactants, or new bonds form giving rise to the products. This dichotomy is possible because both pathways, forward and reverse, result in the release of energy. A catalyst facilitates a reaction process by lowering the activation energy leading to a transition state. Enzymes are examples of biological catalysts that reduce the energy necessary to achieve a particular transition state.

A carbon-hydrogen bond is by nature a covalent chemical bond. Such a bond forms when two atoms of similar electronegativity share some of their valence electrons, thereby creating a force that holds the atoms together. This force or bond strength can be quantified and is expressed in units of energy, and as such, covalent bonds between various atoms can be classified according to how much energy must be applied to the bond in order to break the bond or separate the two atoms.

The bond strength is directly proportional to the absolute value of the ground-state vibrational energy of the bond. This vibrational energy, which is also known as the zero-point vibrational energy, depends on the mass of the atoms that form the bond. The absolute value of the zero-point vibrational energy increases as the mass of one or both of the atoms making the bond increases. Since deuterium (D) has twice the mass of hydrogen (H), it follows that a C-D bond is stronger than the corresponding C—H bond. Compounds with C-D bonds are frequently indefinitely stable in $H_2O$, and have been widely used for isotopic studies. If a C—H bond is broken during a rate-determining step in a chemical reaction (i.e. the step with the highest transition state energy), then substituting a deuterium for that hydrogen will cause a decrease in the reaction rate and the process will slow down. This phenomenon is known as the Deuterium Kinetic Isotope Effect (DKIE). The magnitude of the DKIE can be expressed as the ratio between the rates of a given reaction in which a C—H bond is broken, and the same reaction where deuterium is substituted for hydrogen. The DKIE can range from about 1 (no isotope effect) to very large numbers, such as 50 or more, meaning that the reaction can be fifty, or more, times slower when deuterium is substituted for hydrogen. High DKIE values may be due in part to a phenomenon known as tunneling, which is a consequence of the uncertainty principle. Tunneling is ascribed to the small mass of a hydrogen atom, and occurs because transition states involving a proton can sometimes form in the absence of the required activation energy. Because deuterium has more mass than hydrogen, it statistically has a much lower probability of undergoing this phenomenon. Substitution of tritium for hydrogen results in yet a stronger bond than deuterium and gives numerically larger isotope effects Discovered in 1932 by Urey, deuterium (D) is a stable and non-radioactive isotope of hydrogen. It was the first isotope to be separated from its element in pure form and has twice the mass of hydrogen, and makes up about 0.02% of the total mass of hydrogen (in this usage meaning all hydrogen isotopes) on earth. When two deuterium atoms bond with one oxygen, deuterium oxide ($D_2O$ or "heavy water") is formed. $D_2O$ looks and tastes like $H_2O$, but has different physical properties. It boils at 101.41° C. and freezes at 3.79° C. Its heat capacity, heat of fusion, heat of vaporization, and entropy are all higher than $H_2O$. It is more viscous and has different solubilizing properties than $H_2O$.

When pure $D_2O$ is given to rodents, it is readily absorbed and reaches an equilibrium level that is usually about eighty percent of the concentration of what was consumed. The quantity of deuterium required to induce toxicity is extremely high. When 0% to as much as 15% of the body water has been replaced by $D_2O$, animals are healthy but are unable to gain weight as fast as the control (untreated) group. When about 15% to about 20% of the body water has been replaced with $D_2O$, the animals become excitable. When about 20% to about 25% of the body water has been replaced with $D_2O$, the animals are so excitable that they go into frequent convulsions when stimulated. Skin lesions, ulcers on the paws and muzzles, and necrosis of the tails appear. The animals also become very aggressive; males becoming almost unmanageable. When about 30%, of the body water has been replaced with $D_2O$, the animals refuse to eat and become comatose. Their body weight drops sharply and their metabolic rates drop far below normal, with death occurring at about 30 to about 35% replacement with $D_2O$. The effects are reversible unless more than thirty percent of the previous body weight has been lost due to $D_2O$. Studies have also shown that the use of $D_2O$ can delay the growth of cancer cells and enhance the cytotoxicity of certain antineoplastic agents.

Tritium (T) is a radioactive isotope of hydrogen, used in research, fusion reactors, neutron generators and radiopharmaceuticals. Mixing tritium with a phosphor provides a continuous light source, a technique that is commonly used in wristwatches, compasses, rifle sights and exit signs. It was discovered by Rutherford, Oliphant and Harteck in 1934, and is produced naturally in the upper atmosphere when cosmic rays react with $H_2$ molecules. Tritium is a hydrogen atom that has 2 neutrons in the nucleus and has an atomic weight close to 3. It occurs naturally in the environment in very low concentrations, most commonly found as $T_2O$, a colorless and odorless liquid. Tritium decays slowly (half-life=12.3 years) and emits a low energy beta particle that cannot penetrate the outer layer of human skin. Internal exposure is the main hazard associated with this isotope, yet it must be ingested in large amounts to pose a significant health risk. As compared with deuterium, a lesser amount of tritium must be consumed before it reaches a hazardous level.

Deuteration of pharmaceuticals to improve pharmacokinetics (PK), pharmacodynamics (PD), and toxicity profiles, has been demonstrated previously with some classes of drugs. For example, the DKIE was used to decrease the hepatotoxicity of halothane by presumably limiting the production of reactive species such as trifluoroacetyl chloride. However, this method may not be applicable to all drug classes. For example, deuterium incorporation can lead to metabolic switching. The concept of metabolic switching asserts that xenogens, when sequestered by Phase I enzymes, may bind transiently and re-bind in a variety of conformations prior to the chemical reaction (e.g., oxidation). This hypothesis is supported by the relatively vast size of binding pockets in many Phase I enzymes and the promiscuous nature of many metabolic reactions. Metabolic switching can potentially lead to different proportions of known metabolites as well as altogether new metabolites. This new metabolic profile may impart more or less toxicity. Such pitfalls are non-obvious and are not predictable a priori for any drug class.

Deuterated Phenethylamine Derivatives

Venlafaxine is a substituted phenethylamine-based SNRI. The carbon-hydrogen bonds of venlafaxine contain a naturally occurring distribution of hydrogen isotopes, namely 1H or protium (about 99.9844%), 2H or deuterium (about 0.0156%), and 3H or tritium (in the range between about 0.5 and 67 tritium atoms per 1018 protium atoms). Increased levels of deuterium incorporation may produce a detectable Kinetic Isotope Effect (KIE) that could affect the pharmacokinetic, pharmacologic and/or toxicologic profiles of such SNRIs in comparison with the compound having naturally occurring levels of deuterium.

The novel approach to designing and synthesizing new analogs of venlafaxine and related compounds through incorporation of deuterium disclosed herein may generate novel monoamine reuptake inhibitors with unexpected and non-obvious improvements of pharmacological, pharmacokinetic and toxicological properties in comparison to the non-isotopically enriched monoamine reuptake inhibitors.

Both N-methyl groups, the single O-methyl, and several sites on the cyclohexyl ring of venlafaxine are now known to be sites of cytochrome $P_{450}$ metabolism. The toxicities of all resultant metabolites are not known. Furthermore, because polymorphically expressed CYPs such as 2C19 and 2D6 oxidize venlafaxine, and because venlafaxine inhibits the polymorphically expressed CYP2D6, the prevention of such interactions decreases interpatient variability, decreases drug-drug interactions, increases $T_{1/2}$, decreases the necessary $C_{max}$, and improves several other ADMET parameters. For example, the half-life of venlafaxine ranges from 3-7 hours. The equipotent metabolite, 0-demethylated venlafaxine (ODV), has a half-life averaging 11 hours. Various deuteration patterns can be used to a) alter the ratio of active metabolites, b) reduce or eliminate unwanted metabolites, c) increase the half-life of the parent drug, and/or d) increase the half-life of active metabolites and create a more effective drug and a safer drug for polypharmacy, whether the polypharmacy be intentional or not. High doses of venlafaxine are often prescribed in order to reach levels capable of inhibiting norepinephrine reuptake. Unfortunately, high doses are also associated with hypertension. Since these phenomena are linked by the pharmaceutical agent rather than the pharmacological target, they are theoretically separable by increasing the half-life, thus allowing dosing in a range that lowers the $C_{max}$ and thus may avoid triggering the mechanism leading to hypertension. Further illustrating this point, venlafaxine is known to display linear kinetics at the low end of the dose range, 75 mg/day, but displays non-linear kinetics at the high end of the dose range, ~400 mg/day, as a result of the saturation of clearance mechanisms. This non-linearity produces an ascending, rather than a flat, dose-response curve for venlafaxine. The deuteration approach has strong potential to slow metabolism through the previously saturated mechanism allowing linear, more predictable ADMET responses throughout the dose range (which would also be lower via this invention). This leads to lesser interpatient variability of the type that can lead to the hypertensive effects.

The compounds disclosed herein have the potential to uniquely maintain the beneficial aspects of the non-isotopically enriched drugs while substantially increasing the half-life ($T_{1/2}$), lowering the maximum plasma concentration ($C_{max}$) of the minimum efficacious dose (MED), lowering the efficacious dose and thus decreasing the non-mechanism-related toxicity, and/or lowering the probability of drug-drug interactions. These drugs also have strong potential to reduce the cost-of-goods (COG) owing to the ready availability of inexpensive sources of deuterated reagents combined with previously mentioned potential for lowering the therapeutic dose. It has been discovered that deuteration at the N-methyl and the O-methyl groups alone, deuteration at the N-methyl and the O-methyl groups in combination, or deuteration of additional sites found to be labile as a result of metabolic switching are effective in achieving some of the objectives disclosed herein.

In the following embodiments below, further embodiments of each are provided, wherein each compound may be substantially a single enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, substantially an individual diastereomer, or a mixture of about 90% or more by weight of an individual diastereomer and about 10% or less by weight of any other diastereomer.

Also in the following embodiments below, further embodiments of each are provided, wherein at least one of each R group designated to be deuterium independently has deuterium enrichment of no less than about 1%, no less than about 5%, no less than about 10%, no less than about 20%, no less than about 50%, no less than about 70%, no less than about 80%, no less than about 90%, no less than about 95%, or no less than about 98%.

In one embodiment, disclosed herein is a pharmaceutically acceptable acid addition salt of a compound having structural formula I:

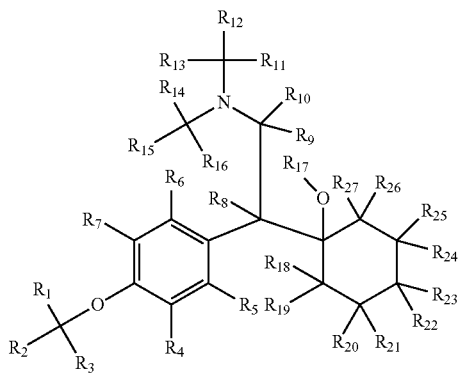

wherein $R_1$-$R_{27}$ are independently selected from the group consisting of hydrogen and deuterium; and
at least one of $R_1$-$R_{27}$ is deuterium.

In yet another embodiment, at least one of $R_1$, $R_2$, and $R_3$ is deuterium.

In yet another embodiment, $R_1$, $R_2$, and $R_3$ are deuterium.

In yet another embodiment, at least one of $R_{11}$, $R_{12}$, and $R_{13}$ is deuterium.

In yet another embodiment, $R_{11}$, $R_{12}$, and $R_{13}$ are deuterium.

In yet another embodiment, at least one of $R_1$, $R_2$, $R_3$, $R_{11}$, $R_{12}$, and $R_{13}$ is deuterium.

In yet another embodiment, $R_1$, $R_2$, $R_3$, $R_{11}$, $R_{12}$, and $R_{13}$ are deuterium.

In yet another embodiment, at least one of $R_{11}$, $R_{12}$, $R_{13}$, $R_{14}$, $R_{15}$, and $R_{16}$ is deuterium.

In yet another embodiment, $R_{11}$, $R_{12}$, $R_{13}$, $R_{14}$, $R_{15}$, and $R_{16}$ are deuterium.

In yet another embodiment, at least one of $R_1$, $R_2$, $R_3$, $R_{11}$, $R_{12}$, $R_{13}$, $R_{14}$, $R_{15}$, and $R_{16}$ is deuterium.

In yet another embodiment, $R_1$, $R_2$, $R_3$, $R_{11}$, $R_{12}$, $R_{13}$, $R_{14}$, $R_{15}$, and $R_{16}$ are deuterium.

In yet another embodiment, at least one of $R_1$, $R_2$, and $R_3$ is deuterium; and $R_4$-$R_{27}$ are hydrogen.

In yet another embodiment, $R_1$, $R_2$, and $R_3$ are deuterium; and $R_4$-$R_{27}$ are hydrogen.

In yet another embodiment, at least one of $R_{11}$, $R_{12}$, and $R_{13}$ is deuterium; and $R_1$, $R_2$, $R_3$, $R_4$-$R_{10}$, and $R_{14}$-$R_{27}$ are hydrogen.

In yet another embodiment, $R_{11}$, $R_{12}$, and $R_{13}$ are deuterium; and $R_1$, $R_2$, $R_3$, $R_4$-$R_{10}$, and $R_{14}$-$R_{27}$ are hydrogen.

In yet another embodiment, at least one of $R_1$, $R_2$, $R_3$, $R_{11}$, $R_{12}$, and $R_{13}$ is deuterium; and $R_4$-$R_{10}$ and $R_{14}$-$R_{27}$ are hydrogen.

In yet another embodiment, $R_1$, $R_2$, $R_3$, $R_{11}$, $R_{12}$, and $R_{13}$ are deuterium; and $R_4$-$R_{10}$ and $R_{14}$-$R_{27}$ are hydrogen.

In yet another embodiment, at least one of $R_{11}$, $R_{12}$, $R_{13}$, $R_{14}$, $R_{15}$, and $R_{16}$ is deuterium; and $R_4$-$R_{10}$ and $R_{17}$-$R_{27}$ are hydrogen.

In yet another embodiment, $R_{11}$, $R_{12}$, $R_{13}$, $R_{14}$, $R_{15}$, and $R_{16}$ are deuterium; and $R_1$-$R_{10}$ and $R_{17}$-$R_{27}$ are hydrogen.

In yet another embodiment, at least one of $R_1$, $R_2$, $R_3$, $R_{11}$, $R_{12}$, $R_{13}$, $R_{14}$, $R_{15}$, and $R_{16}$ is deuterium; and $R_4$-$R_{10}$ and $R_{17}$-$R_{27}$ are hydrogen.

In yet another embodiment, $R_1$, $R_2$, $R_3$, $R_{11}$, $R_{12}$, $R_{13}$, $R_{14}$, $R_{15}$, and $R_{16}$ are deuterium; and $R_4$-$R_{10}$ and $R_{17}$-$R_{27}$ are hydrogen.

In yet another embodiment, a pharmaceutically acceptable acid addition salt of a compound has a structural formula selected from the group consisting of:

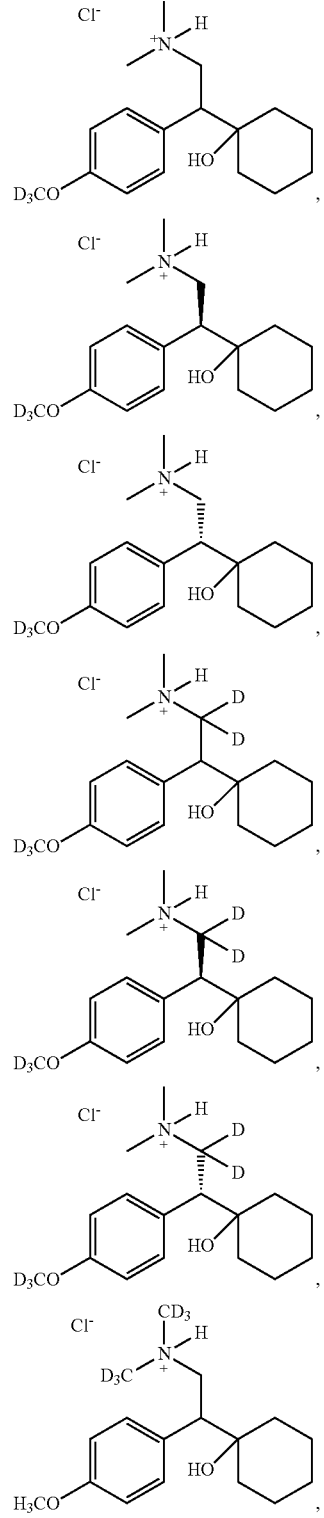

-continued
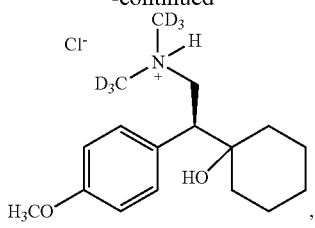
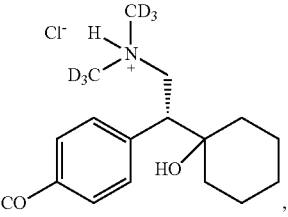
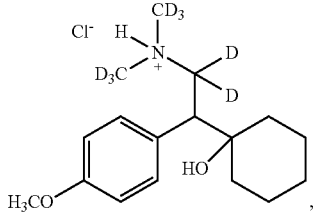
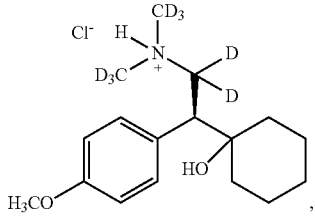
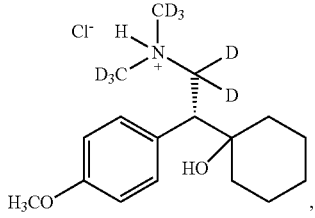
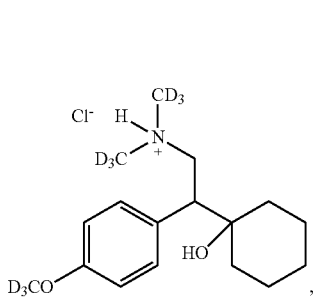
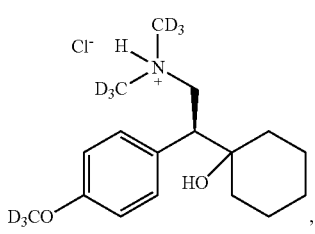
-continued
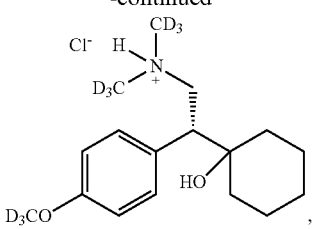
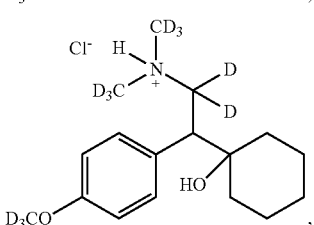
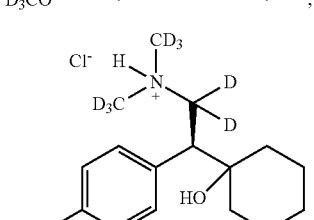
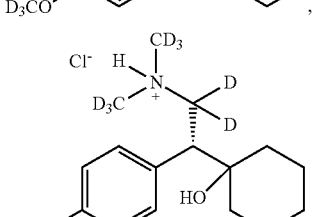
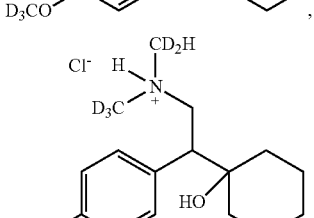
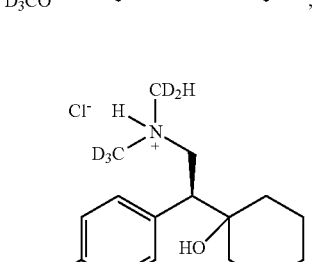

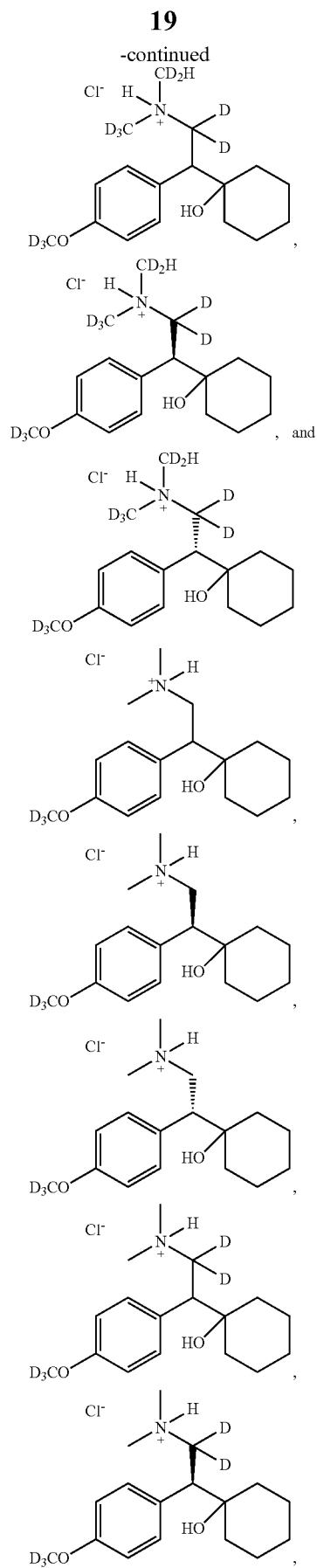
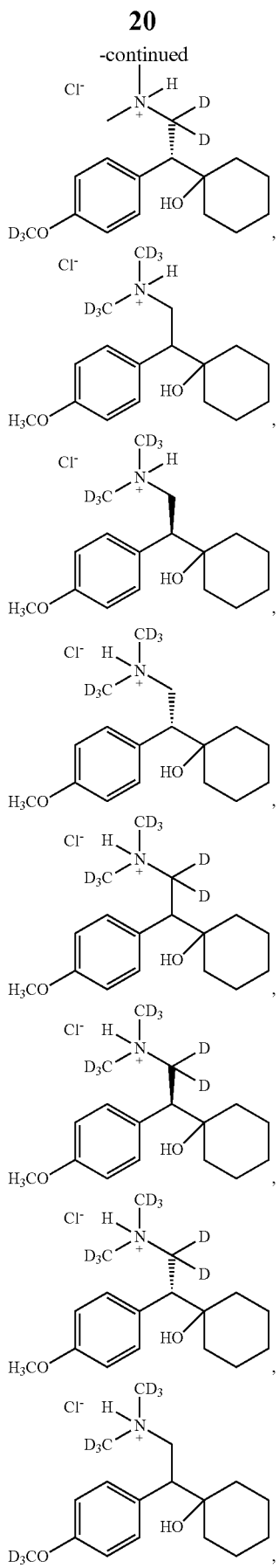

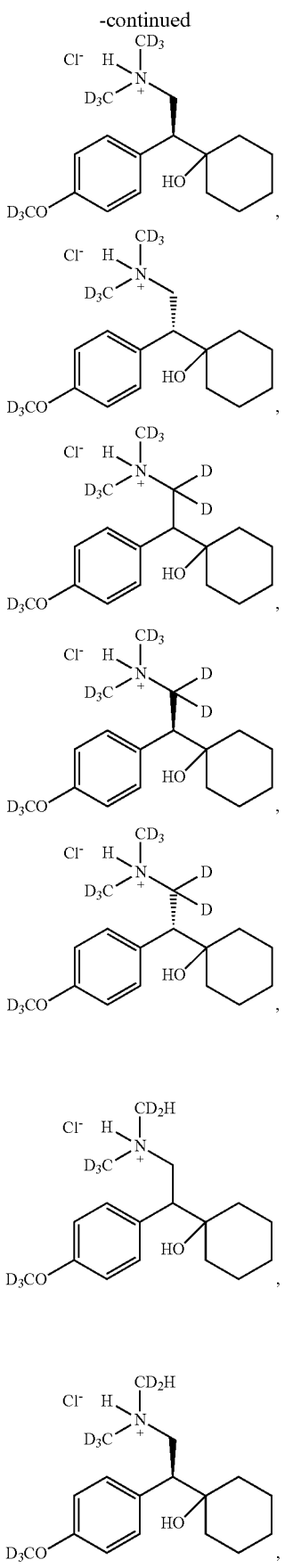

In one embodiment, disclosed herein is a compound having structural formula II:

(II)

wherein $R_{28}$-$R_{57}$ are independently selected from the group consisting of hydrogen and deuterium;

at least one of $R_{28}$-$R_{57}$ is deuterium; and

X is a leaving group anion.

In yet another embodiment, at least one of $R_{28}$, $R_{29}$, and $R_{30}$ is deuterium.

In yet another embodiment, $R_{28}$, $R_{29}$, and $R_{30}$ are deuterium.

In yet another embodiment, at least one of $R_{49}$, $R_{50}$, $R_{51}$, $R_{52}$, $R_{53}$, $R_{54}$, $R_{55}$, $R_{56}$, and $R_{57}$ is deuterium.

In yet another embodiment, $R_{49}$, $R_{50}$, $R_{51}$, $R_{52}$, $R_{53}$, $R_{54}$, $R_{55}$, $R_{56}$, and $R_{57}$ are deuterium.

In yet another embodiment, at least one of $R_{28}$, $R_{29}$, $R_{30}$, $R_{49}$, $R_{50}$, $R_{51}$, $R_{52}$, $R_{53}$, $R_{54}$, $R_{55}$, $R_{56}$, and $R_{57}$ is deuterium.

In yet another embodiment, $R_{28}$, $R_{29}$, $R_{30}$, $R_{49}$, $R_{50}$, $R_{51}$, $R_{52}$, $R_{53}$, $R_{54}$, $R_{55}$, $R_{56}$, and $R_{57}$ are deuterium.

In yet another embodiment, at least one of $R_{28}$, $R_{29}$, and $R_{30}$ is deuterium; and $R_{31}$-$R_{57}$ are hydrogen.

In yet another embodiment, $R_{28}$, $R_{29}$, and $R_{30}$ are deuterium; and $R_{31}$-$R_{57}$ are hydrogen.

In yet another embodiment, at least one of $R_{49}$, $R_{50}$, $R_{51}$, $R_{52}$, $R_{53}$, $R_{54}$, $R_{55}$, $R_{56}$, and $R_{57}$ is deuterium; and $R_{28}$-$R_{48}$ are hydrogen.

In yet another embodiment, $R_{49}$, $R_{50}$, $R_{51}$, $R_{52}$, $R_{53}$, $R_{54}$, $R_{55}$, $R_{56}$, and $R_{57}$ are deuterium; and $R_{28}$-$R_{48}$ are hydrogen.

In yet another embodiment, at least one of $R_{28}$, $R_{29}$, $R_{30}$, $R_{49}$, $R_{50}$, $R_{51}$, $R_{52}$, $R_{53}$, $R_{54}$, $R_{55}$, $R_{56}$, and $R_{57}$ is deuterium; and $R_{31}$-$R_{48}$ are hydrogen.

In yet another embodiment, $R_{28}$, $R_{29}$, $R_{30}$, $R_{49}$, $R_{50}$, $R_{51}$, $R_{52}$, $R_{53}$, $R_{54}$, $R_{55}$, $R_{56}$, and $R_{57}$ are deuterium; and $R_{31}$-$R_{48}$ are hydrogen.

In one embodiment, X is selected from the group consisting of halogen, alkylsulfonate, arylsulfonate, perhaloalkanesulfonate, $CH_3OSO_3^-$, and $CD_3OSO_3^-$.

In another embodiment, X is iodide.

In yet another embodiment, a compound has a structural formula selected from the group consisting of:

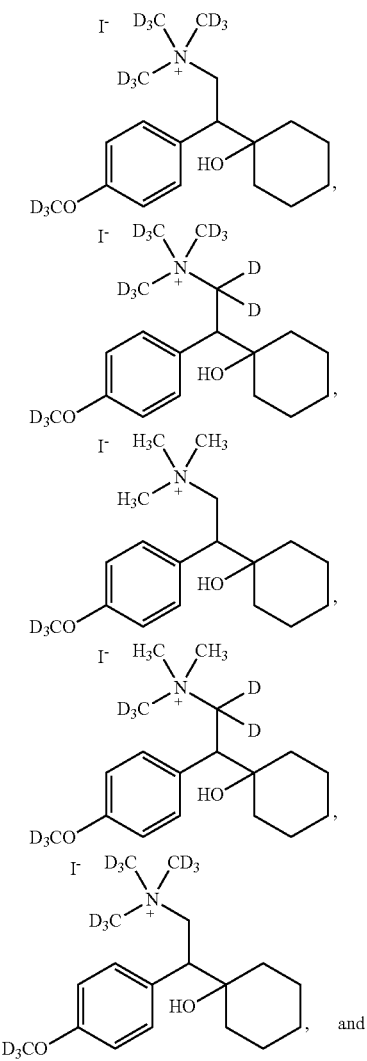

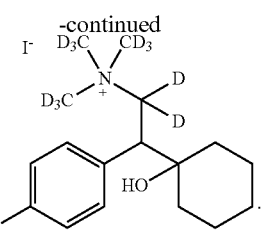

In one embodiment, disclosed herein is a compound having structural formula II:

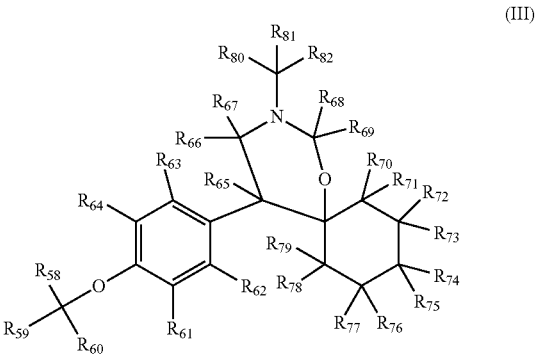

(III)

wherein $R_{58}$-$R_{82}$ are independently selected from the group consisting of hydrogen and deuterium; and at least one of $R_{58}$-$R_{82}$ is deuterium.

In yet another embodiment, at least one of $R_{58}$, $R_{59}$, and $R_{60}$ is deuterium.

In yet another embodiment, $R_{58}$, $R_{59}$, and $R_{60}$ are deuterium.

In yet another embodiment, at least one of $R_{68}$, $R_{69}$, $R_{80}$, $R_{81}$, and $R_{82}$ is deuterium.

In yet another embodiment, $R_{68}$, $R_{69}$, $R_{80}$, $R_{81}$, and $R_{82}$ are deuterium.

In yet another embodiment, at least one of $R_{58}$, $R_{59}$, $R_{60}$, $R_{68}$, $R_{69}$, $R_{80}$, $R_{81}$, and $R_{82}$ is deuterium.

In yet another embodiment, $R_{58}$, $R_{59}$, $R_{60}$, $R_{68}$, $R_{69}$, $R_{80}$, $R_{81}$, and $R_{82}$ are deuterium.

In yet another embodiment, at least one of $R_{58}$, $R_{59}$, and $R_{60}$ is deuterium; and $R_{61}$-$R_{82}$ are hydrogen.

In yet another embodiment, $R_{58}$, $R_{59}$, and $R_{60}$ are deuterium; and $R_{61}$-$R_{82}$ are hydrogen.

In yet another embodiment, at least one of $R_{68}$, $R_{69}$, $R_{80}$, $R_{81}$, and $R_{82}$ is deuterium; and $R_{58}$-$R_{67}$ and $R_{70}$-$R_{79}$ are hydrogen.

In yet another embodiment, $R_{68}$, $R_{69}$, $R_{80}$, $R_{81}$, and $R_{82}$ are deuterium; and $R_{58}$-$R_{67}$ and $R_{70}$-$R_{79}$ are hydrogen.

In yet another embodiment, at least one of $R_{58}$, $R_{59}$, $R_{60}$, $R_{68}$, $R_{69}$, $R_{80}$, $R_{81}$, and $R_{82}$ is deuterium; and $R_{61}$-$R_{67}$ and $R_{70}$-$R_{79}$ are hydrogen.

In yet another embodiment, $R_{58}$, $R_{59}$, $R_{60}$, $R_{68}$, $R_{69}$, $R_{80}$, $R_{81}$, and $R_{82}$ are deuterium; and $R_{61}$-$R_{67}$ and $R_{70}$-$R_{79}$ are hydrogen.

In yet another embodiment, a compound has a structural formula selected from the group consisting of:

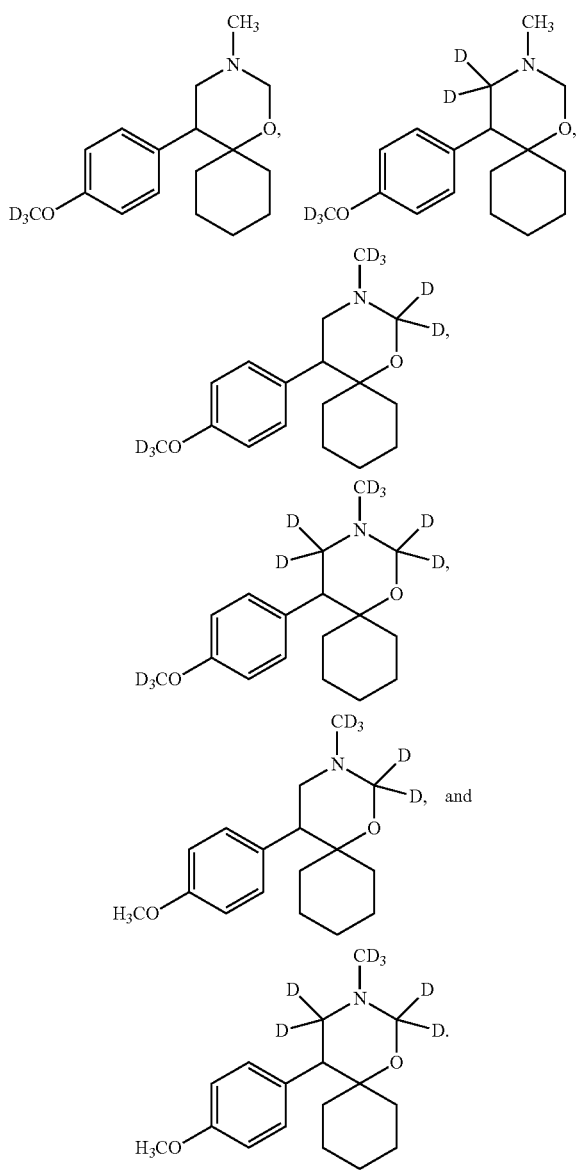

In one embodiment, disclosed herein is a compound having structural formula IV:

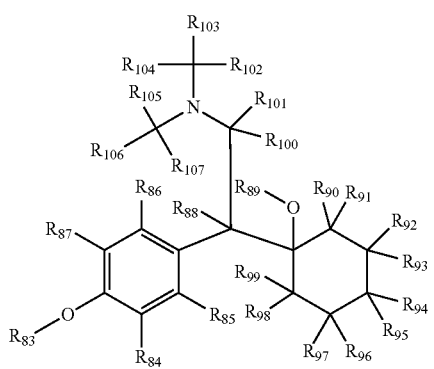

or a pharmaceutically acceptable salt, solvate, or prodrug thereof; wherein $R_{83}$-$R_{107}$ are independently selected from the group consisting of hydrogen and deuterium; and at least one of $R_{83}$-$R_{107}$ is deuterium.

In yet another embodiment, at least one of $R_{102}$, $R_{103}$, and $R_{104}$ is deuterium.

In yet another embodiment, Riot, $R_{103}$, and $R_{104}$ are deuterium.

In yet another embodiment, at least one of $R_{102}$, $R_{103}$, $R_{104}$, $R_{105}$, $R_{106}$, and $R_{107}$ is deuterium.

In yet another embodiment, $R_{102}$, $R_{103}$, $R_{104}$, $R_{105}$, $R_{106}$, and $R_{107}$ are deuterium.

In yet another embodiment, at least one of $R_{100}$ and $R_{101}$ is deuterium.

In yet another embodiment, $R_{100}$ and $R_{101}$ are deuterium.

In yet another embodiment, at least one of $R_{100}$, $R_{101}$, $R_{102}$, $R_{103}$, and $R_{104}$ is deuterium.

In yet another embodiment, $R_{100}$, $R_{101}$, $R_{102}$, $R_{103}$, and $R_{104}$ are deuterium.

In yet another embodiment, at least one of $R_{100}$, $R_{101}$, $R_{102}$, $R_{103}$, $R_{104}$, $R_{105}$, $R_{106}$, and $R_{107}$ is deuterium.

In yet another embodiment, $R_{100}$, $R_{101}$, $R_{102}$, $R_{103}$, $R_{104}$, $R_{105}$, $R_{106}$, and $R_{107}$ are deuterium.

In yet another embodiment, at least one of $R_{102}$, $R_{103}$, and $R_{104}$ is deuterium, and $R_{83}$-$R_{101}$, $R_{105}$, $R_{106}$, and $R_{107}$ are hydrogen.

In yet another embodiment, $R_{102}$, $R_{103}$, and $R_{104}$ are deuterium, and $R_{83}$-$R_{101}$, $R_{105}$, $R_{106}$, and $R_{107}$.

In yet another embodiment, at least one of $R_{102}$, $R_{103}$, $R_{104}$, $R_{105}$, $R_{106}$, and $R_{107}$ is deuterium, and $R_{83}$-$R_{101}$ are hydrogen.

In yet another embodiment, $R_{102}$, $R_{103}$, $R_{104}$, $R_{105}$, $R_{106}$, and $R_{107}$ are deuterium, and $R_{83}$-$R_{101}$ are hydrogen.

In yet another embodiment, at least one of $R_{100}$ and $R_{101}$ is deuterium, and $R_{83}$-$R_{99}$ and $R_{102}$-$R_{107}$ are hydrogen.

In yet another embodiment, $R_{100}$ and $R_{101}$ are deuterium, and $R_{83}$-$R_{99}$ and Riot-$R_{107}$ are hydrogen.

In yet another embodiment, at least one of $R_{100}$, $R_{101}$, $R_{102}$, $R_{103}$, and $R_{104}$ is deuterium, and $R_{83}$-$R_{99}$, $R_{105}$, $R_{106}$, and $R_{107}$ are hydrogen.

In yet another embodiment, $R_{100}$, $R_{101}$, $R_{102}$, $R_{103}$, and $R_{104}$ are deuterium, and $R_{83}$-$R_{99}$, $R_{105}$, $R_{106}$, and $R_{107}$ are hydrogen.

In yet another embodiment, at least one of $R_{100}$-$R_{107}$ is deuterium, and $R_{83}$-$R_{99}$ are hydrogen.

In yet another embodiment, $R_{100}$-$R_{107}$ are deuterium, and $R_{83}$-$R_{99}$ are hydrogen.

In yet another embodiment, a compound has a structural formula selected from the group consisting of:

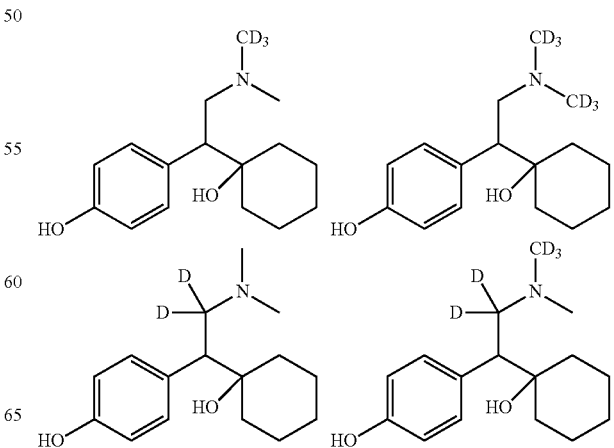

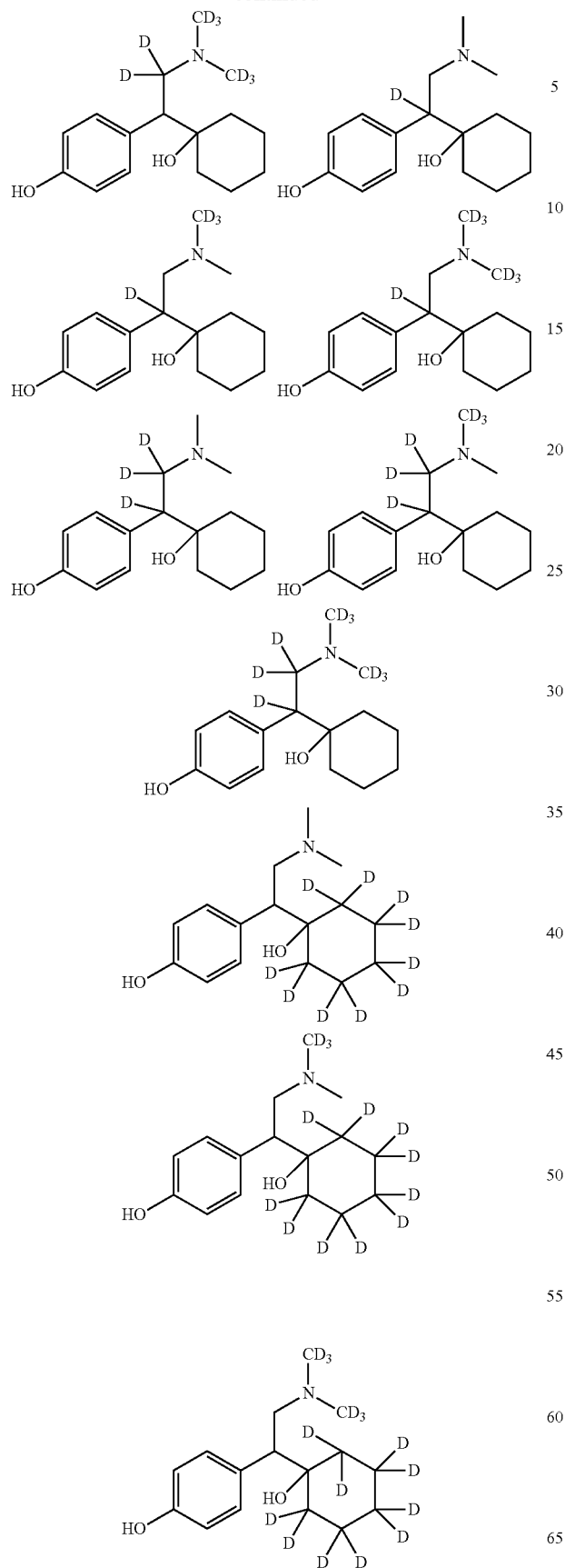
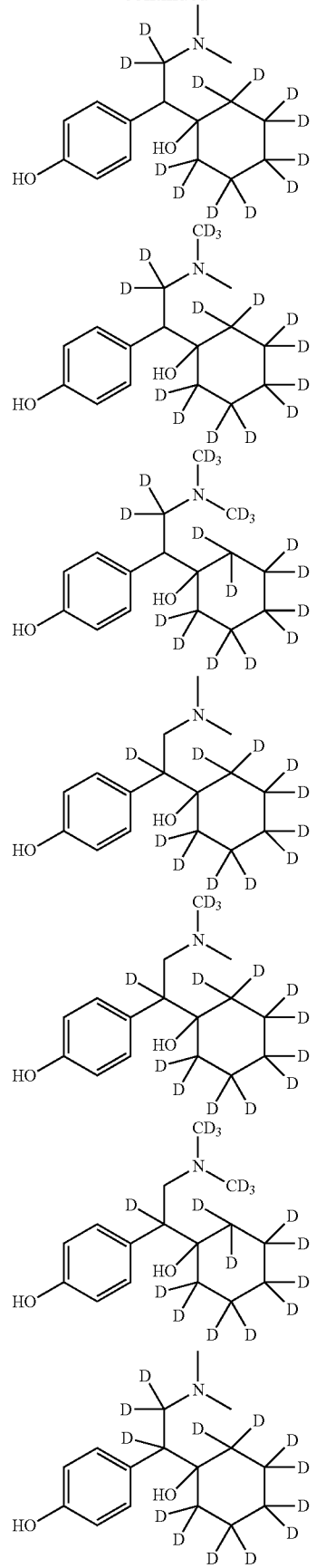

-continued
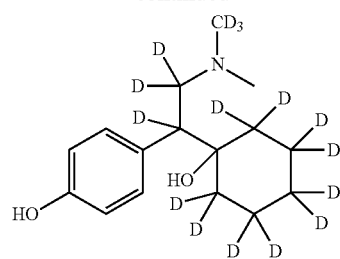
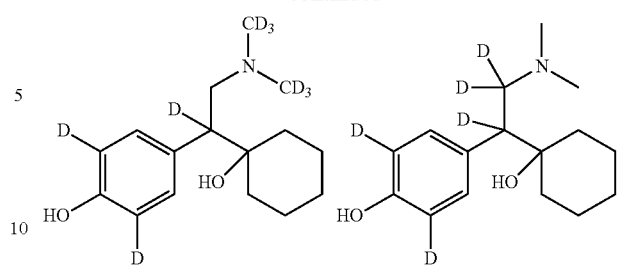
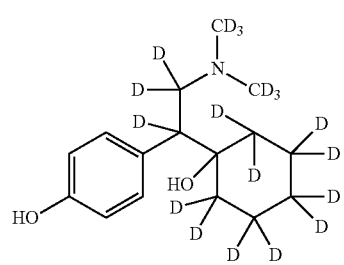
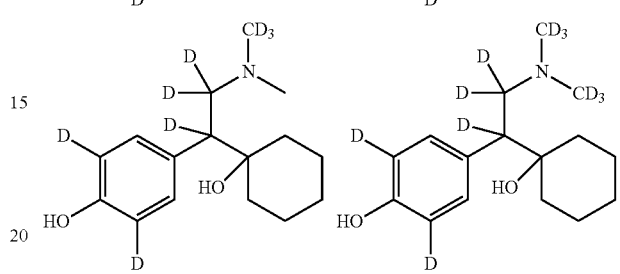
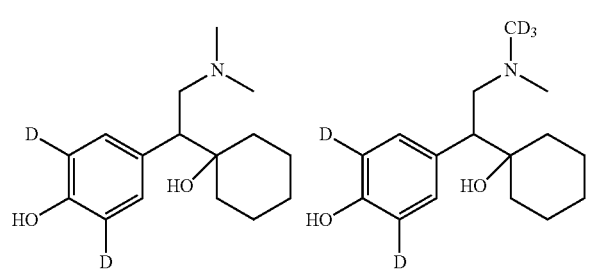
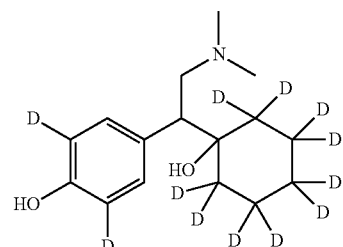
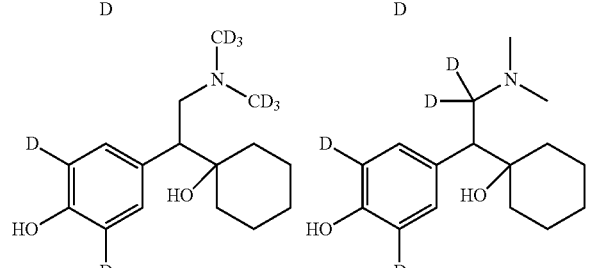
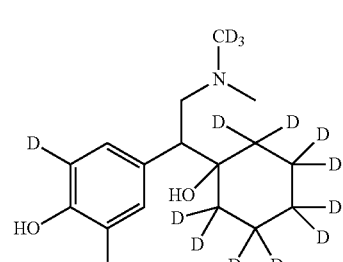
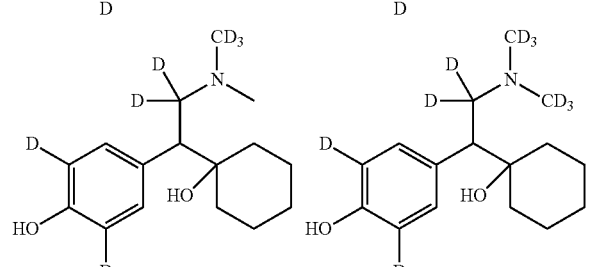
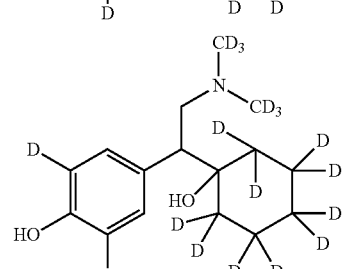
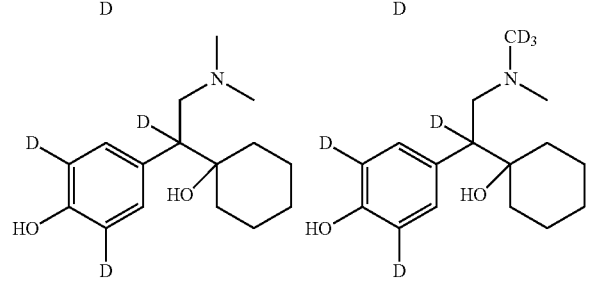
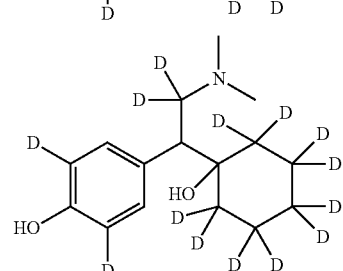

31
-continued
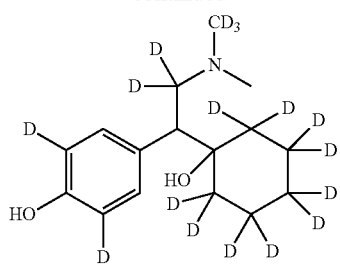
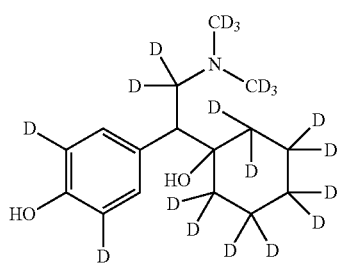
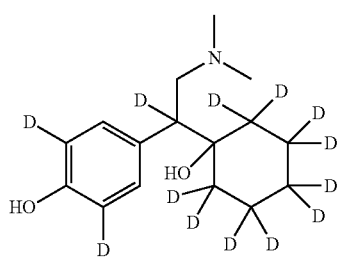
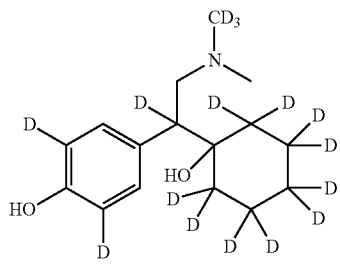
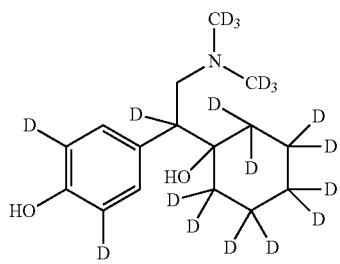
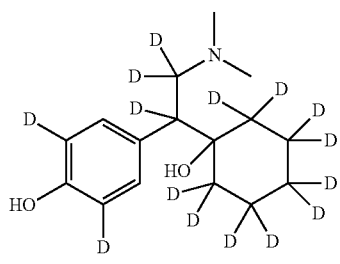
32
-continued
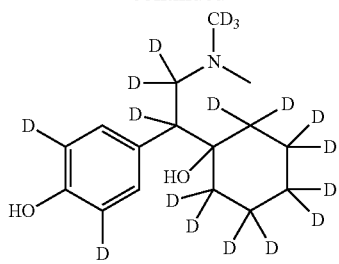
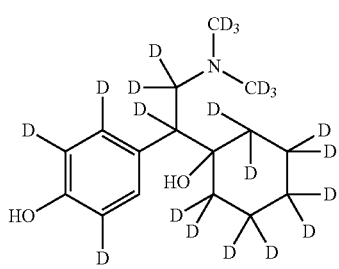
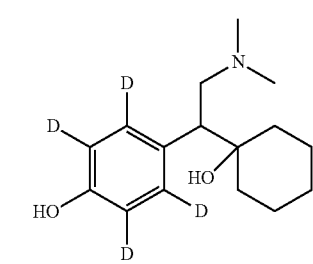
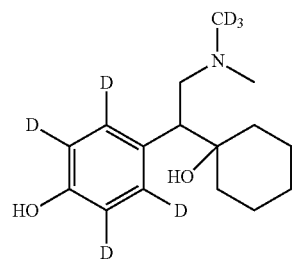
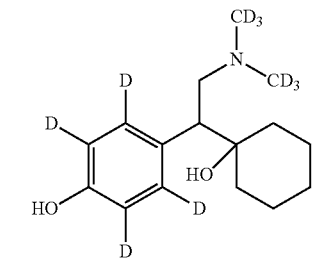
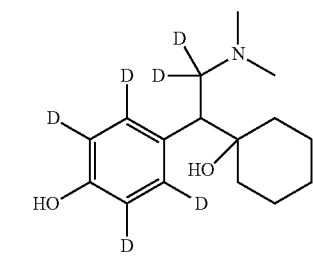

33
-continued
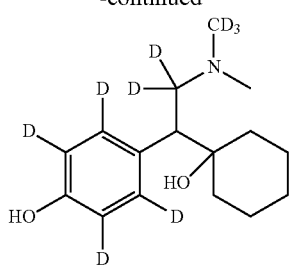
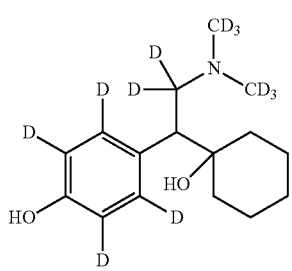
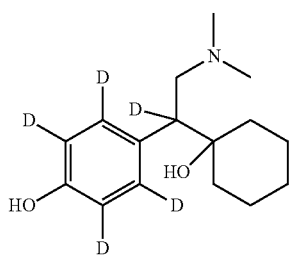
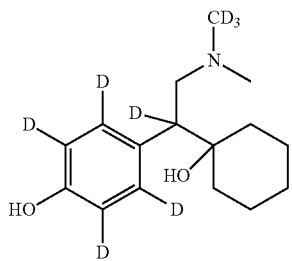
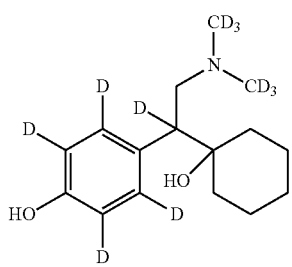
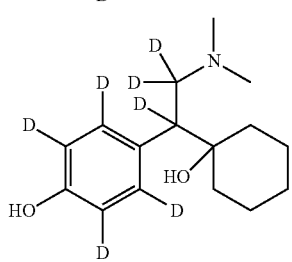
34
-continued
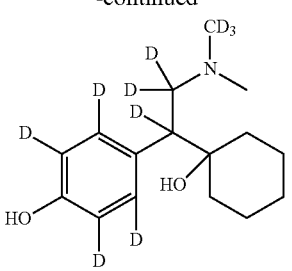
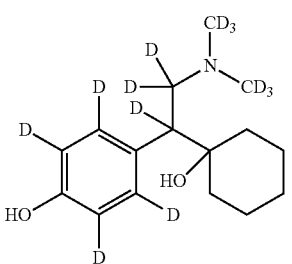
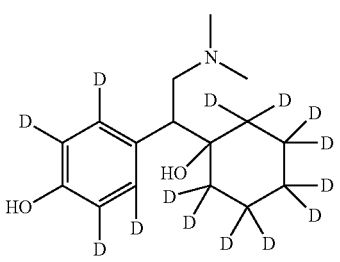
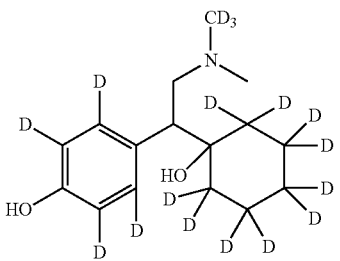
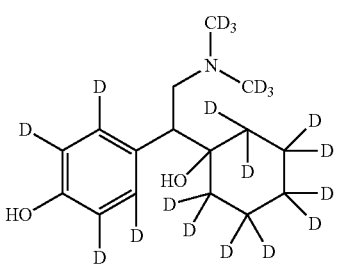
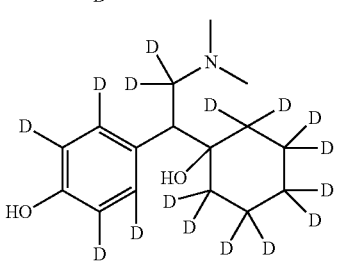

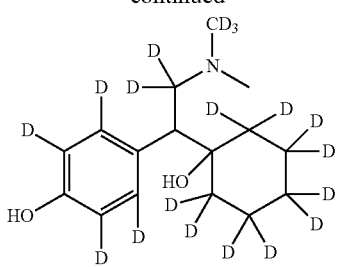

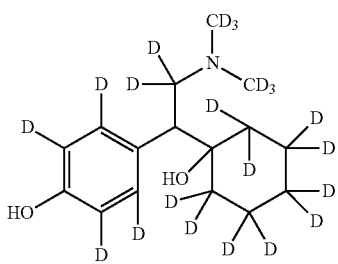

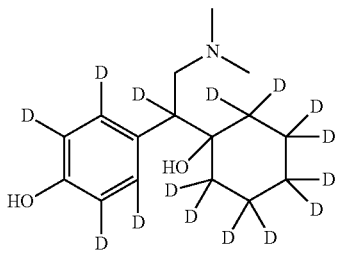

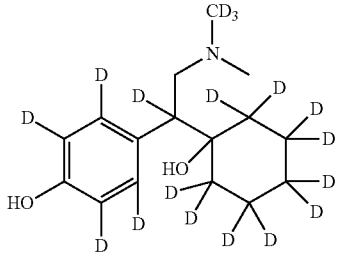

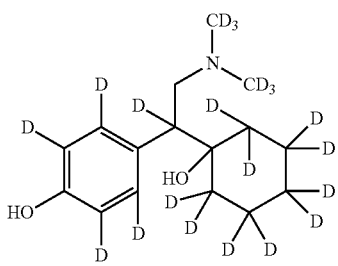

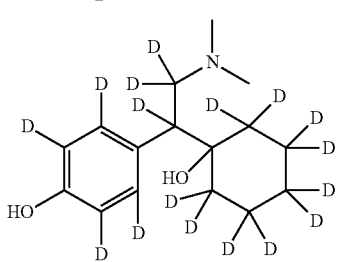

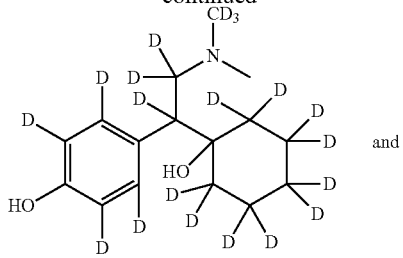

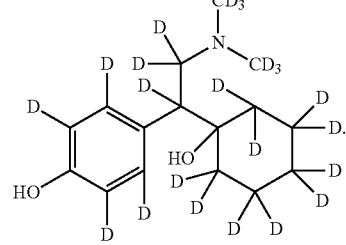

or a pharmaceutically acceptable salt, solvate, or prodrug thereof.

In yet another embodiment, a compound has the structural formula:

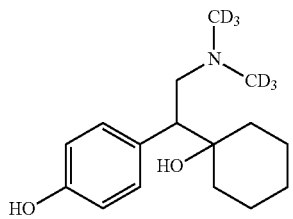 [SMILES: [2H]C([2H])([2H])N(CC(c1ccc(O)cc1)C1(O)CCCCC1)C([2H])([2H])[2H]]

or a pharmaceutically acceptable salt, solvate, or prodrug thereof.

In a further embodiment, said compound contains about 50% or more by weight of the (−)-enantiomer of said compound and about 50% or less by weight of (+)-enantiomer of said compound or about 50% or more by weight of the (+)-enantiomer of said compound and about 50% or less by weight of (−)-enantiomer of said compound.

In another aspect are processes for preparing a compound having structural formula I as serotonin and/or norepinephrine receptor and/or transporter modulators, or other pharmaceutically acceptable derivatives such as prodrug derivatives, or individual isomers and mixture of isomers or enantiomers thereof.

In another embodiment are disclosed processes for preparing a compound having structural formula II, or individual isomers and mixture of isomers or enantiomers thereof.

In another embodiment is provided the use of a compound having structural formula II for the manufacture of a compound having structural formula I.

In one embodiment, disclosed herein is a process for preparing a compound having structural formula I wherein $R_1$-$R_{27}$ are independently selected from the group consisting of hydrogen and deuterium. Such a process can be performed, for example, by reacting a compound having structural formula II, wherein $R_{28}$-$R_{57}$ are independently selected from the group consisting of hydrogen and deuterium, and X is a leaving group anion, under conditions suitable to form a compound having structural formula I, as set forth below:

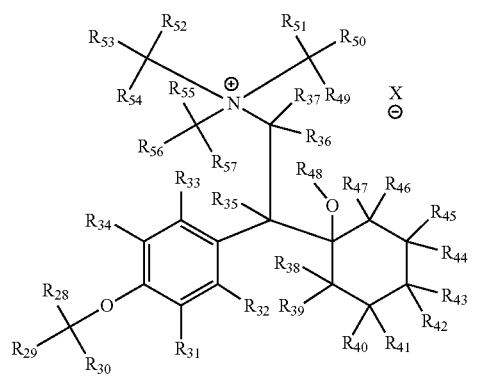

(II)

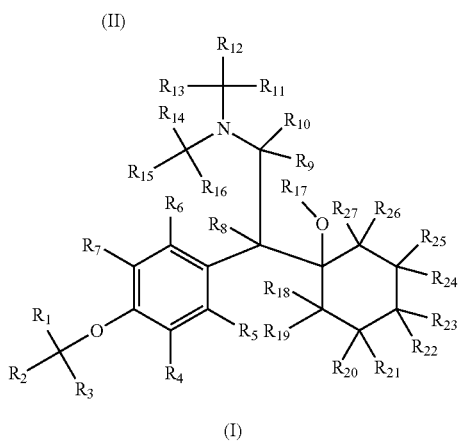

(I)

Compounds having structural formula II can be prepared by methods known to one of skill in the art or following procedures similar to those described in the Example section herein and routine modifications thereof. Compound II is contacted with a nucleophile at an elevated temperature. Nucleophiles contemplated for use in the practice of this particular disclosure include, but are not limited to, 2-aminoethanol, 3-aminopropanol, 1,8-diazabicyclo[5.4.0]undec-7ene, 1,4-diazabicyclo[2.2.2]octane, trialkylamine, sodium borohydride, lithium borohydride, lithium trialkylborohydride, lithium hydride, potassium hydride, and sodium hydride. Solvents contemplated for use in the practice of this particular disclosure include, but are not limited to, polar solvents such as 1,4-dioxane, acetone, acetonitrile, dimethylformamide, dimethylacetamide, N-methylpyrrolidone, dimethyl sulfoxide, or suitable mixtures thereof. The process is carried out at a temperature from about 0° C. to about 500° C., for about 0.01 to about 240 hours, at a pH from about 1 to about 14, at a pressure from about 1 mBar to about 350 Bar.

In certain embodiments, compounds having structural formula II are contacted with a nucleophile at an elevated temperature in the presence of microwave radiation. Nucleophiles contemplated for use in the practice of this particular disclosure include, but are not limited to, 2-aminoethanol, 3-aminopropanol, 1,8-diazabicyclo[5.4.0]undec-7ene, 1,4-diazabicyclo[2.2.2]octane, trialkylamine, sodium borohydride, lithium borohydride, lithium trialkylborohydride, lithium hydride, potassium hydride, and sodium hydride. Solvents contemplated for use in the practice of this particular disclosure include, but are not limited to, polar solvents such as 1,4-dioxane, acetone, acetonitrile, dimethylformamide, dimethylacetamide, N-methylpyrrolidone, dimethyl sulfoxide, or suitable mixtures thereof. The process is carried out in the presence of focused microwave radiation using a quartz reactor at a pressure from about 1 Bar to about 25 Bar, a power setting from about 1 W per liter of solvent to about 900 W per liter of solvent, at a temperature from about 0° C. to about 500° C., for about 0.01 to about 5 hours, at a pH from about 1 to about 14.

In another embodiment is provided the use of a compound having structural formula III for the manufacture of a compound having structural formula I.

In one embodiment, disclosed herein is a process for preparing a compound having structural formula I wherein $R_1$-$R_{27}$ are independently selected from the group consisting of hydrogen and deuterium. Such a process can be performed, for example, by reacting a compound having structural formula III, wherein $R_{58}$-$R_{82}$ are independently selected from the group consisting of hydrogen and deuterium, under conditions suitable to form a compound having structural formula I, as set forth below:

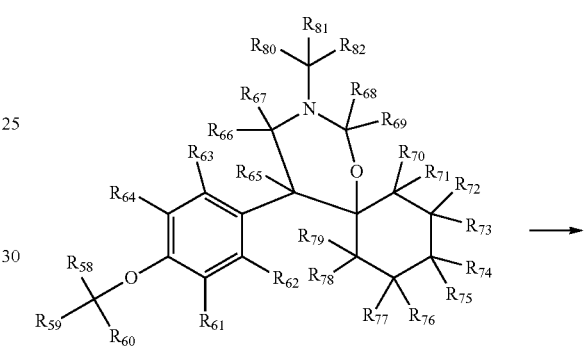

(III)

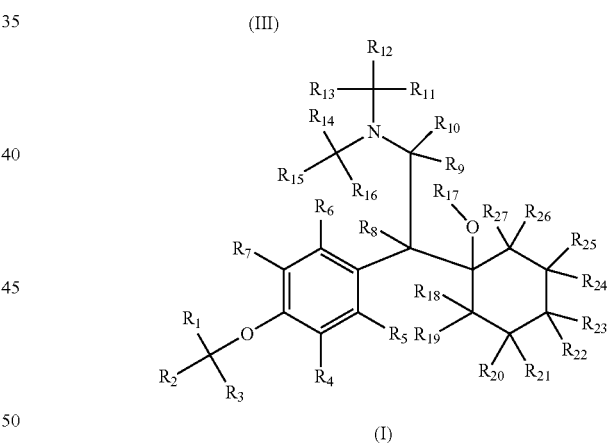

(I)

Compounds having structural formula III can be prepared by methods known to one of skill in the art or following procedures similar to those described in the Example section herein and routine modifications thereof. Compound III is contacted with formic acid or $d_2$-formic acid and an additive at an elevated temperature. Additives contemplated for use in the practice of this particular disclosure include, but are not limited to, lithium deuteroxide, lithium hydroxide, sodium deuteroxide, sodium hydroxide, potassium deuteroxide, potassium hydroxide, lithium formate, potassium formate, and sodium formate. Solvents contemplated for use in the practice of this particular disclosure include, but are not limited to, polar solvents such as water, deuterium oxide, methanol, $d_4$-methanol, formic acid, $d_2$-formic acid, 1,4-dioxane, acetone, acetonitrile, dimethylformamide, dimethylacetamide, N-methylpyrrolidone, dimethyl sulfoxide, or any suitable mixtures thereof. The process is carried out at a temperature from about 0° C. to about 500° C., for about 0.01 to about 240 hours, at a pH from about 1 to about 14, at a pressure from about 1 mBar to about 350 Bar.

In certain embodiments, compounds having structural formula III are contacted with a nucleophile at an elevated temperature in the presence of microwave radiation. Additives contemplated for use in the practice of this particular disclosure include, but are not limited to, lithium deuteroxide, lithium hydroxide, sodium deuteroxide, sodium hydroxide, potassium deuteroxide, potassium hydroxide, lithium formate, potassium formate, and sodium formate. Solvents contemplated for use in the practice of this particular disclosure include, but are not limited to, polar solvents such as water, deuterium oxide, methanol, $d_4$-methanol, formic acid, $d_2$-formic acid, 1,4-dioxane, acetone, acetonitrile, dimethylformamide, dimethylacetamide, N-methylpyrrolidone, dimethyl sulfoxide, or any suitable mixtures thereof. The process is carried out in the presence of focused microwave radiation using a quartz reactor at a pressure from about 1 Bar to about 25 Bar, a power setting from about 1 W per liter of solvent to about 900 W per liter of solvent, at a temperature from about 0° C. to about 500° C., for about 0.01 to about 5 hours, at a pH from about 1 to about 14.

In certain embodiments, a compound as disclosed herein contains about 60% or more by weight of the (−)-enantiomer of the compound and about 40% or less by weight of (+)-enantiomer of the compound. In certain embodiments, a compound as disclosed herein contains about 70% or more by weight of the (−)-enantiomer of the compound and about 30% or less by weight of (+)-enantiomer of the compound. In certain embodiments, a compound as disclosed herein contains about 80% or more by weight of the (−)-enantiomer of the compound and about 20% or less by weight of (+)-enantiomer of the compound. In certain embodiments, a compound as disclosed herein contains about 90% or more by weight of the (−)-enantiomer of the compound and about 10% or less by weight of the (+)-enantiomer of the compound. In certain embodiments, a compound as disclosed herein contains about 95% or more by weight of the (−)-enantiomer of the compound and about 5% or less by weight of (+)-enantiomer of the compound. In certain embodiments, a compound as disclosed herein contains about 99% or more by weight of the (−)-enantiomer of the compound and about 1% or less by weight of (+)-enantiomer of the compound.

The deuterated compounds as disclosed herein may also contain less prevalent isotopes for other elements, including, but not limited to, $^{13}C$ or $^{14}C$ for carbon, $^{33}S$, $^{34}S$, or $^{36}S$ for sulfur, $^{15}N$ for nitrogen, and $^{17}O$ or $^{18}O$ for oxygen.

In certain embodiments, without being bound by any theory, a compound disclosed herein may expose a patient to a maximum of about 0.000005% $D_2O$ or about 0.00001% DHO, assuming that all of the C-D bonds in the compound as disclosed herein are metabolized and released as $D_2O$ or DHO. This quantity is a small fraction of the naturally occurring background levels of $D_2O$ or DHO in circulation. In certain embodiments, the levels of $D_2O$ shown to cause toxicity in animals is much greater than even the maximum limit of exposure because of the deuterium enriched compound as disclosed herein. Thus, in certain embodiments, the deuterium-enriched compound disclosed herein should not cause any additional toxicity because of the use of deuterium.

In one embodiment, the deuterated compounds disclosed herein maintain the beneficial aspects of the corresponding non-isotopically enriched molecules while substantially increasing the maximum tolerated dose, decreasing toxicity, increasing the half-life ($T_{1/2}$), lowering the maximum plasma concentration ($C_{max}$) of the minimum efficacious dose (MED), lowering the efficacious dose and thus decreasing the non-mechanism-related toxicity, and/or lowering the probability of drug-drug interactions.

Isotopic hydrogen can be introduced into a compound as disclosed herein by synthetic techniques that employ deuterated reagents, whereby incorporation rates are pre-determined; and/or by exchange techniques, wherein incorporation rates are determined by equilibrium conditions, and may be highly variable depending on the reaction conditions. Synthetic techniques, where tritium or deuterium is directly and specifically inserted by tritiated or deuterated reagents of known isotopic content, may yield high tritium or deuterium abundance, but can be limited by the chemistry required. Exchange techniques, on the other hand, may yield lower tritium or deuterium incorporation, often with the isotope being distributed over many sites on the molecule.

Compounds having the structural formulae below can be prepared by methods known to one of skill in the art or following procedures similar to those described in the Example section herein and routine modifications thereof. In the Schemes below, deuterated intermediates are either commercially available or can be prepared by methods known to one of skill in the art or following procedures similar to those described in the Example section herein and routine modifications thereof.

For example, a compound having structural formula I can be prepared as shown in Scheme 1.

Scheme 1

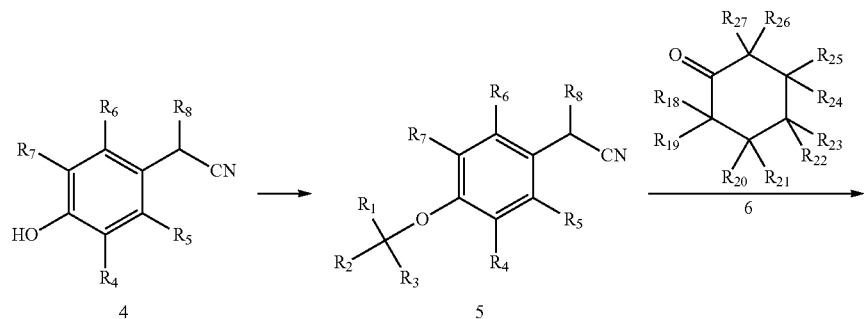

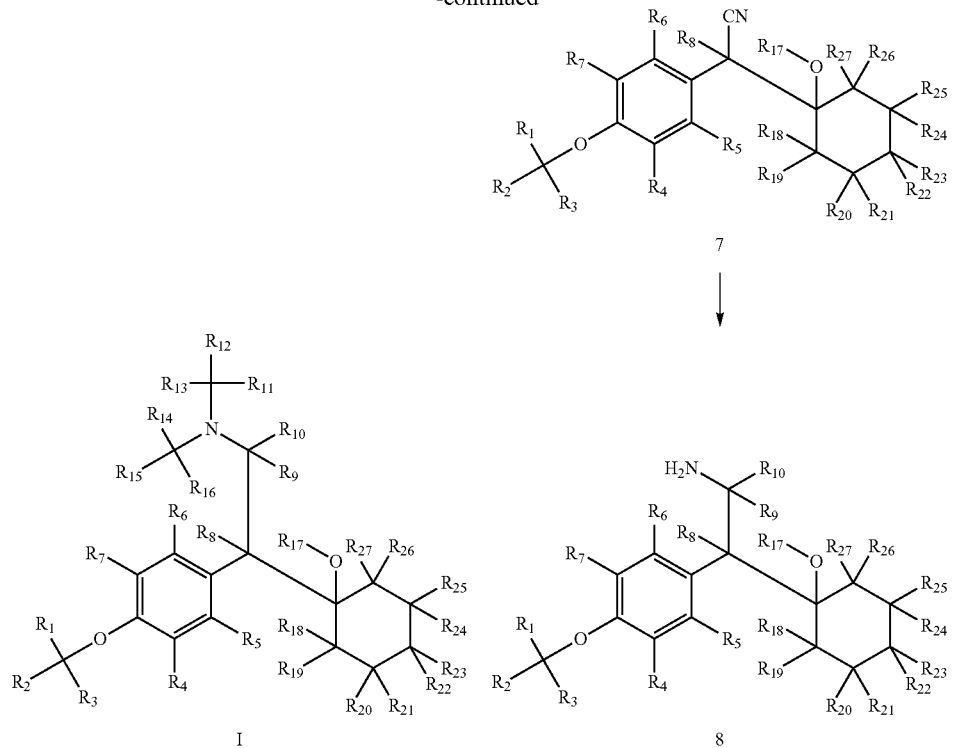

Phenol 4 reacts with methyl iodide and a deprotonating agent, such as potassium carbonate, to give ether 5, which reacts with cyclohexanone 6 in the presence of a deprotonating agent, such as sodium hydroxide, and a phase transfer catalyst, such tetra-n-butyl ammonium hydrogen sulfate, to give nitrile 7. Compound 7 is reduced to aminoalcohol 8 under a hydrogen atmosphere in the presence of a catalyst, such as rhodium on alumina. Alternatively, alcohol 7 is dissolved in ammonia in methanol and reduced to aminoalcohol 8 using a continuous flow hydrogenation reactor equipped with a Raney Ni catalyst cartridge. Compound 8 reacts with excess methyl iodide to give the corresponding quaternary salt II (similar to the reaction step shown in scheme 2) which is demethylated with a nucleophile, such as 2-aminoethanol or 3-aminopropanol, at an elevated temperature to produce the compound of formula I as the free base. The hydrochloride salt of the compound of Formula I can be prepared by methods known in the art.

Deuterium can be incorporated to different positions synthetically, according to the synthetic procedures as shown in Scheme 1, by using appropriate deuterated intermediates. For example, to introduce deuterium at one or more positions selected from $R_1$, $R_2$, $R_3$, $R_{11}$, $R_{12}$, $R_{13}$, $R_{14}$, $R_{15}$, and $R_{16}$, methyl iodide with the corresponding deuterium substitutions can be used.

By way of another example, a compound having structural formula II can be prepared as shown in Scheme 2.

Scheme 2

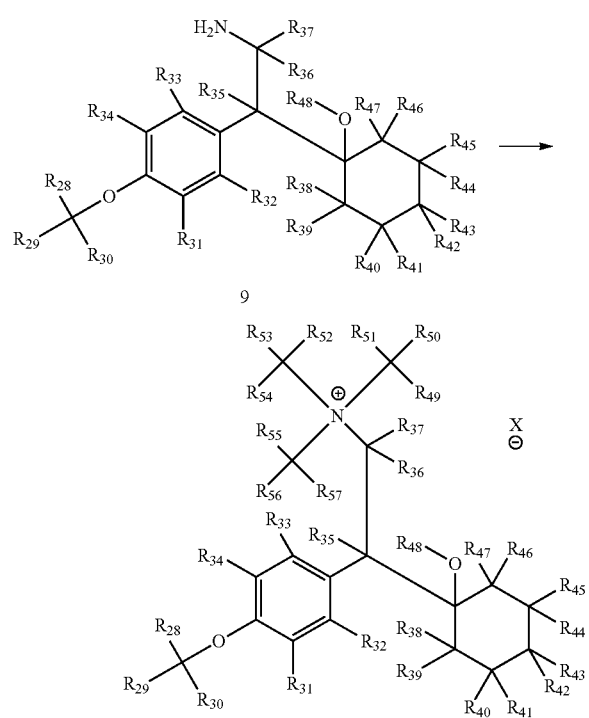

Compound 9 is prepared as in Scheme 1 and reacts with excess methyl iodide to produce the compound of formula II as the iodide salt.

Deuterium can be incorporated to different positions synthetically, according to the synthetic procedures as shown in Scheme 1, by using appropriate deuterated intermediates. For example, to introduce deuterium at one or more positions selected from $R_{28}$, $R_{29}$, $R_{30}$, $R_{49}$, $R_{50}$, $R_{51}$, $R_{52}$, $R_{53}$, $R_{54}$, $R_{55}$, $R_{56}$, and $R_{57}$ methyl iodide with the corresponding deuterium substitutions can be used.

By way of another example, a compound having structural formula III or structural formula I can be prepared as shown in Scheme 3.

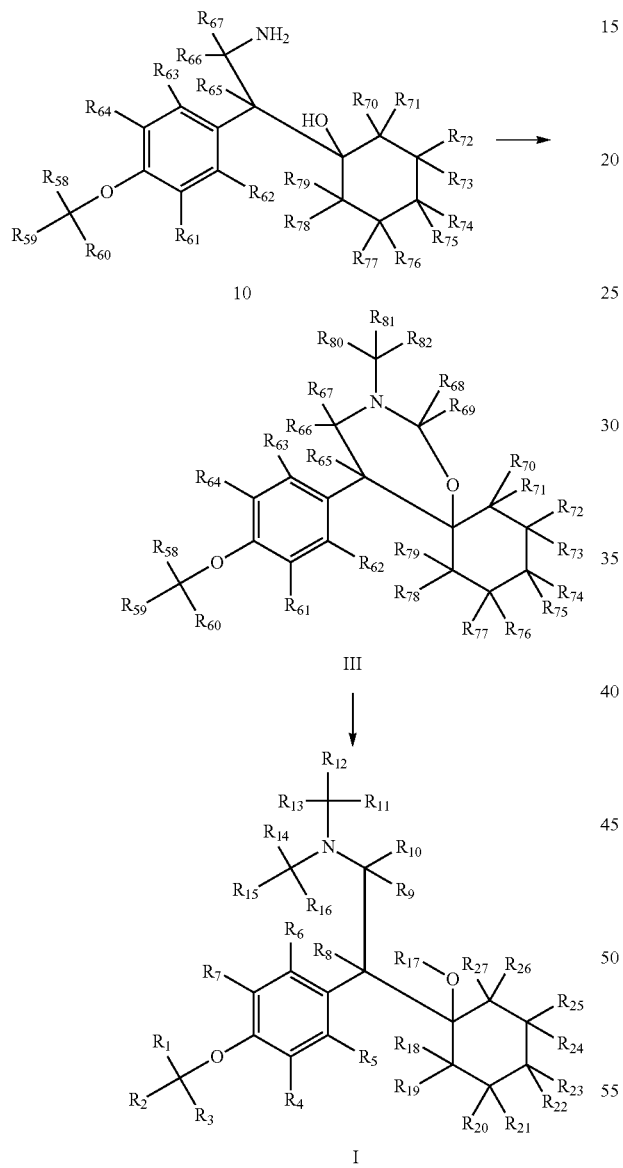

Compound 10 is prepared as in Scheme 1 and reacts with formic acid and formaldehyde at an elevated temperature to produce the compound of formula III. The compound of formula III reacts with formic acid and a deprotonating agent, such as sodium hydroxide or sodium formate, to produce the compound of formula I. The hydrochloride salt of the compound of formula I can be prepared by methods known in the art.

Deuterium can be incorporated to different positions synthetically, according to the synthetic procedures as shown in Scheme 3, by using appropriate deuterated intermediates. For example, to introduce deuterium at one or more positions selected from $R_{68}$, $R_{69}$, $R_{80}$, $R_{81}$, and $R_{82}$, formic acid and formaldehyde with the corresponding deuterium substitutions can be used. To introduce deuterium at one or more positions selected from $R_{58}$, $R_{59}$, and $R_{60}$, methyl iodide with the corresponding deuterium substitutions can be used.

By way of example, a compound having structural formula IV or structural formula can be prepared as shown in Scheme 4.

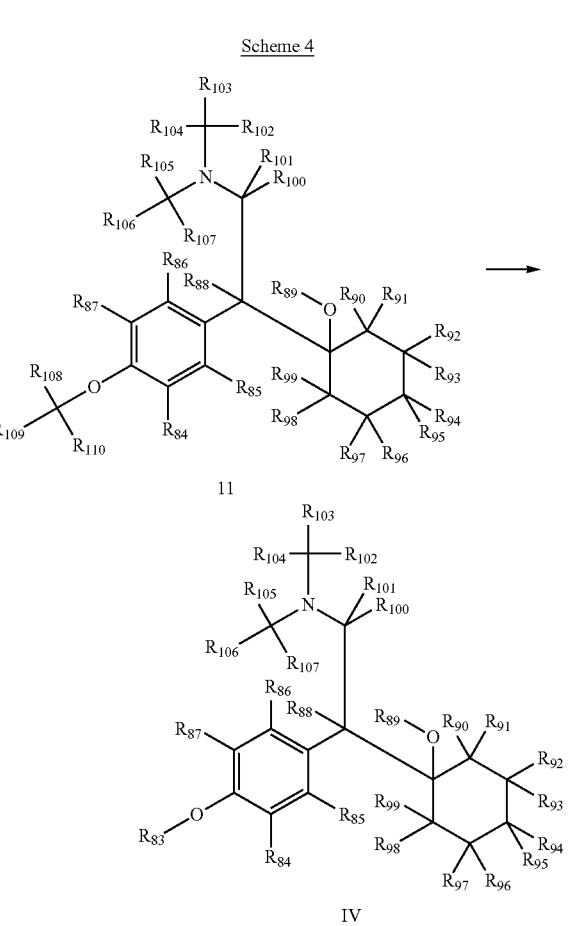

Compound 11 is prepared as in Scheme 1-3 and reacts with a demethylating agent to produce the compound of formula IV.

Deuterium can be incorporated to different positions synthetically, according to the synthetic procedures as shown in Scheme 4, by using appropriate deuterated intermediates as described in Schemes 1-3.

It is to be understood that the compounds disclosed herein may contain one or more chiral centers, chiral axes, and/or chiral planes, as described in "Stereochemistry of Carbon Compounds" Eliel and Wilen, John Wiley & Sons, New York, 1994, pp. 1119-1190. Such chiral centers, chiral axes, and chiral planes may be of either the (R) or (S) configuration, or may be a mixture thereof.

Another method for characterizing a composition containing a compound having at least one chiral center is by the effect of the composition on a beam of polarized light. When a beam of plane polarized light is passed through a solution of a chiral compound, the plane of polarization of the light that emerges is rotated relative to the original plane. This phenomenon is known as optical activity, and compounds that rotate the plane of polarized light are said to be optically active. One enantiomer of a compound will rotate the beam of polarized light in one direction, and the other enantiomer will rotate the beam of light in the opposite direction. The enantiomer that rotates the polarized light in the clockwise direction is the (+) enantiomer and the enantiomer that rotates the polarized light in the counterclockwise direction is the (−) enantiomer. Included within the scope of the compositions described herein are compositions containing between 0 and 100% of the (+) and/or (−) enantiomer of compounds disclosed herein.

Where a compound as disclosed herein contains an alkenyl or alkenylene group, the compound may exist as one or mixture of geometric cis/trans (or Z/E) isomers. Where structural isomers are interconvertible via a low energy barrier, the compound as disclosed herein may exist as a single tautomer or a mixture of tautomers. This can take the form of proton tautomerism in the compound as disclosed herein that contains for example, an imino, keto, or oxime group; or so-called valence tautomerism in the compound that contain an aromatic moiety. It follows that a single compound may exhibit more than one type of isomerism.

The compounds disclosed herein may be enantiomerically pure, such as a single enantiomer or a single diastereomer, or be stereoisomeric mixtures, such as a mixture of enantiomers, a racemic mixture, or a diastereomeric mixture. As such, one of skill in the art will recognize that administration of a compound in its (R) form is equivalent, for compounds that undergo epimerization in vivo, to administration of the compound in its (S) form. Conventional techniques for the preparation/isolation of individual enantiomers include chiral synthesis from a suitable optically pure precursor or resolution of the racemate using, for example, chiral chromatography, recrystallization, resolution, diastereomeric salt formation, or derivatization into diastereomeric adducts followed by separation.

When the compound as disclosed herein contains an acidic or basic moiety, it may also be disclosed as a pharmaceutically acceptable salt (See, Berge et al., *J. Pharm. Sci.* 1977, 66, 1-19; and "Handbook of Pharmaceutical Salts, Properties, and Use," Stah and Wermuth, Ed.; Wiley-VCH and VHCA, Zurich, 2002).

Suitable acids for use in the preparation of pharmaceutically acceptable acid addition salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxo-glutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-aminosalicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable basic addition salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methyl-glucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

The compound as disclosed herein may also be designed as a prodrug, which is a functional derivative of the compound as disclosed herein and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. See Harper, *Progress in Drug Research* 1962, 4, 221-294; Morozowich et al. in "Design of Biopharmaceutical Properties through Prodrugs and Analogs," Roche Ed., APHA Acad. Pharm. Sci. 1977; "Bioreversible Carriers in Drug in Drug Design, Theory and Application," Roche Ed., APHA Acad. Pharm. Sci. 1987; "Design of Prodrugs," Bundgaard, Elsevier, 1985; Wang et al., *Curr. Pharm. Design* 1999, 5, 265-287; Pauletti et al., *Adv. Drug. Delivery Rev.* 1997, 27, 235-256; Mizen et al., *Pharm. Biotech.* 1998, 11, 345-365; Gaignault et al., *Pract. Med. Chem.* 1996, 671-696; Asgharnejad in "Transport Processes in Pharmaceutical Systems," Amidon et al., Ed., Marcell Dekker, 185-218, 2000; Balant et al., *Eur. J. Drug Metab. Pharmacokinet.* 1990, 15, 143-53; Balimane and Sinko, *Adv. Drug Delivery Rev.* 1999, 39, 183-209; Browne, *Clin. Neuropharmacol.* 1997, 20, 1-12; Bundgaard, *Arch. Pharm. Chem.* 1979, 86, 1-39; Bundgaard, *Controlled Drug Delivery* 1987, 17, 179-96; Bundgaard, *Adv. Drug Delivery Rev.* 1992, 8, 1-38; Fleisher et al., *Adv. Drug Delivery Rev.* 1996, 19, 115-130; Fleisher et al., *Methods Enzymol.* 1985, 112, 360-381; Farquhar et al., *J. Pharm. Sci.* 1983, 72, 324-325; Freeman et al., *J. Chem. Soc., Chem. Commun.* 1991, 875-877; Friis and Bundgaard, *Eur. J. Pharm. Sci.* 1996, 4, 49-59; Gangwar et al., *Des. Biopharm. Prop. Prodrugs Analogs,* 1977, 409-421; Nathwani and Wood, *Drugs* 1993, 45, 866-94; Sinhababu and Thakker, *Adv. Drug Delivery Rev.* 1996, 19, 241-273; Stella et al., *Drugs* 1985, 29, 455-73; Tan et al., *Adv. Drug Delivery Rev.* 1999, 39, 117-151; Taylor, *Adv. Drug Delivery Rev.* 1996, 19, 131-148; Valentino and Borchardt, *Drug Discovery Today* 1997, 2, 148-155; Wiebe and Knaus, *Adv. Drug Delivery Rev.* 1999, 39, 63-80; Waller et al., *Br. J. Clin. Pharmac.* 1989, 28, 497-507.

Pharmaceutical Compositions

Disclosed herein are pharmaceutical compositions comprising a compound as disclosed herein as an active ingredient, or a pharmaceutically acceptable salt, solvate, or prodrug thereof, in combination with one or more pharmaceutically acceptable excipients or carriers.

Disclosed herein are pharmaceutical compositions in modified release dosage forms, which comprise a compound as disclosed herein and one or more release controlling excipients or carriers as described herein. Suitable modified release dosage vehicles include, but are not limited to, hydrophilic or hydrophobic matrix devices, water-soluble separating layer coatings, enteric coatings, osmotic devices, multiparticulate devices, and combinations thereof. The pharmaceutical compositions may also comprise non-release controlling excipients or carriers.

Further disclosed herein are pharmaceutical compositions in enteric coated dosage forms, which comprise a compound as disclosed herein and one or more release controlling excipients or carriers for use in an enteric coated dosage form. The pharmaceutical compositions may also comprise non-release controlling excipients or carriers.

Further disclosed herein are pharmaceutical compositions in effervescent dosage forms, which comprise a compound as disclosed herein and one or more release controlling excipients or carriers for use in an effervescent dosage form. The pharmaceutical compositions may also comprise non-release controlling excipients or carriers.

Additionally disclosed are pharmaceutical compositions in a dosage form that has an instant releasing component and at least one delayed releasing component, and is capable of giving a discontinuous release of the compound in the form of at least two consecutive pulses separated in time from 0.1 up to 24 hours. The pharmaceutical compositions comprise a compound as disclosed herein and one or more release controlling and non-release controlling excipients or carriers, such as those excipients or carriers suitable for a disruptable semi-permeable membrane and as swellable substances.

Disclosed herein also are pharmaceutical compositions in a dosage form for oral administration to a subject, which comprise a compound as disclosed herein and one or more pharmaceutically acceptable excipients or carriers, enclosed in an intermediate reactive layer comprising a gastric juice-resistant polymeric layered material partially neutralized with alkali and having cation exchange capacity and a gastric juice-resistant outer layer.

Pharmaceutical compositions are provided herein which comprise about 0.1 to about 1000 mg, about 1 to about 500 mg, about 2 to about 100 mg, about 1 mg, about 2 mg, about 3 mg, about 5 mg, about 10 mg, about 20 mg, about 30 mg, about 40 mg, about 50 mg, about 100 mg, about 500 mg of one or more compounds as disclosed herein.

In certain embodiments, the pharmaceutical compositions are in the form of immediate-release capsules for oral administration, and may further comprise cellulose, iron oxides, lactose, magnesium stearate, and sodium starch glycolate.

In certain embodiments, the pharmaceutical compositions are in the form of delayed-release capsules for oral administration, and may further comprise cellulose, ethylcellulose, gelatin, hypromellose, iron oxide, and titanium dioxide.

In certain embodiments, the pharmaceutical compositions are in the form of enteric coated delayed-release tablets for oral administration, and may further comprise carnauba wax, crospovidone, diacetylated monoglycerides, ethylcellulose, hydroxypropyl cellulose, hypromellose phthalate, magnesium stearate, mannitol, sodium hydroxide, sodium stearyl fumarate, talc, titanium dioxide, and yellow ferric oxide.

In certain embodiments, the pharmaceutical compositions are in the form of enteric coated delayed-release tablets for oral administration, and may further comprise calcium stearate, crospovidone, hydroxypropyl methylcellulose, iron oxide, mannitol, methacrylic acid copolymer, polysorbate 80, povidone, propylene glycol, sodium carbonate, sodium lauryl sulfate, titanium dioxide, and triethyl citrate.

The compound as disclosed herein may be administered alone or in combination with one or more other active ingredients. Pharmaceutical compositions comprising a compound disclosed herein may be formulated in various dosage forms for oral, parenteral, and topical administration. The pharmaceutical compositions may also be formulated as a modified release dosage form, including delayed-, extended-, prolonged-, sustained-, pulsatile-, controlled-, accelerated-, fast-, targeted-, programmed-release, and gastric retention dosage forms. These dosage forms can be prepared according to conventional methods and techniques known to those skilled in the art (see, *Remington: The Science and Practice of Pharmacy*, supra; *Modified-Release Drug Delivery Technology*, Rathbone et al., Eds., Drugs and the Pharmaceutical Science, Marcel Dekker, Inc.: New York, N.Y., 2002; Vol. 126).

The pharmaceutical compositions disclosed herein may be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

In the case wherein the patient's condition does not improve, upon the doctor's discretion the compounds may be administered chronically, that is, for an extended period of time, including throughout the duration of the patient's life in order to ameliorate or otherwise control or limit the symptoms of the patient's disease or condition.

In the case wherein the patient's status does improve, upon the doctor's discretion the compounds may be given continuously or temporarily suspended for a certain length of time (i.e., a "drug holiday").

Once improvement of the patient's conditions has occurred, a maintenance dose is administered if necessary. Subsequently, the dosage or the frequency of administration, or both, can be reduced, as a function of the symptoms, to a level at which the improved disorder is retained. Patients can, however, require intermittent treatment on a long-term basis upon any recurrence of symptoms.

Any of the pharmaceutical formulations described herein can comprise (as the active component) at least one of the hydrochloride salt Forms A-F of formula I, or further contain (as the active component) substantially only one or more of the hydrochloride salt Forms A-F of formula I.

A. Oral Administration

The pharmaceutical compositions disclosed herein may be provided in solid, semisolid, or liquid dosage forms for oral administration. As used herein, oral administration also include buccal, lingual, and sublingual administration. Suitable oral dosage forms include, but are not limited to, tablets, capsules, pills, troches, lozenges, pastilles, cachets, pellets, medicated chewing gum, granules, bulk powders, effervescent or non-effervescent powders or granules, solutions, emulsions, suspensions, solutions, wafers, sprinkles, elixirs, and syrups. In addition to the active ingredient(s), the pharmaceutical compositions may contain one or more pharmaceutically acceptable carriers or excipients, including, but not limited to, binders, fillers, diluents, disintegrants, wetting agents, lubricants, glidants, coloring agents, dye-migration inhibitors, sweetening agents, and flavoring agents.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, Panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The binder or filler may be present from about 50 to about 99% by weight in the pharmaceutical compositions disclosed herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of disintegrant in the pharmaceutical compositions disclosed herein varies upon the type of formulation, and is readily discernible to those of ordinary skill in the art. The pharmaceutical compositions disclosed herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL 200 (W.R. Grace Co., Baltimore, Md.) and CAB-O-SIL® (Cabot Co. of Boston, Mass.); and mixtures thereof. The pharmaceutical compositions disclosed herein may contain about 0.1 to about 5% by weight of a lubricant.

Suitable glidants include colloidal silicon dioxide, CAB-O-SIL® (Cabot Co. of Boston, Mass.), and asbestos-free talc. Coloring agents include any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Flavoring agents include natural flavors extracted from plants, such as fruits, and synthetic blends of compounds which produce a pleasant taste sensation, such as peppermint and methyl salicylate. Sweetening agents include sucrose, lactose, mannitol, syrups, glycerin, and artificial sweeteners, such as saccharin and aspartame. Suitable emulsifying agents include gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suspending and dispersing agents include sodium carboxymethylcellulose, pectin, tragacanth, Veegum, acacia, sodium carbomethylcellulose, hydroxypropyl methylcellulose, and polyvinylpyrrolidone. Preservatives include glycerin, methyl and propylparaben, benzoic add, sodium benzoate and alcohol. Wetting agents include propylene glycol monostearate, sorbitan monooleate, diethylene glycol monolaurate, and polyoxyethylene lauryl ether. Solvents include glycerin, sorbitol, ethyl alcohol, and syrup. Examples of non-aqueous liquids utilized in emulsions include mineral oil and cottonseed oil. Organic acids include citric and tartaric acid. Sources of carbon dioxide include sodium bicarbonate and sodium carbonate.

It should be understood that many carriers and excipients may serve several functions, even within the same formulation.

The pharmaceutical compositions disclosed herein may be disclosed as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenylsalicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms may be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions disclosed herein may be disclosed as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms disclosed herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions disclosed herein may be disclosed in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquids or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde (the term "lower" means an alkyl having between 1 and 6 carbon atoms), e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) disclosed herein, and a dialkylated mono- or polyalkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations may further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions disclosed herein for oral administration may be also disclosed in the forms of liposomes, micelles, microspheres, or nanosystems. Micellar dosage forms can be prepared as described in U.S. Pat. No. 6,350,458.

The pharmaceutical compositions disclosed herein may be disclosed as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions disclosed herein may be co-formulated with other active ingredients which do not impair the desired therapeutic action, or with substances that supplement the desired action, such as drotrecogin-α, and hydrocortisone.

B. Parenteral Administration

The pharmaceutical compositions disclosed herein may be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, and subcutaneous administration.

The pharmaceutical compositions disclosed herein may be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, *Remington: The Science and Practice of Pharmacy*, supra).

The pharmaceutical compositions intended for parenteral administration may include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, dimethylacetamide, and dimethylsulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride, benzethonium chloride, methyl- and propyl-parabens, and sorbic acid.

Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcellulose, hydroxypropyl methylcellulose, and polyvinylpyrrolidone. Suitable emulsifying agents include those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

The pharmaceutical compositions disclosed herein may be formulated for single or multiple dosage administration. The single dosage formulations are packaged in an ampule, a vial, or a syringe. The multiple dosage parenteral formulations must contain an antimicrobial agent at bacteriostatic or fungistatic concentrations. All parenteral formulations must be sterile, as known and practiced in the art.

In one embodiment, the pharmaceutical compositions are disclosed as ready-to-use sterile solutions. In another embodiment, the pharmaceutical compositions are disclosed as sterile dry soluble products, including lyophilized powders and hypodermic tablets, to be reconstituted with a vehicle prior to use. In yet another embodiment, the pharmaceutical compositions are disclosed as ready-to-use sterile suspensions. In yet another embodiment, the pharmaceutical compositions are disclosed as sterile dry insoluble products to be reconstituted with a vehicle prior to use. In still another embodiment, the pharmaceutical compositions are disclosed as ready-to-use sterile emulsions.

The pharmaceutical compositions may be formulated as a suspension, solid, semi-solid, or thixotropic liquid, for administration as an implanted depot. In one embodiment, the pharmaceutical compositions disclosed herein are dispersed in a solid inner matrix, which is surrounded by an outer polymeric membrane that is insoluble in body fluids but allows the active ingredient in the pharmaceutical compositions diffuse through.

Suitable inner matrixes include polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers, such as hydrogels of esters of acrylic and methacrylic acid, collagen, crosslinked polyvinylalcohol, and cross-linked partially hydrolyzed polyvinyl acetate.

Suitable outer polymeric membranes include polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

C. Topical Administration

The pharmaceutical compositions disclosed herein may be administered topically to the skin, orifices, or mucosa. Topical administration, as described herein, includes (intra)dermal, conjunctival, intracorneal, intraocular, ophthalmic, auricular, transdermal, nasal, vaginal, urethral, respiratory, and rectal administration.

The pharmaceutical compositions disclosed herein may be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, dermal patches. The topical formulation of the pharmaceutical compositions disclosed herein may also comprise liposomes, micelles, microspheres, nanosystems, and mixtures thereof.

Pharmaceutically acceptable carriers and excipients suitable for use in the topical formulations disclosed herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryopretectants, lyoprotectants, thickening agents, and inert gases.

The pharmaceutical compositions may also be administered topically by electroporation, iontophoresis, phonophoresis, sonophoresis and microneedle or needle-free injection, such as POWDERJECT™ (Chiron Corp., Emeryville, Calif.), and BIOJECT™ (Bioject Medical Technologies Inc., Tualatin, Oreg.).

The pharmaceutical compositions disclosed herein may be disclosed in the forms of ointments, creams, and gels. Suitable ointment vehicles include oleaginous or hydrocarbon vehicles, including such as lard, benzoinated lard, olive oil, cottonseed oil, and other oils, white petrolatum; emulsifiable or absorption vehicles, such as hydrophilic petrolatum, hydroxystearin sulfate, and anhydrous lanolin; water-removable vehicles, such as hydrophilic ointment; water-soluble ointment vehicles, including polyethylene glycols of varying molecular weight; emulsion vehicles, either water-in-oil (W/O) emulsions or oil-in-water (O/W) emulsions, including cetyl alcohol, glyceryl monostearate, lanolin, and stearic acid (see, *Remington: The Science and Practice of Pharmacy*, supra). These vehicles are emollient but generally require addition of antioxidants and preservatives.

Suitable cream base can be oil-in-water or water-in-oil. Cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout the liquid carrier. Suitable gelling agents include crosslinked acrylic acid polymers, such as carbomers, carboxypolyalkylenes, Carbopol®; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

The pharmaceutical compositions disclosed herein may be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in *Remington: The Science and Practice of Pharmacy*, supra.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature, when formulated with the pharmaceutical compositions disclosed herein; and antioxidants as described herein, including bisulfite and sodium metabisulfite. Suitable vehicles include, but are not limited to, cocoa butter (theobroma oil), glycerin-gelatin, carbowax (polyoxyethylene glycol), spermaceti, paraffin, white and yellow wax, and appropriate mixtures of mono-, di- and triglycerides of fatty acids, hydrogels, such as polyvinyl alcohol, hydroxyethyl methacrylate, polyacrylic acid; glycerinated gelatin. Combinations of the various vehicles may be used. Rectal and vaginal suppositories may be prepared by the compressed method or molding. The typical weight of a rectal and vaginal suppository is about 2 to about 3 g.

The pharmaceutical compositions disclosed herein may be administered ophthalmically in the forms of solutions, suspensions, ointments, emulsions, gel-forming solutions, powders for solutions, gels, ocular inserts, and implants.

The pharmaceutical compositions disclosed herein may be administered intranasally or by inhalation to the respiratory tract. The pharmaceutical compositions may be disclosed in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions may also be disclosed as a dry powder for insufflation, alone or in combination with an inert carrier such as lactose or phospholipids; and nasal drops. For intranasal use, the powder may comprise a bioadhesive agent, including chitosan or cyclodextrin.

Solutions or suspensions for use in a pressurized container, pump, spray, atomizer, or nebulizer may be formulated to contain ethanol, aqueous ethanol, or a suitable alternative agent for dispersing, solubilizing, or extending release of the active ingredient disclosed herein, a propellant as solvent; and/or an surfactant, such as sorbitan trioleate, oleic acid, or an oligolactic acid.

The pharmaceutical compositions disclosed herein may be micronized to a size suitable for delivery by inhalation, such as about 50 micrometers or less, or about 10 micrometers or less. Particles of such sizes may be prepared using a comminuting method known to those skilled in the art, such as spiral jet milling, fluid bed jet milling, supercritical fluid processing to form nanoparticles, high pressure homogenization, or spray drying.

Capsules, blisters and cartridges for use in an inhaler or insufflator may be formulated to contain a powder mix of the pharmaceutical compositions disclosed herein; a suitable powder base, such as lactose or starch; and a performance modifier, such as l-leucine, mannitol, or magnesium stearate. The lactose may be anhydrous or in the form of the monohydrate. Other suitable excipients or carriers include dextran, glucose, maltose, sorbitol, xylitol, fructose, sucrose, and trehalose. The pharmaceutical compositions disclosed herein for inhaled/intranasal administration may further comprise a suitable flavor, such as menthol and levomenthol, or sweeteners, such as saccharin or saccharin sodium.

The pharmaceutical compositions disclosed herein for topical administration may be formulated to be immediate release or modified release, including delayed-, sustained-, pulsed-, controlled-, targeted, and programmed release.

D. Modified Release

The pharmaceutical compositions disclosed herein may be formulated as a modified release dosage form. As used herein, the term "modified release" refers to a dosage form in which the rate or place of release of the active ingredient(s) is different from that of an immediate dosage form when administered by the same route. The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphism of the active ingredient(s).

Examples of modified release include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500.

1. Matrix Controlled Release Devices

The pharmaceutical compositions disclosed herein in a modified release dosage form may be fabricated using a matrix controlled release device known to those skilled in the art (see, Takada et al in "Encyclopedia of Controlled Drug Delivery," Vol. 2, Mathiowitz ed., Wiley, 1999).

In one embodiment, the pharmaceutical compositions disclosed herein in a modified release dosage form is formulated using an erodible matrix device, which is water-swellable, erodible, or soluble polymers, including synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; and cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethylhydroxy ethylcellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®, Rohm America, Inc., Piscataway, N.J.); poly(2-hydroxyethyl-methacrylate); polylactides; copolymers of L-glutamic acid and ethyl-L-glutamate; degradable lactic acid-glycolic acid copolymers; poly-D-(–)-3-hydroxybutyric acid; and other acrylic acid derivatives, such as homopolymers and copolymers of butylmethacrylate, methylmethacrylate, ethylmethacrylate, ethylacrylate, (2-dimethylaminoethyl)methacrylate, and (trimethylaminoethyl)methacrylate chloride.

In further embodiments, the pharmaceutical compositions are formulated with a non-erodible matrix device. The active ingredient(s) is dissolved or dispersed in an inert matrix and is released primarily by diffusion through the inert matrix once administered. Materials suitable for use as a non-erodible matrix device included, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinylacetate copolymers, ethylene/propylene copolymers, ethylene/ethyl acrylate copolymers, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, polyvinyl chloride, plasticized nylon, plasticized polyethyleneterephthalate, natural rubber, silicone rubbers, polydimethylsiloxanes, silicone carbonate copolymers, and; hydrophilic polymers, such as ethyl cellulose, cellulose acetate, crospovidone, and cross-linked partially hydrolyzed polyvinyl acetate, and fatty compounds, such as carnauba wax, microcrystalline wax, and triglycerides.

In a matrix controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients or carriers in the compositions.

The pharmaceutical compositions disclosed herein in a modified release dosage form may be prepared by methods known to those skilled in the art, including direct compression, dry or wet granulation followed by compression, melt-granulation followed by compression.

2. Osmotic Controlled Release Devices

The pharmaceutical compositions disclosed herein in a modified release dosage form may be fabricated using an osmotic controlled release device, including one-chamber system, two-chamber system, asymmetric membrane technology (AMT), and extruding core system (ECS). In general, such devices have at least two components: (a) the core which contains the active ingredient(s); and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents water-swellable hydrophilic polymers, which are also referred to as "osmopolymers" and "hydrogels," including, but not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly(acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents are osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea; and mixtures thereof.

Osmotic agents of different dissolution rates may be employed to influence how rapidly the active ingredient(s) is initially delivered from the dosage form. For example, amorphous sugars, such as Mannogeme EZ (SPI Pharma, Lewes, Del.) can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core may also include a wide variety of other excipients and carriers as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking. Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxylated ethylene-vinylacetate, EC, PEG, PPG, PEG/PPG copolymers, PVP, HEC, HPC, CMC, CMEC, HPMC, HPMCP, HPMCAS, HPMCAT, poly(acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

The delivery port(s) on the semipermeable membrane may be formed post-coating by mechanical or laser drilling. Delivery port(s) may also be formed in situ by erosion of a plug of water-soluble material or by rupture of a thinner portion of the membrane over an indentation in the core. In addition, delivery ports may be formed during coating process, as in the case of asymmetric membrane coatings of the type disclosed in U.S. Pat. Nos. 5,612,059 and 5,698,220.

The total amount of the active ingredient(s) released and the release rate can substantially by modulated via the thickness and porosity of the semipermeable membrane, the composition of the core, and the number, size, and position of the delivery ports.

The pharmaceutical compositions in an osmotic controlled-release dosage form may further comprise additional conventional excipients or carriers as described herein to promote performance or processing of the formulation.

The osmotic controlled-release dosage forms can be prepared according to conventional methods and techniques known to those skilled in the art (see, *Remington: The Science and Practice of Pharmacy*, supra; Santus and Baker, *J. Controlled Release* 1995, 35, 1-21; Verma et al., *Drug Development and Industrial Pharmacy* 2000, 26, 695-708; Verma et al., *J. Controlled Release* 2002, 79, 7-27).

In certain embodiments, the pharmaceutical compositions disclosed herein are formulated as AMT controlled-release dosage form, which comprises an asymmetric osmotic membrane that coats a core comprising the active ingredient(s) and other pharmaceutically acceptable excipients or carriers. See, U.S. Pat. No. 5,612,059 and WO 2002/17918. The AMT controlled-release dosage forms can be prepared according to conventional methods and techniques known to those skilled in the art, including direct compression, dry granulation, wet granulation, and a dip-coating method.

In certain embodiments, the pharmaceutical compositions disclosed herein are formulated as ESC controlled-release dosage form, which comprises an osmotic membrane that coats a core comprising the active ingredient(s), a hydroxylethyl cellulose, and other pharmaceutically acceptable excipients or carriers.

3. Multiparticulate Controlled Release Devices

The pharmaceutical compositions disclosed herein in a modified release dosage form may be fabricated a multiparticulate controlled release device, which comprises a multiplicity of particles, granules, or pellets, ranging from about 10 μm to about 3 mm, about 50 μm to about 2.5 mm, or from about 100 μm to about 1 mm in diameter. Such multiparticulates may be made by the processes know to those skilled in the art, including wet- and dry-granulation, extrusion/spheronization, roller-compaction, melt-congealing, and by spray-coating seed cores. See, for example, *Multiparticulate Oral Drug Delivery*; Marcel Dekker: 1994; and *Pharmaceutical Pelletization Technology*; Marcel Dekker: 1989.

Other excipients or carriers as described herein may be blended with the pharmaceutical compositions to aid in processing and forming the multiparticulates. The resulting particles may themselves constitute the multiparticulate device or may be coated by various film-forming materials, such as enteric polymers, water-swellable, and water-soluble polymers. The multiparticulates can be further processed as a capsule or a tablet.

4. Targeted Delivery

The pharmaceutical compositions disclosed herein may also be formulated to be targeted to a particular tissue, receptor, or other area of the body of the subject to be treated, including liposome-, resealed erythrocyte-, and antibody-based delivery systems. Examples include, but are not limited to, U.S. Pat. Nos. 6,316,652; 6,274,552; 6,271,359; 6,253,872; 6,139,865; 6,131,570; 6,120,751; 6,071,495; 6,060,082; 6,048,736; 6,039,975; 6,004,534; 5,985,307; 5,972,366; 5,900,252; 5,840,674; 5,759,542; and 5,709,874.

Polymorphs of Compounds of Formula I

The hydrochloride salt Forms A-F of the compound of formula I have been characterized using X-ray powder diffractometry. The hydrochloride salt Forms A-F of the compound of Formula I provide X-ray powder diffraction patterns substantially the same as shown in FIGS. 1-6.

The hydrochloride salt Form A of $d_9$-1-[2-dimethylamino-1-(4-methoxyphenyl)-ethyl]cyclohexanol ($d_9$-venlafaxine) of the present disclosure is characterized in that the crystal provides high-intensity diffraction peaks at diffraction angles of 2-theta (2θ) in a X-ray powder diffraction spectrum of about 6.703, 8.321, 12.681, 13.5, 15.54, 18.915, 20.359, 21.161, 21.762, 25.04, and 28.518.

The hydrochloride salt Form B of $d_9$-1-[2-dimethylamino-1-(4-methoxyphenyl)-ethyl]cyclohexanol ($d_9$-venlafaxine) of the present disclosure is characterized in that the crystal provides high-intensity diffraction peaks at diffraction angles of 2-theta (2θ) in a X-ray powder diffraction spectrum of about 6.683, 10.201, 13.441, 15.517, 18.198, 19.719, 20.258, 21.68, 22.668, 25.543, 28.022, and 35.02.

The hydrochloride salt Form C of $d_9$-1-[2-dimethylamino-1-(4-methoxyphenyl)-ethyl]cyclohexanol ($d_9$-venlafaxine) of the present disclosure is characterized in that the crystal provides high-intensity diffraction peaks at diffraction angles of 2-theta (2θ) in a X-ray powder diffraction spectrum of about 6.715, 8.385, 12.68, 13.5, 15.539, 16.282, 18.902, 19.737, 20.34, 21.161, 21.756, 25.02, 25.601, 26.231, 28.518, 31.54, 33.156, 33.637, and 35.158.

The hydrochloride salt Form D of $d_9$-1[2-dimethylamino-1-(4-methoxyphenyl)-ethyl]cyclohexanol ($d_9$-venlafaxine) of the present disclosure is characterized in that the crystal provides high-intensity diffraction peaks at diffraction angles of 2-theta (2θ) in a X-ray powder diffraction spectrum of about 6.74, 7.421, 8.341, 10.219, 12.7, 13.502, 14.9, 15.581, 20.36, 21.221, 21.761, 25.078, 31.04, 34.018, and 35.136.

The hydrochloride salt Form E of $d_9$-1-[2-dimethylamino-1-(4-methoxyphenyl)-ethyl]cyclohexanol ($d_9$-venlafaxine) of the present disclosure is characterized in that the crystal provides high-intensity diffraction peaks at diffraction angles of 2-theta (2θ) in a X-ray powder diffraction spectrum of about 5.527, 7.162, 9.075, 9.567, 11.201, 14.45, 14.76, 16.86, 17.467, 19.201, 19.619, 20.241, 20.65, 21.76, 22.695, 23.05, 24.4, 25.02, 26.519, 26.642, 31.52, and 35.435.

The hydrochloride salt Form F of $d_9$-1-[2-dimethylamino-1-(4-methoxyphenyl)-ethyl]cyclohexanol ($d_9$-venlafaxine) of the present disclosure is characterized in that the crystal provides high-intensity diffraction peaks at diffraction angles of 2-theta (2θ) in a X-ray powder diffraction spectrum of about 5.581, 7.183, 11.22, 14.499, 14.802, 16.662, 19.242, 20.317, 21.728, 22.637, and 35.445.

In the infrared absorption spectra FIGS. 7-12 the horizontal axis shows the wavenumber in cm$^{-1}$ and the vertical axis shows the transmittance in percent (%).

The hydrochloride salt of $d_9$-1-[2-dimethylamino-1-(4-methoxyphenyl)-ethyl]-cyclohexanol ($d_9$-venlafaxine) has been characterized by X-ray powder diffractometry.

The hydrochloride crystals of $d_9$-1-[2-dimethylamino-1-(4-methoxyphenyl)-ethyl]-cyclohexanol ($d_9$-venlafaxine, Forms A-F) provide powder X-ray diffraction spectrums substantially the same as the powder X-ray diffraction spectrums shown in FIGS. 1-6, respectively. However, it is known that a powder X-ray diffraction spectrum may be obtained with a measurement error depending on measurement conditions. In particular, it is generally known that intensities in a powder X-ray diffraction spectrum may fluctuate depending on measurement conditions. Therefore, it should be understood that the salts of the present disclosure are not limited to the crystals that provide X-ray powder diffraction spectrum completely identical to the X-ray powder diffraction spectrums shown in FIGS. 1-6, and that any crystals providing X-ray powder diffraction spectrums substantially the same as the aforementioned X-ray powder diffraction spectrums fall within the scope of the present disclosure. Those skilled in the field of X-ray powder diffractometry can readily judge the substantial identity of X-ray powder diffraction spectrums.

Generally, a measurement error of diffraction angle for a usual X-ray powder diffractometry is about 5% or less, and such degree of a measurement error should be taken into account as to diffraction angles. Furthermore, it should be understood that intensities may fluctuate depending on experimental conditions.

The hydrochloride salt Form A of the compound of formula I is characterized in that the crystal provides high-intensity diffraction peaks at diffraction angles of about 2-theta, [% relative intensity]: 6.703 [29.3], 8.321 [19], 12.681 [77.5], 13.5 [47.9], 15.54 [17.7], 18.915 [24.4], 20.359 [100], 21.161 [38.3], 21.762 [26.1], 25.04 [27.8], and 28.518 [18.2]. The hydrochloride salt Form A of the present disclosure provides an X-ray powder diffraction spectrum substantially the same as the X-ray diffraction spectrum shown in FIG. 1.

The characteristic 2-theta (2θ) values and relative intensity (RI) in percentage for the diffraction spectrum of the hydrochloride salt Form A of the compound of Formula I is shown in Table 1. Thus, described herein is a polymorph of the hydrochloride salt of Formula I having at least four of the most intense peaks presented in Table 1.

TABLE 1

| 2-theta | RI | 2-theta | RI | 2-theta | RI | 2-theta | RI |
| --- | --- | --- | --- | --- | --- | --- | --- |
| 6.703 | 29.3 | 16.762 | 8.1 | 25.04 | 27.8 | 31.539 | 10.5 |
| 7.299 | 9 | 17.315 | 4.6 | 25.34 | 5.3 | 32.428 | 2.1 |
| 8.321 | 19 | 18.5 | 4.2 | 25.641 | 8 | 32.758 | 3.3 |
|  | 2.7 | 18.915 | 24.4 | 26.261 | 6.4 | 33.162 | 7.3 |
| 10.195 | 3.6 | 19.757 | 6.1 | 26.461 | 4.9 | 33.957 | 10.4 |
| 12.681 | 77.5 | 20.359 | 100 | 26.666 | 1.6 | 35.181 | 15.5 |
| 13.5 | 47.9 | 21.161 | 38.3 | 27.265 | 6.7 | 36.024 | 1.8 |
| 14.863 | 9.3 | 21.762 | 26.1 | 28.518 | 18.2 | 36.368 | 1.6 |
| 15.54 | 17.7 | 22.195 | 2 | 28.822 | 6.2 | 36.814 | 2 |
| 15.92 | 3.8 | 22.92 | 2.8 | 30.419 | 2.5 | 37.76 | 3 |
| 16.290 | 11.4 | 24.086 | 1.7 | 31.001 | 7.9 | 38.68 | 5.1 |
|  |  |  |  |  |  | 39.159 | 2.2 |

The hydrochloride salt Form B of the compound of formula I is characterized in that the crystal provides high-intensity diffraction peaks at diffraction angles of about 2-theta, [% relative intensity]: 6.683 [15.5], 10.201 [93.6], 13.441 [27.8], 15.517 [66.2], 18.198 [41], 19.719 [34.1], 20.258 [100], 21.68 [71.2], 22.668 [24.8], 25.543 [22.4], 28.022 [20.9], and 35.02 [33.4]. The hydrochloride salt Form B of the present disclosure provides an x-ray powder diffraction spectrum substantially the same as the X-ray diffraction spectrum shown in FIG. 2.

The characteristic 2-theta (2θ) values and relative intensity (RI) in percentage for the diffraction spectrum of the hydrochloride salt Form B of the compound of formula I is show in Table 2. Thus, described herein is a polymorph of the hydrochloride salt of formula I having a least four of the most intense peaks presented in Table 2.

TABLE 2

| 2-theta | RI |
| --- | --- |
| 6.683 | 15.5 |
| 10.201 | 93.6 |
| 13.441 | 27.8 |
| 15.014 | 7.6 |
| 15.517 | 66.2 |
| 16.458 | 1.5 |
| 16.84 | 10.3 |
| 17.206 | 2.7 |
| 18.198 | 41 |
| 19.719 | 34.1 |
| 20.258 | 100 |
| 21.68 | 71.2 |
| 22.668 | 24.8 |
| 23.923 | 2.7 |
| 25.322 | 9.6 |
| 25.543 | 22.4 |
| 26.502 | 6.7 |
| 27.122 | 9.5 |
| 27.567 | 5.5 |
| 28.022 | 20.9 |
| 28.64 | 4.4 |
| 29.241 | 10.6 |
| 29.650 | 7.1 |
| 31.079 | 11.9 |
| 31.379 | 8.2 |
| 31.978 | 9.1 |
| 32.260 | 10.5 |
| 32.701 | 6.5 |
| 32.961 | 2.3 |
| 34.12 | 9.1 |
| 35.02 | 33.4 |
| 36.024 | 3.1 |
| 36.842 | 2.6 |
| 37.5 | 6.7 |
| 38.341 | 3.9 |
| 38.750 | 1.2 |

The hydrochloride salt Form C of the compound of formula I is characterized in that the crystal provides high-intensity diffraction peaks at diffraction angles of about 2-theta, [% relative intensity]: 6.715 [21.4], 8.385 [20.6], 12.68 [80], 13.5 [40.7], 15.539 [20.2], 16.282 [24.3], 18.902 [48.9], 19.737 [17.4], 20.34 [100], 21.161 [79.4], 21.756 [30.5], 25.02 [31.5], 25.601 [18.9], 26.231 [15.2], 28.518 [30.2], 31.54 [18.7], 33.156 [14.2], 33.637 [16.5], and 35.158 [21.3]. The hydrochloride salt Form C of the present disclosure provides an X-ray powder diffraction spectrum substantially the same as the X-ray diffraction spectrum shown in FIG. 3.

The characteristic 2-theta (2θ) values and relative intensity (RI) in percentage for the diffraction spectrum of the hydrochloride salt Form C of the compound of formula I is shown in Table 3. Thus, described herein is a polymorph of the hydrochloride salt of formula I having at least four of the most intense peaks presented in Table 3.

TABLE 3

| 2-theta | RI | 2-theta | RI | 2-theta | RI | 2-theta | RI |
|---|---|---|---|---|---|---|---|
| 6.715 | 21.4 | 18.162 | 4.2 | 25.36 | 11.1 | 33.156 | 14.2 |
| 8.385 | 20.6 | 18.4 | 3 | 25.601 | 18.9 | 33.637 | 16.5 |
| 10.18 | 9.1 | 18.902 | 48.9 | 26.231 | 15.2 | 35.158 | 21.3 |
| 12.68 | 80 | 19.737 | 17.4 | 26.655 | 3.2 | 36.076 | 3.1 |
| 13.5 | 40.7 | 20.34 | 100 | 27.258 | 8.8 | 36.438 | 2.7 |
| 15.539 | 20.2 | 21.161 | 79.4 | 28.518 | 30.2 | 36.765 | 3.9 |
| 15.68 | 11.5 | 21.756 | 30.5 | 28.636 | 11.6 | 37.66 | 5.6 |
| 15.938 | 9.4 | 22.151 | 3.6 | 30.42 | 2.4 | 38.207 | 2.2 |
| 16.282 | 24.3 | 22.669 | 2.1 | 30.952 | 11.7 | 38.608 | 6.7 |
| 16.878 | 9.9 | 22.955 | 2.4 | 31.54 | 18.7 | 39.795 | 3.6 |
| 16.916 | 9.5 | 24.079 | 1.7 | 32.478 | 4.6 | | |
| 17.302 | 8.2 | 25.02 | 31.5 | 32.775 | 3.9 | | |

The hydrochloride salt Form D of the compound of formula I is characterized in that the crystal provides high-intensity diffraction peaks at diffraction angles of about 2-theta, [% relative intensity]: 6.74 [21.2], 7.421 [14], 8.341 [35.5], 10.219 [23], 12.7 [99.5], 13.502 [40.7], 14.9 [17.5], 15.581 [37.3], 20.36 [100], 21.221 [23.7], 21.761 [41], 25.078 [26.3], 31.04 [17.7], 34.018 [14.8], and 35.136 [22.7]. The hydrochloride salt Form D of the present disclosure provides an X-ray powder diffraction spectrum substantially the same as the X-ray diffraction spectrum shown in FIG. 4.

The characteristic 2-theta (2θ) values and relative intensity (RI) in percentage for the diffraction spectrum of the hydrochloride salt Form D of the compound of formula I is shown in Table 4. Thus, described herein is a polymorph of the hydrochloride salt of formula I having at least four of the most intense peaks presented in Table 4.

TABLE 4

| 2-theta | RI | 2-theta | RI | 2-theta | RI | 2-theta | RI |
|---|---|---|---|---|---|---|---|
| 6.74 | 21.2 | 18.54 | 7.2 | 25.604 | 9.7 | 32.742 | 4 |
| 7.421 | 14 | 18.95 | 12.1 | 26.2 | 6 | 33.237 | 5.4 |
| 8.341 | 35.5 | 19.741 | 12 | 26.461 | 8.9 | 34.018 | 14.8 |
| 10.219 | 23 | 20.36 | 100 | 26.668 | 6.9 | 35.136 | 22.7 |
| 12.7 | 99.5 | 21.221 | 23.7 | 27.258 | 7.1 | 36.1 | 2.5 |
| 13.502 | 40.7 | 21.761 | 41 | 28.223 | 7.3 | 36.355 | 1.8 |
| 14.9 | 17.5 | 22.279 | 2.2 | 28.516 | 11.9 | 36.639 | 2.2 |
| 15.581 | 37.3 | 22.719 | 4.9 | 28.916 | 4.8 | 37.719 | 3.5 |
| 16.361 | 9.9 | 23.008 | 3 | 29.322 | 3.2 | 38.581 | 5.5 |
| 16.764 | 13 | 24.024 | 3.2 | 30.419 | 3.2 | 39.195 | 3.8 |
| 17.424 | 3 | 25.078 | 26.3 | 31.04 | 17.7 | | |
| 18.276 | 10.2 | 25.388 | 5.9 | 31.66 | 10.6 | | |

The hydrochloride salt Form E of the compound of formula I is characterized in that the crystal provides high-intensity diffraction peaks at diffraction angles of about 2-theta, [% relative intensity]: 5.527 [28], 7.162 [36.2], 9.075 [24.1], 9.567 [14.9], 11.201 [100], 14.45 [40.2], 14.76 [40.4], 16.86 [71.7], 17.467 [15.7], 19.201 [66.5], 19.619 [19.6], 20.241 [35.2], 20.65 [19.6], 21.76 [22.5], 22.695 [26.4], 23.05 [13.2], 24.4 [15.3], 25.02 [12.1], 26.519 [13.5], 26.642 [18.7], 31.52 [12.6], and 35.435 [17.9]. The hydrochloride salt Form E of the present disclosure provides an X-ray powder diffraction spectrum substantially the same as the X-ray diffraction spectrum shown in FIG. 5.

The characteristic 2-theta (2°) values and relative intensity (RI) in percentage for the diffraction spectrum of the hydrochloride salt Form E of the compound of formula I is shown in Table 5. Thus, described herein is a polymorph of the hydrochloride salt of formula I having at least four of the most intense peaks presented in Table 5.

TABLE 5

| 2-theta | RI | 2-theta | RI | 2-theta | RI | 2-theta | RI |
|---|---|---|---|---|---|---|---|
| 5.527 | 28 | 15.721 | 11.2 | 23.05 | 13.2 | 30.98 | 7.7 |
| 7.162 | 36.2 | 16.041 | 8.4 | 23.994 | 2 | 31.52 | 12.6 |
| 9.075 | 24.1 | 16.86 | 71.7 | 24.4 | 15.3 | 32.362 | 6.4 |
| 9.567 | 14.9 | 17.467 | 15.7 | 25.02 | 12.1 | 32.721 | 6 |
| 10.663 | 9 | 17.866 | 3 | 25.643 | 3.9 | 33.162 | 2.1 |
| 11.201 | 100 | 18.368 | 12.8 | 25.861 | 6.7 | 34.461 | 9.6 |
| 12.104 | 2.4 | 19.201 | 66.5 | 26.519 | 13.5 | 35.435 | 17.9 |
| 12.361 | 1.2 | 19.619 | 19.6 | 26.642 | 18.7 | 35.899 | 5.6 |
| 13.422 | 2.1 | 20.241 | 35.2 | 27.502 | 5.1 | 36.779 | 4.7 |
| 13.921 | 4.4 | 20.65 | 19.6 | 28.422 | 6.1 | 37.4 | 4.5 |
| 14.45 | 40.2 | 20.678 | 11.2 | 28.858 | 7.2 | 37.564 | 2 |
| 14.76 | 40.4 | 21.76 | 22.5 | 29.937 | 3.1 | 38.962 | 3.6 |
| 15.366 | 3.2 | 22.695 | 26.4 | 39.786 | | | |

The hydrochloride salt Form F of the compound of formula I is characterized in that the crystal provides high-intensity diffraction peaks at diffraction angles of about 2-theta, [% relative intensity]: 5.581 [26.1], 7.183 [18.3], 11.22 [100], 14.499 [18.8], 14.802 [20.5], 16.662 [63.9], 19.242 [38.4], 20.317 [51.6], 21.728 [17.5], 22.637 [26.3], and 35.445 [16.2]. The hydrochloride salt Form F of the present disclosure provides an X-ray powder diffraction spectrum substantially the same as the X-ray diffraction spectrum shown in FIG. 6.

The characteristic 2-theta (2θ) values and relative intensity (RI) in percentage for the diffraction spectrum of the hydrochloride salt Form F of the compound of formula I is shown in Table 6. Thus, described herein is a polymorph of the hydrochloride salt of formula I having at least 4 of the most intense peaks presented in Table 6.

TABLE 6

| 2-theta | RI | 2-theta | RI | 2-theta | RI | 2-theta | RI |
|---|---|---|---|---|---|---|---|
| 5.581 | 26.1 | 15.599 | 5.1 | 23.101 | 9 | 31.597 | 9.1 |
| 6.605 | 6.4 | 15.798 | 6.1 | 24.425 | 11.9 | 32.374 | 1.6 |
| 7.183 | 18.3 | 16.087 | 3.6 | 25.042 | 7.1 | 33.32 | 1.3 |
| 9.079 | 7.7 | 16.662 | 63.9 | 25.921 | 7.7 | 34.524 | 6.3 |
| 9.576 | 9.1 | 17.519 | 10.6 | 26.537 | 5.4 | 35.112 | 4.7 |
| 10.206 | 2.4 | 18.407 | 5.6 | 26.939 | 10.1 | 35.445 | 16.2 |
| 10.735 | 4.4 | 19.242 | 38.4 | 27.194 | 5.3 | 35.660 | 1.3 |
| 11.22 | 100 | 19.66 | 11.8 | 27.578 | 2.5 | 36.727 | 2.3 |
| 12.133 | 3 | 20.317 | 51.6 | 28.243 | 3.9 | 36.961 | 3.2 |
| 13.447 | 9 | 20.67 | 8.8 | 28.921 | 3.5 | 37.464 | 2.9 |
| 13.963 | 2.2 | 20.923 | 6.3 | 29.4 | 1.6 | 38.023 | 1.9 |
| 14.499 | 18.8 | 21.728 | 17.5 | 29.808 | 2.6 | 39.777 | 3.6 |
| 14.802 | 20.5 | 22.637 | 26.3 | 31.064 | 3.7 | | |

X-ray powder diffraction pattern is only one of many ways to characterize the arrangement of atoms comprising the hydrochloride salt of $d_9$-1-[2-dimethylamino-1-(4-methoxyphenyl)-ethyl]-cyclohexanol ($d_9$-venlafaxine, Forms A-F). Other methods are well known in the art, such as, single X-ray crystal diffraction, may be used to identify aforementioned salt forms of compounds of formula I.

The hydrochloride salt Forms A-F of the compound of formula I have high crystallinity, i.e., substantially free of amorphous material. Such salts provide more reproducible dosing results. The hydrochloride salt Forms A-F of the compound of formula I are substantially hygroscopically stable, which alleviates potential problems associated with weight changes of the active ingredient during the manufacture of capsules or tablets. The hydrochloride Forms A-F of the compound of formula I also have a low tendency for concentrated aqueous solution to form viscous mixtures upon standing. The hydrochloride salt Forms A-F of the compound of formula I have rapid kinetic aqueous solubility which simplifies aqueous dosing and make them suitable for injectable dosage forms. Furthermore, the hydrochloride salt Forms A-F of the compound of formula I with enhanced solubility characteristics facilitate the dissolution of solid dosage forms in a timely manner.

The hydrochloride salt Forms A-F of the compound of formula I have greater kinetic solubility than the free base of the compound of formula I. Additionally, the hydrochloride salt Forms A-F of the compound of formula I are more stable in air and can be used without deliquescence.

Methods of Use

Disclosed are methods for treating a monoamine-related disorder, comprising administering to a subject having or being suspected to have such a disorder, a therapeutically effective amount compound as disclosed herein or a pharmaceutically acceptable salt, solvate, or prodrug thereof.

Monoamine-mediated disorders include, but are not limited to, psychotropic disorders, anxiety disorder, generalized anxiety disorder, depression, post-traumatic stress disorder, obsessive-compulsive disorder, panic disorder, hot flashes, senile dementia, migraine, hepatopulmonary syndrome, chronic pain, nociceptive pain, neuropathic pain, painful diabetic retinopathy, bipolar depression, obstructive sleep apnea, psychiatric disorders, premenstrual dysphoric disorder, social phobia, social anxiety disorder, urinary incontinence, anorexia, bulimia nervosa, obesity, ischemia, head injury, calcium overload in brain cells, drug dependence, Gilles de la Tourette syndrome, Shy Drager syndrome, vasomotor flushing, chronic fatigue syndrome, cognition enhancement, attention deficit hyperactivity disorder, fibromyalgia, irritable bowel syndrome, and/or premature ejaculation.

Also disclosed are methods of treating, preventing, or ameliorating one or more symptoms of a disorder associated with serotonin and/or norepinephrine receptors and/or transporters, by administering to a subject having or being suspected to have such a disorder a therapeutically effective amount of a compound as disclosed herein or a pharmaceutically acceptable salt, solvate, or prodrug thereof.

Furthermore, disclosed herein are methods of modulating the activity of serotonin and/or norepinephrine receptors and/or transporters, comprising contacting the receptors with at least one compound as disclosed herein or a pharmaceutically acceptable salt, solvate, or prodrug thereof. In one embodiment, the serotonin and/or norepinephrine receptor and/or transporter is expressed by a cell.

In certain embodiments, the inter-individual variation in plasma levels of the compounds as disclosed herein, or metabolites thereof, is decreased as defined herein.

Disclosed herein are methods for treating a subject, including a human, having or suspected of having a disorder comprising administering to the subject a therapeutically effective amount of a compound as disclosed herein or a pharmaceutically acceptable salt, solvate, or prodrug thereof; so as to affect increased average plasma levels of the compound or decreased average plasma levels of at least one metabolite of the compound per dosage unit as compared to the corresponding non-isotopically enriched compound.

In certain embodiments, the average plasma levels of the compounds as disclosed herein are increased as defined herein.

In certain embodiments, the average plasma levels of a metabolite of the compounds as disclosed herein are decreased as defined herein.

Plasma levels of the compounds as disclosed herein, or metabolites thereof, are measured using the methods described by Li et al. (*Rapid Communications in Mass Spectrometry* 2005, 19, 1943-1950).

Disclosed herein are methods for treating a subject, including a human, having or suspected of having a disorder comprising administering to the subject a therapeutically effective amount of a compound as disclosed herein or a pharmaceutically acceptable salt, solvate, or prodrug thereof; so as to affect a decreased inhibition of, and/or metabolism by at least one cytochrome P450 or monoamine oxidase isoform in the subject during the treatment of the disease as compared to the corresponding non-isotopically enriched compound.

Examples of cytochrome $P_{450}$ isoforms in a mammalian subject include, but are not limited to, CYP1A1, CYP1A2, CYP1B1, CYP2A6, CYP2A13, CYP2B6, CYP2C8, CYP2C9, CYP2C18, CYP2C19, CYP2D6, CYP2E1, CYP2G1, CYP2J2, CYP2R$_1$, CYP2S1, CYP3A4, CYP3A5, CYP3A5P1, CYP3A5P2, CYP3A7, CYP4A11, CYP4B1, CYP4F2, CYP4F3, CYP4F8, CYP4F11, CYP4F12, CYP4X1, CYP4Z1, CYP5A1, CYP7A1, CYP7B1, CYP8A1, CYP8B1, CYP11A1, CYP11B1, CYP11B2, CYP17, CYP19, CYP21, CYP24, CYP26A1, CYP26B1, CYP27A1, CYP27B1, CYP39, CYP46, and CYP51.

Examples of monoamine oxidase isoforms in a mammalian subject include, but are not limited to, $MAO_A$, and $MAO_B$.

In certain embodiments, the decrease in inhibition of the cytochrome $P_{450}$ or monoamine oxidase isoform by a compound as disclosed herein is greater than about 5%, greater than about 10%, greater than about 20%, greater than about 30%, greater than about 40%, or greater than about 50% as compared to the corresponding non-isotopically enriched compounds.

The inhibition of the cytochrome $P_{450}$ isoform is measured by the method of Ko et al. (*British Journal of Clinical Pharmacology*, 2000, 49, 343-351). The inhibition of the $MAO_A$ isoform is measured by the method of Weyler et al. (*J. Biol Chem.* 1985, 260, 13199-13207). The inhibition of the $MAO_B$ isoform is measured by the method of Uebelhack et al. (*Pharmacopsychiatry*, 1998, 31, 187-192).

Disclosed herein are methods for treating a subject, including a human, having or suspected of having a disorder comprising administering to the subject a therapeutically effective amount of a compound as disclosed herein or a pharmaceutically acceptable salt, solvate, or prodrug thereof; so as to affect a decreased metabolism via at least one polymorphically-expressed cytochrome P450 isoform in the subject during the treatment of the disease as compared to the corresponding non-isotopically enriched compound.

Examples of polymorphically-expressed cytochrome $P_{450}$ isoforms in a mammalian subject include, but are not limited to, CYP2C8, CYP2C9, CYP2C19, and CYP2D6.

In certain embodiments, the decrease in metabolism of the compound as disclosed herein by at least one polymorphically-expressed cytochrome $P_{450}$ isoforms cytochrome $P_{450}$ isoform is greater than about 5%, greater than about 10%, greater than about 20%, greater than about 30%, greater than about 40%, or greater than about 50% as compared to the corresponding non-isotopically enriched compound.

The metabolic activities of liver microsomes and the cytochrome $P_{450}$ isoforms are measured by the methods described in Examples 41 and 42. The metabolic activities of the monoamine oxidase isoforms are measured by the methods described in Examples 42 and 43.

Disclosed herein are methods for treating a subject, including a human, having or suspected of having a disorder comprising administering to the subject a therapeutically effective amount of a compound as disclosed herein or a pharmaceutically acceptable salt, solvate, or prodrug thereof; so as to affect at least one statistically-significantly improved disorder-control and/or disorder-eradication endpoint as compared to the corresponding non-isotopically enriched compound. Examples of improved disorder-control and/or disorder-eradication endpoints include, but are not limited to, statistically-significant improvement of pain indices, depression indices, and/or diminution of hepatotoxicity, as compared to the corresponding non-isotopically enriched compound.

Disclosed herein are methods for treating a subject, including a human, having or suspected of having a disorder comprising administering to the subject a therapeutically effective amount of a compound as disclosed herein or a pharmaceutically acceptable salt, solvate, or prodrug thereof; so as to affect an improved clinical effect as compared to the corresponding non-isotopically enriched compound. Examples of improved clinical effects include, but are not limited to, statistically-significant improvement of pain indices, perfusion of ischemic tissues with oxygen, prevention of ischemia, entheogenic effects sufficient to facilitate psychotherapy, cataleptic effects sufficient to enable medical treatment of a non-compliant trauma victim, neuroprotection during an ischemic event, and/or diminution of hepatotoxicity, as compared to the corresponding non-isotopically enriched compound.

Disclosed herein are methods for treating a subject, including a human, having or suspected of having a disorder comprising administering to the subject a therapeutically effective amount of a compound as disclosed herein or a pharmaceutically acceptable salt, solvate, or prodrug thereof; so as to affect prevention of recurrence, or delay of decline or appearance, of abnormal alimentary or hepatic parameters as the primary clinical benefit, as compared to the corresponding non-isotopically enriched compound.

Disclosed herein are methods for treating a subject, including a human, having or suspected of having a disorder comprising administering to the subject a therapeutically effective amount of a compound as disclosed herein or a pharmaceutically acceptable salt, solvate, or prodrug thereof; so as to allow the treatment while reducing or eliminating deleterious changes in any diagnostic hepatobiliary function endpoints as compared to the corresponding nonisotopically enriched compound.

Examples of diagnostic hepatobiliary function endpoints include, but are not limited to, alanine aminotransferase ("ALT"), serum glutamic-pyruvic transaminase ("SGPT"), aspartate aminotransferase ("AST" or "SGOT"), ALT/AST ratios, serum aldolase, alkaline phosphatase ("ALP"), ammonia levels, bilirubin, gamma-glutamyl transpeptidase ("GGTP," "γ-GTP," or "GGT"), leucine aminopeptidase ("LAP"), liver biopsy, liver ultrasonography, liver nuclear scan, 5'-nucleotidase, and blood protein. Hepatobiliary endpoints are compared to the stated normal levels as given in "Diagnostic and Laboratory Test Reference", 4$^{th}$ edition, Mosby, 1999. These assays are run by accredited laboratories according to standard protocol.

Depending on the disease to be treated and the subject's condition, the compound of Formula I provided herein may be administered by oral, parenteral (e.g., intramuscular, intraperitoneal, intravenous, ICV, intracisternal injection or infusion, subcutaneous injection, or implant), inhalation, nasal, vaginal, rectal, sublingual, or topical (e.g., transdermal or local) routes of administration, and may be formulated, alone or together, in suitable dosage unit with pharmaceutically acceptable carriers, adjuvants and vehicles appropriate for each route of administration.

The dose may be in the form of one, two, three, four, five, six, or more sub-doses that are administered at appropriate intervals per day. The dose or sub-doses can be administered in the form of dosage units containing from about 0.1 to about 1000 milligram, from about 0.1 to about 500 milligrams, or from 0.5 about to about 100 milligrams of active ingredient(s) per dosage unit, and if the condition of the patient requires, the dose can, by way of alternative, be administered as a continuous infusion.

In certain embodiments, an appropriate dosage level is about 0.01 to about 100 mg per kg patient body weight per day (mg/kg per day), about 0.01 to about 50 mg/kg per day, about 0.01 to about 25 mg/kg per day, or about 0.05 to about 10 mg/kg per day, which may be administered in single or multiple doses. A suitable dosage level may be about 0.01 to about 100 mg/kg per day, about 0.05 to about 50 mg/kg per day, or about 0.1 to about 10 mg/kg per day. Within this range the dosage may be about 0.01 to about 0.1, about 0.1 to about 1.0, about 1.0 to about 10, or about 10 to about 50 mg/kg per day.

Combination Therapy

The a compound as disclosed herein or pharmaceutically acceptable salts, solvates, or prodrugs thereof may also be combined or used in combination with other agents useful in the treatment, prevention, or amelioration of one or more symptoms of the disorders for which the compound provided herein are useful. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced).

Such other agents, adjuvants, or drugs, may be administered, by a route and in an amount commonly used therefor, simultaneously or sequentially with a compound as disclosed herein or a pharmaceutically acceptable salt, solvate, or prodrug thereof. When a pharmaceutically acceptable salt of a compound as disclosed herein is used contemporaneously with one or more other drugs, a pharmaceutical composition containing such other drugs in addition to the compound disclosed herein may be utilized, but is not required. Accordingly, the pharmaceutical compositions disclosed herein include those that also contain one or more other active ingredients or therapeutic agents, in addition to the compound provided herein.

In certain embodiments, the compounds disclosed herein can be combined with one or more modulators of NMDA-receptors known in the art, including, but not limited to, phencyclidine (PCP), amantadine, ibogaine, memantine, dextrorphan, ketamine, nitrous oxide, and dextromethorphan.

In certain embodiments, the compounds provided herein can be combined with one or more natural, semisynthetic, or fully synthetic opioids known in the art, including, but not limited to, morphine, codeine, thebain, diacetylmorphine, oxycodone, hydrocodone, hydromorphone, oxymorphone, nicomorphine, fentanyl, α-methylfentanyl, alfentanil, sufentanil, remifentanyl, carfentanyl, ohmefentanyl, pethidine, ketobemidone, propoxyphene, dextropropoxyphene, methadone, loperamide, pentazocine, buprenorphine, etorphine, butorphanol, nalbufine, levorphanol, naloxone, naltrexone, and tramadol.

In certain embodiments, the compounds disclosed herein can be combined with one or more opioid antagonists known in the art, including, but not limited to, nalmefene, naltrexone, and naloxone.

In certain embodiments, the compounds disclosed herein can be combined with one or more local and/or general anesthetics and sedatives known in the art, including, but not limited to, propofol, procaine, lidocaine, prilocaine, bupivicaine, levobupivicaine, nitrous oxide, halothane, enflurane, isoflurane, sevoflurane, desflurane, thiopental, methohexital, etomidate, diazepam, midazolam, lorazepam, succinylcholine, vecuronium, rocuronium, pipecuronium, rapacuronium, tubocurarine, and gallamine.

The compounds disclosed herein can also be administered in combination with other classes of compounds, including, but not limited to, endothelin converting enzyme (ECE) inhibitors, such as phosphoramidon; thromboxane receptor antagonists, such as ifetroban; potassium channel openers; thrombin inhibitors, such as hirudin; growth factor inhibitors, such as modulators of PDGF activity; platelet activating factor (PAF) antagonists; anti-platelet agents, such as GPIIb/IIIa blockers (e.g., abdximab, eptifibatide, and tirofiban), P2Y(AC) antagonists (e.g., clopidogrel, ticlopidine and CS-747), and aspirin; anticoagulants, such as warfarin; low molecular weight heparins, such as enoxaparin; Factor VIIa Inhibitors and Factor Xa Inhibitors; renin inhibitors; neutral endopeptidase (NEP) inhibitors; vasopepsidase inhibitors (dual NEP-ACE inhibitors), such as omapatrilat and gemopatrilat; HMG CoA reductase inhibitors, such as pravastatin, lovastatin, atorvastatin, simvastatin, NK-104 (a.k.a. itavastatin, nisvastatin, or nisbastatin), and ZD-4522 (also known as rosuvastatin, or atavastatin or visastatin); squalene synthetase inhibitors; fibrates; bile acid sequestrants, such as questran; niacin; anti-atherosclerotic agents, such as ACAT inhibitors; MTP Inhibitors; calcium channel blockers, such as amlodipine besylate; potassium channel activators; alpha-histamine H1 agents; beta-histamine H1 agents, such as carvedilol and metoprolol; antiarrhythmic agents; diuretics, such as chlorothiazide, hydrochlorothiazide, flumethiazide, hydroflumethiazide, bendroflumethiazide, methylchlorothiazide, trichloromethiazide, polythiazide, benzothiazide, ethacrynic acid, tricrynafen, chlorthalidone, furosenilde, musolimine, bumetanide, triamterene, amiloride, and spironolactone; thrombolytic agents, such as tissue plasminogen activator (tPA), recombinant tPA, streptokinase, urokinase, prourokinase, and anisoylated plasminogen streptokinase activator complex (APSAC); anti-diabetic agents, such as biguanides (e.g. metformin), glucosidase inhibitors (e.g., acarbose), insulins, meglitinides (e.g., repaglinide), sulfonylureas (e.g., glimepiride, glyburide, and glipizide), thiozolidinediones (e.g. troglitazone, rosiglitazone and pioglitazone), and PPAR-gamma agonists; mineralocorticoid receptor antagonists, such as spironolactone and eplerenone; growth hormone secretagogues; aP2 inhibitors; phosphodiesterase inhibitors, such as PDE III inhibitors (e.g., cilostazol) and PDE V inhibitors (e.g., sildenafil, tadalafil, vardenafil); protein tyrosine kinase inhibitors; antiinflammatories; antiproliferatives, such as methotrexate, FK506 (tacrolimus, Prograf), mycophenolate mofetil; chemotherapeutic agents; immunosuppressants; anticancer agents and cytotoxic agents (e.g., alkylating agents, such as nitrogen mustards, alkyl sulfonates, nitrosoureas, ethylenimines, and triazenes); antimetabolites, such as folate antagonists, purine analogues, and pyrridine analogues; antibiotics, such as anthracyclines, bleomycins, mitomycin, dactinomycin, and plicamycin; enzymes, such as L-asparaginase; farnesyl-protein transferase inhibitors; hormonal agents, such as glucocorticoids (e.g., cortisone), estrogens/antiestrogens, androgens/antiandrogens, progestins, and luteinizing hormone-releasing hormone antagonists, and octreotide acetate; microtubule-disruptor agents, such as ecteinascidins; microtubule-stabilizing agents, such as pacitaxel, docetaxel, and epothilones A-F; plant-derived products, such as *vinca* alkaloids, epipodophyllotoxins, and taxanes; and topoisomerase inhibitors; prenyl-protein transferase inhibitors; and cyclosporins; steroids, such as prednisone and dexamethasone; cytotoxic drugs, such as azathiprine and cyclophosphamide; TNF-alpha inhibitors, such as tenidap; anti-TNF antibodies or soluble TNF receptor, such as etanercept, rapamycin, and leflunimide; and cyclooxygenase-2 (COX-2) inhibitors, such as celecoxib and rofecoxib; and miscellaneous agents such as, hydroxyurea, procarbazine, mitotane, hexamethylmelamine, gold compounds, platinum coordination complexes, such as cisplatin, satraplatin, and carboplatin.

Kits/Articles of Manufacture

For use in the therapeutic applications described herein, kits and articles of manufacture are also described herein. Such kits can comprise a carrier, package, or container that is compartmentalized to receive one or more containers such as vials, tubes, and the like, each of the container(s) comprising one of the separate elements to be used in a method described herein.

For example, the container(s) can comprise one or more compounds described herein, optionally in a composition or in combination with another agent as disclosed herein. The container(s) optionally have a sterile access port (for example the container can be an intravenous solution bag or a vial having a stopper pierceable by a hypodermic injection needle). Such kits optionally comprise a compound with an identifying description or label or instructions relating to its use in the methods described herein.

A kit will typically comprise one or more additional containers, each with one or more of various materials (such as reagents, optionally in concentrated form, and/or devices) desirable from a commercial and user standpoint for use of a compound described herein. Non-limiting examples of such materials include, but are not limited to, buffers, diluents, filters, needles, syringes; carrier, package, container, vial and/or tube labels listing contents and/or instructions for use, and package inserts with instructions for use. A set of instructions will also typically be included.

A label or package insert can be on, in, or associated with the container. A label can be used to indicate that the contents are to be used for a specific therapeutic application. The label can also indicate directions for use of the contents, such as in the methods described herein. These other therapeutic agents may be used, for example, in the amounts indicated in the Physicians' Desk Reference (PDR) or as otherwise determined by one of ordinary skill in the art.

As used herein, and unless otherwise indicated, the following abbreviations have the following meanings Me refers to methyl ($CH_3$—), Et refers to ethyl ($CH_3CH_2$—), i-Pr refers to isopropyl (($CH_3)_2CH_2$—), t-Bu or tert-butyl refers to tertiary butyl (($CH_3)_3CH$—), Ph refers to phenyl, Bn refers to benzyl ($PhCH_2$—), Bz refers to benzoyl (PhCO—), MOM refers to methoxymethyl, Ac refers to acetyl, TMS refers to trimethylsilyl, TBS refers to tert-butyldimethylsilyl, Ms refers to methanesulfonyl ($CH_3SO_2$—), Ts refers to p-toluenesulfonyl (p-$CH_3PhSO_2$—), Tf refers to trifluoromethanesulfonyl ($CF_3SO_2$—), TfO refers to trifluoromethanesulfonate ($CF_3SO_3$—), $D_2O$ refers to deuterium oxide, DMF refers to N,N-dimethylformamide, DCM refers to dichloromethane ($CH_2Cl_2$), THF refers to tetrahydrofuran, EtOAc refers to ethyl acetate, Et$_2$O refers to diethyl ether, MeCN refers to acetonitrile (CH$_3$CN), NMP refers to 1-N-methyl-2-pyrrolidinone, DMA refers to N,N-dimethylacetamide, DMSO refers to dimethylsulfoxide, DCC refers to 1,3-dicyclohexyldicarbodiimide, EDCI refers to 1-(3-dimethylaminopropyl)-3-ethylcarbodiimide, Boc refers to tert-butylcarbonyl, Fmoc refers to 9-fluorenylmethoxycarbonyl, TBAF refers to tetrabutylammonium fluoride, TBAI refers to tetrabutylammonium iodide, TMEDA refers to N,N,N,N-tetramethylethylene diamine, Dess-Martin periodinane or Dess Martin reagent refers to 1,1,1-triacetoxy-1,1-dihydro-1,2-benziodoxol-3(1H)-one, DMAP refers to 4-N,N-dimethylaminopyridine, (i-Pr)$_2$NEt or DIEA or Hunig's base refers to N,N-diethylisopropylamine, DBU refers to 1,8-Diazabicyclo[5.4.0]undec-7-ene, (DHQ)$_2$AQN refers to dihydroquinine anthraquinone-1,4-diyl diether, (DHQ)$_2$PHAL refers to dihydroquinine phthalazine-1,4-diyl diether, (DHQ)$_2$PYR refers to dihydroquinine 2,5-diphenyl-4,6-pyrimidinediyl diether, (DHQD)$_2$AQN refers to dihydroquinidine anthraquinone-1,4-diyl diether, (DHQD)$_2$PHAL refers to dihydroquinidine phthalazine-1,4-diyl diether, (DHQD)$_2$PYR refers to dihydroquinidine 2,5-diphenyl-4,6-pyrimidinediyl diether, LDA refers to lithium diisopropylamide, LiTMP refers to lithium 2,2,6,6-tetramethylpiperdinamide, n-BuLi refers to n-butyl lithium, t-BuLi refers to tert-butyl lithium, IBA refers to 1-hydroxy-1,2-benziodoxol-3(1H)-one 1-oxide, OsO$_4$ refers to osmium tetroxide, m-CPBA refers to meta-chloroperbenzoic acid, DMD refers to dimethyl dioxirane, PDC refers to pyridinium dichromate, NMO refers to N-methyl morpholine-N-oxide, NaHMDS refers to sodium hexamethyldisilazide, LiHMDS refers to lithium hexamethyldisilazide, HMPA refers to hexamethylphosphoramide, TMSCl refers to trimethylsilyl chloride, TMSCN refers to trimethylsilyl cyanide, TBSCl refers to tert-butyldimethylsilyl chloride, TFA refers to trifluoroacetic acid, TFAA refers to trifluoroacetic anhydride, AcOH refers to acetic acid, Ac$_2$O refers to acetic anhydride, AcCl refers to acetyl chloride, TsOH refers to p-toluenesulfonic acid, TsCl refers to p-toluenesulfonyl chloride, MBHA refers to 4-methylbenzhydrylamine, BHA refers to benzhydrylamine, ZnCl$_2$ refers to zinc (II) dichloride, BF$_3$ refers to boron trifluoride, Y(OTf)$_2$ refers to yttrium (III) trifluoromethanesulfonate, Cu(BF$_4$)$_2$ refers to copper (II) tetrafluoroborate, LAH refers to lithium aluminum hydride (LiAlH$_4$), LAD refers to lithium aluminum deuteride, NaHCO$_3$ refers to Sodium bicarbonate, K$_2$CO$_3$ refers to Potassium carbonate, NaOH refers to sodium hydroxide, KOH refers to potassium hydroxide, LiOH refers to lithium hydroxide, HCl refers to hydrochloric acid, H$_2$SO$_4$ refers to sulfuric acid, MgSO$_4$ refers to magnesium sulfate, and Na$_2$SO$_4$ refers to sodium sulfate. $^1$H NMR refers to proton nuclear magnetic resonance, $^{13}$C NMR refers to carbon-13 nuclear magnetic resonance, NOE refers to nuclear overhauser effect, NOESY refers to nuclear overhauser and exchange spectroscopy, COSY refers to homonuclear correlation spectroscopy, HMQC refers to proton detected heteronuclear multiplet-quantum coherence, HMBC refers to heteronuclear multiple-bond connectivity, s refers to singlet, br s refers to broad singlet, d refers to doublet, br d refers to broad doublet, t refers to triplet, q refers to quartet, dd refers to double doublet, m refers to multiplet, ppm refers to parts per million, IR refers to infrared spectrometry, MS refers to mass spectrometry, HRMS refers to high resolution mass spectrometry, EI refers to electron impact, FAB refers to fast atom bombardment, CI refers to chemical ionization, HPLC refers to high pressure liquid chromatography, TLC refer to thin layer chromatography, R$_f$ refers to retention factor, R$_t$ refers to retention time, GC refers to gas chromatography, min is minutes, h is hours, rt or RT is room or ambient temperature, g is grams, mg is milligrams, kg is kilograms, L is liters, mL is milliliters, mol is moles and mmol is millimoles.

The invention is further illustrated by the following examples.

EXAMPLES

Example 1—d$_9$-2-(4-Methoxyphenyl)-acetic Acid

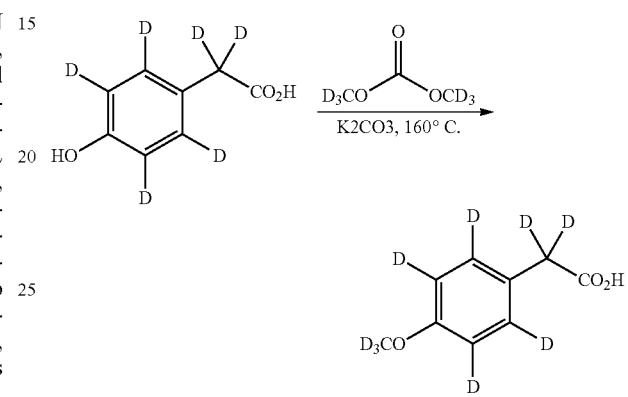

d$_9$-(4-Methoxyphenyl)-acetic acid can be prepared according to known literature procedures Ouk et al., *Green Chemistry*, 2002, 4(5), 431-435, which is hereby incorporated by reference in its entirety, by reacting d$_6$-(4-hydroxyphenyl)-acetic acid (1 equiv, Cambridge Isotopes Laboratories), K$_2$CO$_3$ (0.04 equiv) and d$_6$-carbonic acid dimethyl ester (1.25 equiv, Cambridge Isotopes Laboratories) at 160° C. until completion.

Example 2—d$_{15}$-2-(4-Methoxyphenyl)-N,N-dimethyl-acetamide

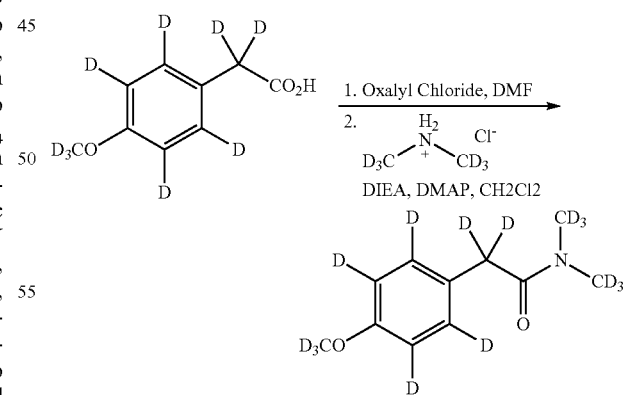

The title compound is prepared according to the procedure described in Yardley et al, *Journal of Medicinal Chemistry* 1990, 33(10), 2899-2905, which is hereby incorporated by reference in its entirety. A solution of d$_9$-(4-methoxyphenyl)-acetic acid (1 equiv) in methylene chloride is treated with oxalyl chloride (1.22 equiv) and DMF (catalytic amount) and then stirred at room temperature until all acid is converted to the acid chloride. The solvent is removed under reduced pressure and the residue is taken up in methylene chloride and treated with $d_6$-dimethylamine hydrochloride (1 equiv, Cambridge Isotopes Laboratories), ethyl diisopropylamine (2.1 equiv), and DMAP (0.2 equiv). The mixture is stirred overnight, the solvent is removed under reduced pressure and the crude residue is purified by silica gel column chromatography.

Example 3—$d_{24}$-2-(1-Hydroxycyclohexyl)-2-(4-methoxyphenyl)-N,N-dimethylacetamide

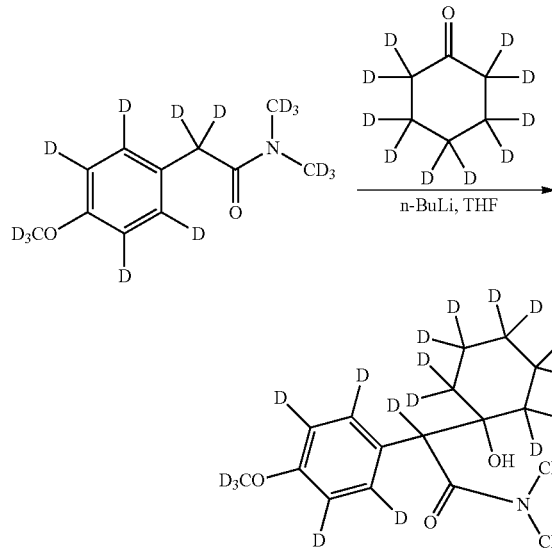

The title compound is prepared according to the procedure described in Yardley et al., *Journal of Medicinal Chemistry* 1990, 33(10), 2899-2905, which is hereby incorporated by reference in its entirety. A solution of $d_{15}$-2-(4-methoxyphenyl)-N,N-dimethyl-acetamide (1 equiv) in THF is treated with n-butyllithium (1 equiv) at −78° C. The mixture is stirred for 90 minutes at −78° C.; a THF solution of $d_{10}$-cyclohexanone (1.2 equiv, Sigma-Aldrich) is added, and stirring is maintained until completion. The reaction is quenched by addition of $D_2O$ (2 equiv), the mixture is warmed to room temperature and the solvent is removed under reduced pressure and the crude residue is purified by silica gel column chromatography.

Example 4—$d_{26}$-1-[2-Dimethylamino-1-(4-methoxyphenyl)-ethyl]-cyclohexanol

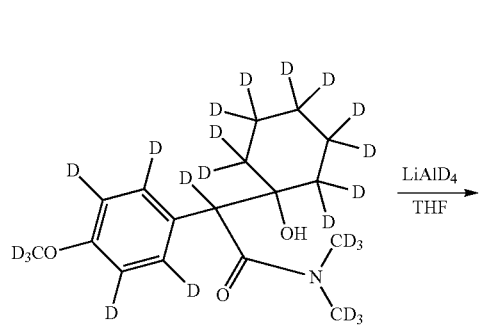

-continued

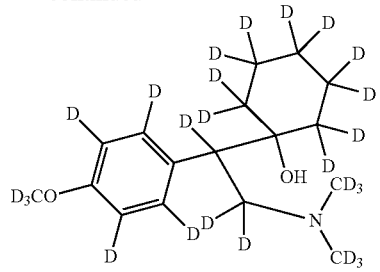

The title compound is prepared according to the procedure described in Yardley et al., *Journal of Medicinal Chemistry* 1990, 33(10), 2899-2905, which is hereby incorporated by reference in its entirety. $d_{24}$-2-(1-Hydroxycyclohexyl)-2-(4-methoxyphenyl)-N,N-dimethyl-acetamide (1 equiv) in THF is added dropwise to a mixture of lithium aluminum deuteride (1.6 equiv) at 0° C. and stirred until completion. The reaction is quenched with $D_2O$, and worked up under standard conditions known to one skilled in the art. The mixture is then filtered and the precipitate is washed several times with THF. The combined filtrates are evaporated, and the residue is recrystallized from a suitable solvent.

Example 5—$d_3$-(4-Methoxyphenyl)-acetonitrile

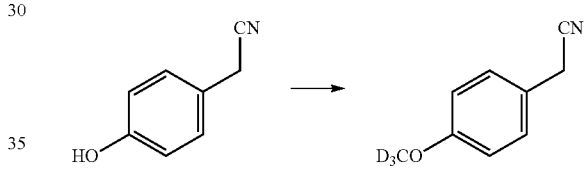

$d_3$-Iodomethane (8.70 g, 60 mmol) was added to a stirred solution of (4-hydroxyphenyl)-acetonitrile (4.50 g, 30 mmol) in acetone (30 mL) containing potassium carbonate (6.21 g, 45 mmol) at ambient temperature, and the mixture was heated at reflux overnight, cooled to ambient temperature, filtered, and concentrated to give the crude product, which was purified by flash chromatography using hexanes-ethyl acetate to afford the desired product, $d_3$-(4-methoxyphenyl)-acetonitrile, as a light yellow oil.

Yield: 3.99 g (89%). $^1$H-NMR (CDCl$_3$) δ ppm: 3.67 (s, 2H), 6.88 (d, 2H, J=8.7 Hz), 7.22 (d, 2H, J=8.7 Hz).

Example 6—$d_3$-(1-Hydroxycyclohexyl)-(4-methoxyphenyl)-acetonitrile

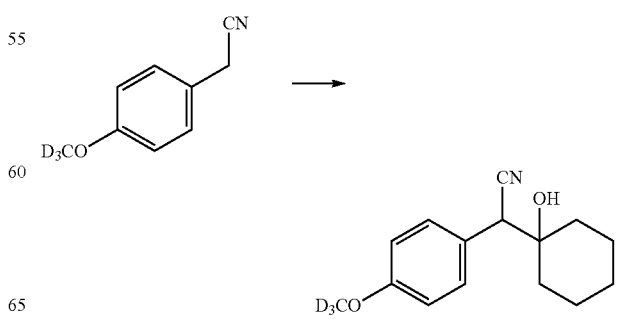

Tetra-n-butyl ammonium hydrogen sulfate (0.10 g, 0.29 mmol) and 2N NaOH (1.2 mL) were added sequentially to a vigorously stirred $d_3$-(4-methoxyphenyl)-acetonitrile (0.85 g, 5.66 mmol) at 0° C., and stirring was maintained for 30 minutes. Cyclohexanone (0.67 g, 6.8 mmol) was added to this mixture at 0-5° C. over 10 minute. The reaction mixture was allowed to warm to ambient temperature and vigorous stirring was continued for an additional 1 hour. The white precipitate was filtered and washed with water and hexanes to afford the desired product, $d_3$-(1-hydroxycyclohexyl)-(4-methoxyphenyl)-acetonitrile, as a white solid.

Yield: 1.28 g (91%). $^1$H-NMR (CDCl$_3$) δ ppm: 1.05-1.80 (m, 10H), 3.73 (s, 1H), 6.90 (d, 2H, J=8.7 Hz), 7.27 (d, 2H, J=8.7 Hz).

Example 7—$d_3$-1-[2-Amino-1-(4-methoxyphenyl)-ethyl]-cyclohexanol

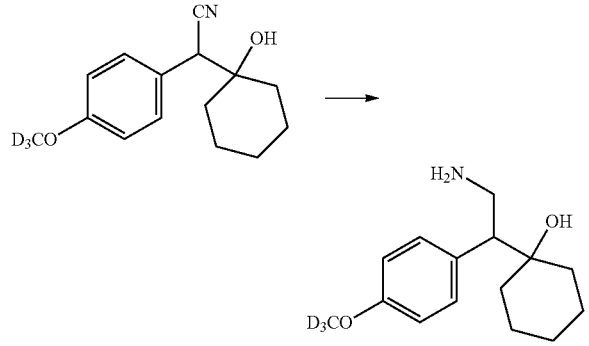

$d_3$-(1-Hydroxycyclohexyl)-(4-methoxyphenyl)-acetonitrile (400.0 mg, 1.61 mmol) was reduced on an H-Cube™ continuous-flow hydrogenation reactor (Thales Nanotechnology, Budapest, Hungary) equipped with a Raney Ni catalyst cartridge (eluent: 2.0M ammonia in methanol, flow rate: 1 mL/min, temperature: 80° C., pressure: 80 bar) to yield the desired product, $d_3$-1-[2-amino-1-(4-methoxyphenyl)-ethyl]-cyclohexanol, as a clear colorless oil.

Yield: 280 mg (69%). $^1$H-NMR (CDCl$_3$) δ ppm: 1.05-1.80 (m, 10H), 2.59 (br s, 2H), 2.68 (t, 1H, 6.9 Hz), 3.21 (m, 2H), 6.83 (d, 2H, J=9.0 Hz), 7.17 (d, 2H, J=9.0 Hz).

Example 8—$d_{12}$-1-[2-Trimethylammonium-1-(4-methoxyphenyl)-ethyl]-cyclohexanol Iodide

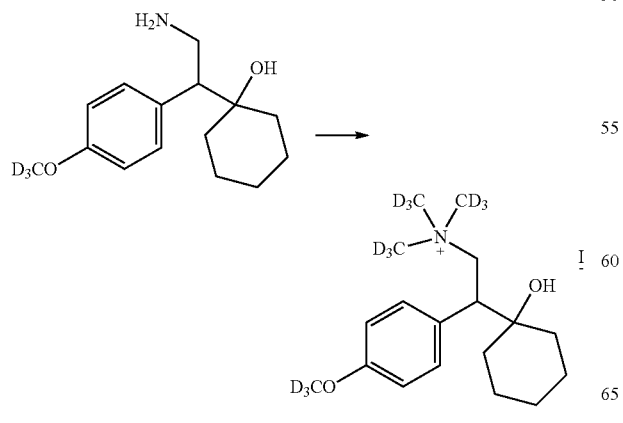

D3-Iodomethane (0.4 mL, 6.34 mmol) and potassium carbonate (424 mg, 3.0 mmol) were added at ambient temperature to a solution of $d_3$1-[2-amino-1-(4-methoxyphenyl)-ethyl]-cyclohexanol (252 mg, 1.0 mmol) in anhydrous tetrahydrofuran (1.5 ml.), and stirred at ambient temperature for 20 hours. The reaction mixture was diluted with tetrahydrofuran, filtered, and the filtrate was concentrated in vacuo to provide the product, $d_{12}$-1-[2-trimethylammonium-1-(4-methoxyphenyl)-ethyl]-cyclohexanol iodide, as a beige solid. $^1$H-NMR (CD$_3$OD) δ ppm: 0.90-1.80 (m, 10H), 3.19 (m, 1H), 4.00 (m, 2H), 6.93 (d, J=8.1 Hz, 2H), 7.43 (d, J=8.1 Hz, 2H).

Example 9—$d_9$-1-[2-Dimethylamino-1-(4-methoxyphenyl)-ethyl]-cyclohexanol ($d_9$-venlafaxine)

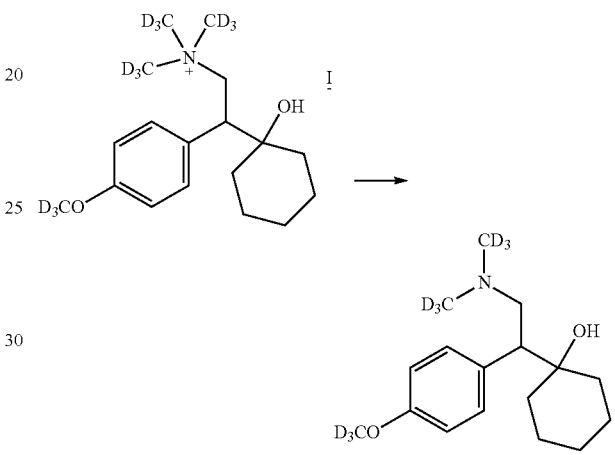

A solution of $d_{12}$-1-[2-trimethylammonium-1-(4-methoxyphenyl)-ethyl]-cyclohexanol iodide in 3-amino-1-propanol (1 mL) was heated at 170° C. for 4 hours, cooled to ambient temperature, diluted with water and extracted with ethyl acetate. The combined organic layers were washed with brine, dried and concentrated under reduced pressure. The resulting residue was dissolved in 6N hydrochloric acid (5 ml.), washed with ether. The aqueous layer was basified with 30% aqueous sodium hydroxide to pH=11-12 and extracted with ethyl acetate. The organic extract was washed with brine, dried, and concentrated to afford $d_9$-venlafaxine (208 mg, 73%). $^1$H-NMR (CDCl$_3$) δ ppm: 0.78-1.80 (m, 10H), 2.33 (dd, 1H, J=12.0, 3.3 Hz), 2.96 (dd, 1H, J=12.0, 3.3 Hz), 3.31 (t, 1H, J=12.0 Hz), 6.81 (d, 2H, J=9.0 Hz), 7.17 (d, 2H, J=9.0 Hz). MS (m/z): 287 (M+1).

Example 10—$d_9$-1-[2-Dimethylamino-1-(4-methoxyphenyl)-ethyl]-cyclohexanol hydrochloride ($d_9$-venlafaxine hydrochloride)

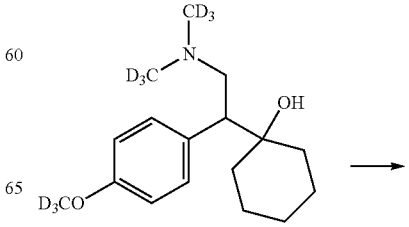

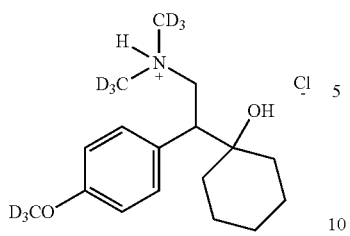

A solution of d₉-venlafaxine (63 mg, 0.22 mmol) in ether (10 mL) was treated with 2N hydrochloric acid in ether (0.2 mL) at 0° C. for 10 minutes. The white precipitate was collected by filtration, washed with ether, and dried in vacuo to provide d₉-venlafaxine hydrochloride salt (60 mg, 85%). 1H-NMR (CD₃OD) δ ppm: 0.95-1.80 (m, 10H), 2.83 (s, 6H), 3.04 (dd, 1H, J=9.9, 5.4 Hz), 3.68 (m, 2H), 6.96 (d, 2H, J=9.0 Hz), 7.30 (d, 1H, J=9.0 Hz).

Example 11—d₃-1-[2-Trimethylammonium-1-(4-methoxyphenyl)-ethyl]-cyclohexanol Iodide

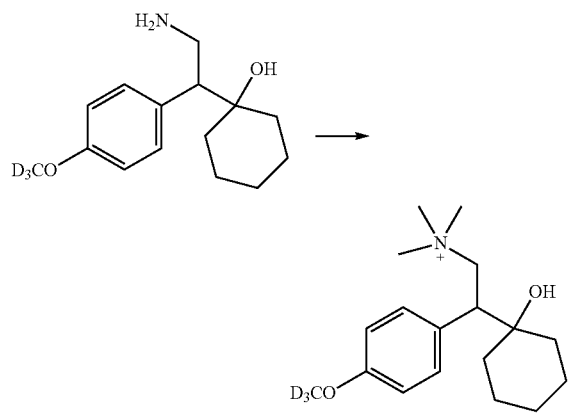

Prepared according to Example 8 by substituting methyl iodide for d₃-methyl iodide. 1H-NMR (CD₃OD) δ ppm: 0.90-1.80 (m, 10H), 3.05 (s, 9H), 3.12 (m, 1H), 3.96 (m, 2H), 6.94 (d, J=8.1 Hz, 2H), 7.39 (d, J=8.1 Hz, 2H).

Example 12—d₃-1-[2-Dimethylamino-1-(4-methoxyphenyl)-ethyl]-cyclohexanol (d₃-venlafaxine)

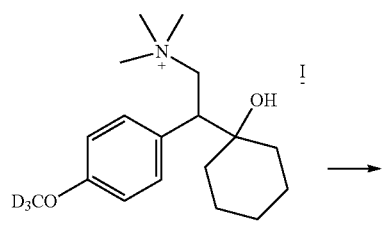

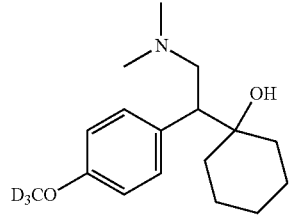

Prepared according to Example 9. 1H-NMR (CD₃OD) δ ppm: 0.84-1.54 (m, 10H), 2.42 (s, 6H), 2.84-2.92 (m, 2H), 3.26-3.36 (m, 1H), 6.87 (d, 2H), 7.18 (d, 2H).

Example 13—d₃-1-[2-Dimethylamino-1-(4-methoxyphenyl)-ethyl]-cyclohexanol hydrochloride (d₃-venlafaxine hydrochloride)

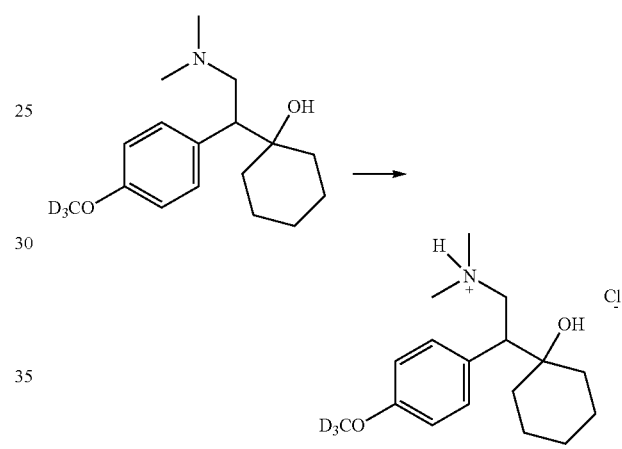

Prepared according to Example 10.

Example 14—d₃-1-[2-Dimethylamino-1-(4-methoxyphenyl)-ethyl]-cyclohexanol (d₃-venlafaxine)

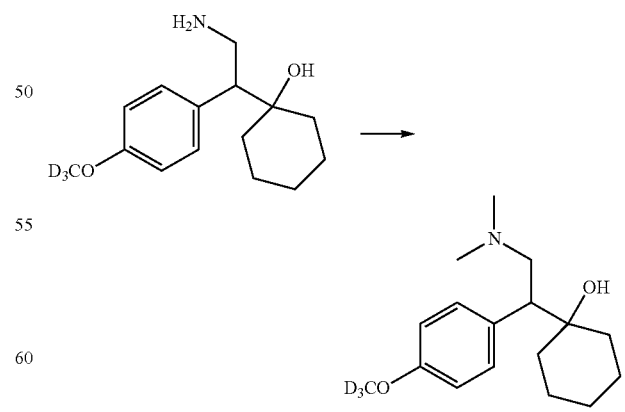

d₃-1-[2-Amino-1-(4-methoxyphenyl)-ethyl]-cyclohexanol (207 mg, 0.82 mmol), 37% aqueous formaldehyde (0.3 mL), formic acid (0.3 mL) and water (2 mL) were stirred at 80-90° C. for 12 hours, concentrated in vacuo to a volume of 1.5 mL, made basic by the dropwise addition of aqueous 20% sodium hydroxide, and extracted with ethyl acetate. The combined organic layers were washed with brine, dried ($Na_2SO_4$), filtered and concentrated in vacuo to give a crude residue which was purified by silica gel chromatography (ethyl acetate-methanol-ammonium hydroxide) to give the desired product, $d_3$-1-[2-dimethylamino-1-(4-methoxyphenyl)-ethyl]-cyclohexanol.

Yield: 24.4 mg (11%). $^1$H-NMR (methanol-$d_4$) δ ppm: 0.84-1.54 (m, 10H), 2.42 (s, 6H), 2.84-2.92 (m, 2H), 3.26-3.36 (m, 1H), 6.87 (d, 2H), 7.18 (d, 2H).

Example 15—$d_9$-1-[2-Dimethylamino-1-(4-methoxyphenyl)-ethyl]-cyclohexanol ($d_9$-venlafaxine)

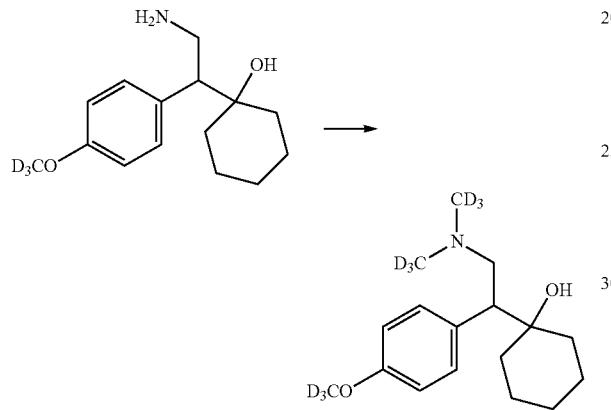

A solution of $d_3$-1-[2-amino-1-(4-methoxyphenyl)-ethyl]-cyclohexanol (0.126 g, 0.5 mmol), $d_2$-formic acid (0.3 mL), and $d_2$-formaldehyde (20 wt % in D2O, 0.25 mL) in D2O (1.5 mL) was heated at 100° C. for 16 hours, cooled to ambient temperature, diluted with water (5 mL), neutralized with 35% aqueous ammonia, and extracted with ethyl acetate. The combined organic layers were dried over sodium sulfate and concentrated under reduced pressure to yield a crude residue which was purified by flash chromatography (ethyl acetate-methanol-$NH_4OH$) to give the desired product, $d_9$-1-[2-methylamino-1-(4-methoxyphenyl)-ethyl]-cyclohexanol, as a light yellow semi-solid.

Yield: 0.024 g (20%). $^1$H-NMR ($CDCl_3$) δ ppm: 0.78-1.80 (m, 10H), 2.33 (dd, 1H, J=12.0, 3.3 Hz), 2.96 (dd, 1H, J=12.0, 3.3 Hz), 3.31 (t, 1H, J=12.0 Hz), 6.81 (d, 2H, J=9.0 Hz), 7.17 (d, 2H, J=9.0 Hz). MS (m/z): 287 (M+1).

Example 16—$d_{14}$-(1-Hydroxycyclohexyl)-(4-methoxyphenyl)-acetonitrile

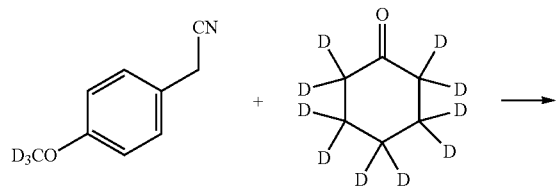

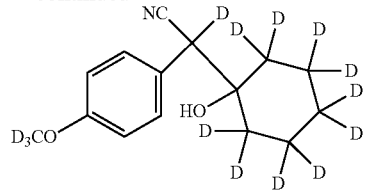

The title compound was prepared as in Example 6 by substituting $d_{10}$-cyclohexanone (Sigma-Aldrich) for cyclohexanone and 2N NaOD in $D_2O$ for 2N NaOH in water. The final product was purified by recrystallization from ethyl acetate-hexanes.

Yield (60%). $^1$H-NMR ($CDCl_3$) δ ppm: 1.60 (br s, 1H), 6.90 (d, 2H, J=8.4 Hz), 7.26 (d, 2H, J=8.4 Hz).

Example 17—$d_{14}$-1-[2-Amino-1-(4-methoxyphenyl)-ethyl]-cyclohexanol

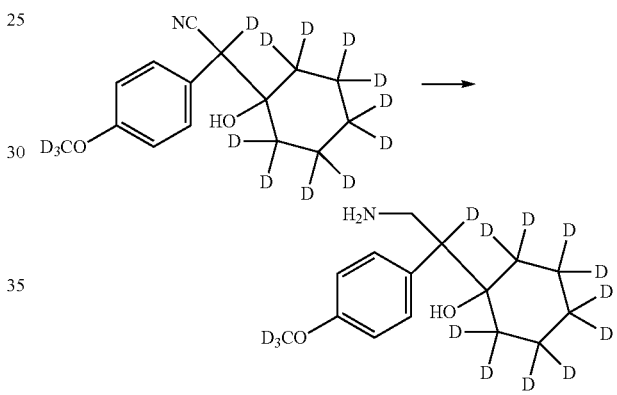

$d_{14}$-(1-Hydroxycyclohexyl)-(4-methoxyphenyl)-acetonitrile (570.0 mg, 2.21 mmol) was reduced on an H-Cube™ continuous-flow hydrogenation reactor (Thales Nanotechnology, Budapest, Hungary) equipped with a Raney Ni catalyst cartridge (eluent: 2.0M ammonia in methanol, flow rate: 1 mL/min, temperature: 80° C., pressure: 80 bar) to yield the desired product, $d_{14}$-1-[2-amino-1-(4-methoxyphenyl)-ethyl]-cyclohexanol, as a clear colorless oil.

Yield: 530 mg (92%). $^1$H-NMR ($CDCl_3$) δ ppm: 2.62 (br s, 3H), 3.21 (dd, 2H), 6.83 (d, 2H), 7.17 (d, 2H).

Example 18—$d_{14}$-1-[2-Dimethylamino-1-(4-methoxyphenyl)-ethyl]-cyclohexanol ($d_{14}$-venlafaxine)

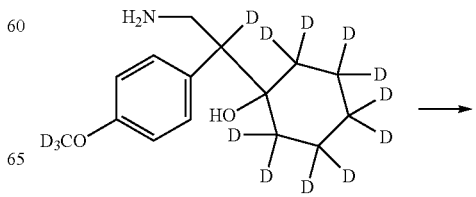

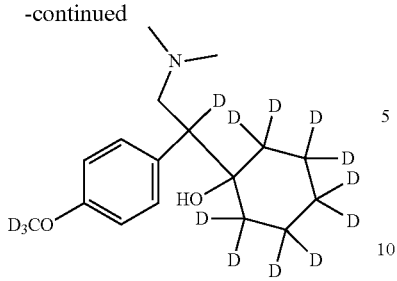

A solution of d₁₄-1-[2-amino-1-(4-methoxyphenyl)-ethyl]-cyclohexanol (257.0 mg, 0.98 mmol), formic acid (0.334 mL), and formaldehyde (37% in water, 0.146 mL) in water (2.32 mL) was stirred at room temperature for 45 minutes. Formaldehyde (37% in water, 0.146 mL) was added and the mixture was heated to reflux for 17 hours, cooled to room temperature, washed with ethyl acetate, made basic with 20% aqueous sodium hydroxide and extracted with ethyl acetate. The combined organic fractions were washed with brine, dried (Na₂SO₄), filtered and concentrated in vacuo to give a crude residue which was purified by column chromatography (ethyl acetate-methanol-ammonium hydroxide) to give the desired product, d₁₄-1-[2-dimethylamino-1-(4-methoxyphenyl)-ethyl]-cyclohexanol, as a clear colorless oil.

Yield: 154.4 mg (54%), $^1$H-NMR (methanol-d₄) δ ppm: 2.25 (s, 6H), 2.55 (d, 1H), 3.14 (d, 1H), 6.84 (d, 2H), 7.13 (d, 2H).

Example 19—d₂₀-1-[2-Dimethylamino-1-(4-methoxyphenyl)-ethyl]-cyclohexanol (d₂₀-venlafaxine)

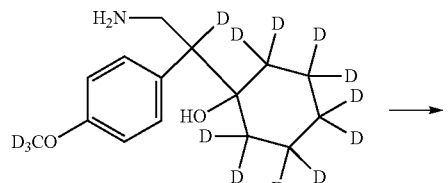

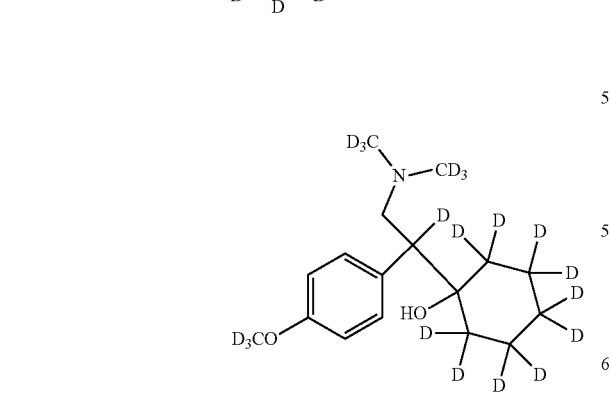

The title compound was prepared as in Example 15.

Yield (31%). $^1$H-NMR (CDCl₃) δ ppm: 2.33 (d, 1H, J=12.6 Hz), 3.30 (d, 1H, J=12.6 Hz), 6.81 (d, 2H, J=9.0 Hz), 7.05 (d, 2H, J=9.0 Hz). MS (m/z): 298 (M+1).

Example 20—d₆-4-[2-Dimethylamino-1-(1-hydroxycyclohexyl)-ethyl]-phenol (d₆-O-desmethyl-venlafaxine)

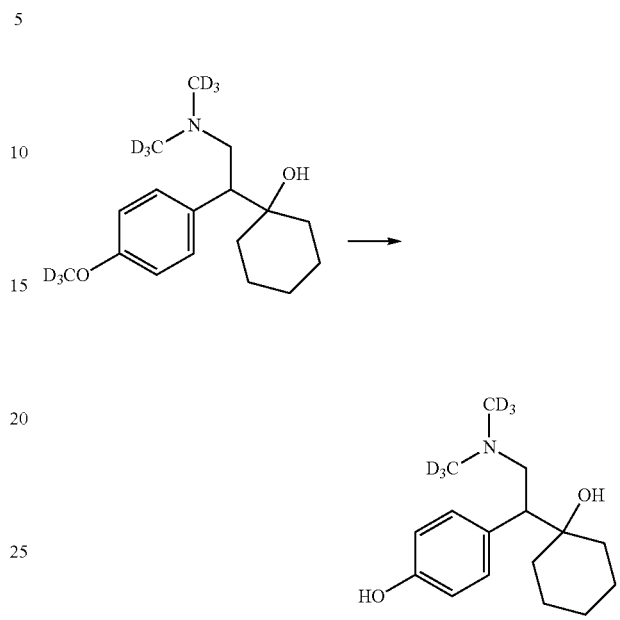

A 1.0 M solution of boron tribromide in methylene chloride (0.125 mL, 0.125 mol) was added at −40° C. to a stirred solution of d₉-venlafaxine (17 mg, 0.059 mmol) in methylene chloride (0.5 mL) over 5 minutes, and the mixture was allowed to warm to 0° C. over 30 minutes. After being stirred for additional 3 hours at 0° C., the reaction was quenched at 0° C. with aqueous 2N NaOH (0.35 mL) and the mixture was slowly allowed to warm to ambient temperature overnight with stirring. The solvent was removed under reduced pressure and the resulting residue was extracted with ethyl acetate. The combined organic layers were washed with brine, dried over sodium sulfate, filtered, and concentrated in vacuo to give the title compound as a beige solid.

Yield: 75%. $^1$H-NMR (CDCl₃) δ: 0.75-1.80 (m, 10H), 2.52 (dd, 1H, J=12.3, 4.2 Hz), 2.99 (dd, 1H, J=10.2, 4.2 Hz), 3.39 (t, 1H, J=10.8 Hz), 6.75 (d, 2H, J=8.7 Hz), 6.99 (d, 1H, J=8.7 Hz). MS: m/z 270.1 (M⁺+1).

Example 21—d₁₁-4-[2-Dimethylamino-1-(1-hydroxycyclohexyl)-ethyl]-phenol (d₁₁-O-desmethyl-venlafaxine)

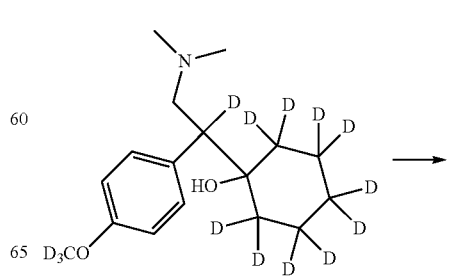

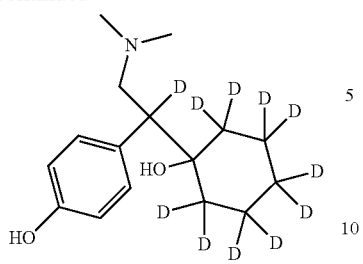

The title compound is prepared from $d_{14}$-venlafaxine according to Example

Example 22—$d_{23}$-4-[2-Dimethylamino-1-(1-hydroxycyclohexyl)-ethyl]-phenol ($d_{23}$-O-desmethylvenlafaxine)

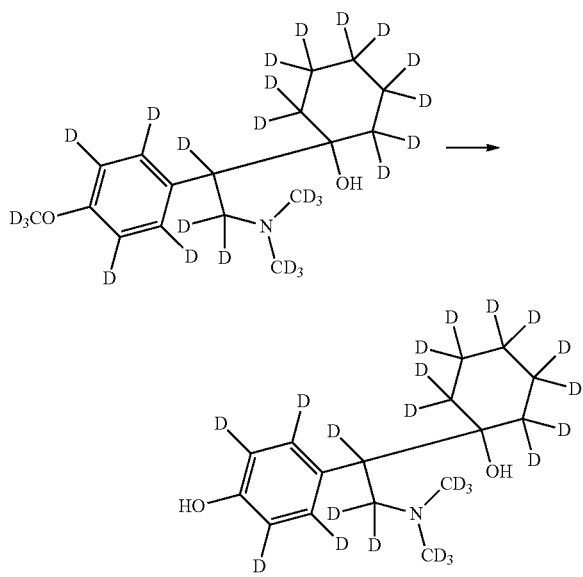

The title compound is prepared from $d_{26}$-venlafaxine according to Example 20.

Example 23—(S)-$d_9$-1-[2-Dimethylamino-1-(4-methoxyphenyl)-ethyl]-cyclohexanol Hydrochloride Salt ((S)-$d_9$-venlafaxine HCl)

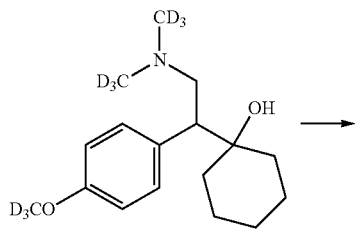

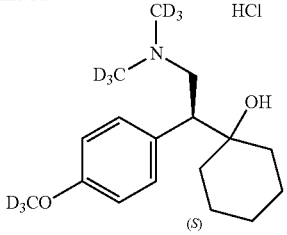

A solution of (−)-di-p-toluoyl-L-tartaric acid (3.60 mmol) in ethyl acetate (10 mL) was added at once at room temperature to a solution of $d_9$-venlafaxine (7.22 mmol) in ethyl acetate (20 mL), and the mixture was stirred at room temperature for 4 hours. The resulting precipitate was collected by filtration, dried and recrystallized from a mixture of methanol and ethyl acetate to afford $d_9$-(S)-venlafaxine di-p-toluoyl-L tartrate salt as white crystals (optical purity >99.5% by a chiral HPLC). The filtrate was used to provide $d_9$-(R)-venlafaxine (see Example 18). Chiral separation was performed at ambient temperature on an Agilent 1100 HPLC equipped with a Chirobiotic V chiral column (Astec), 250× 4.6 mm column. Isocratic gradient: 5 mM ammonium acetate in water (60%) and tetrahydrofuran (40%); Flowrate: 1 mL/min; Run time: 30 minutes; Injection volume: 10 μL injection (1 mg/mL). UV wavelength: 229 nm. All samples were dissolved in acetonitrile-water (1:1).

$d_9$-(S)-venlafaxine di-p-toluoyl-L tartarate salt was suspended in dichloromethane (25 mL) and treated with 2N NaOH until pH 13. The layers were separated and the aqueous layer was extracted with dichloromethane. The combined organic layers were washed with brine, dried over sodium sulfate, filtered, and concentrated to give $d_9$-(S)-venlafaxine as a white solid Yield: 0.71 g. $^1$H-NMR (CDCl$_3$) δ: 0.75-1.80 (m, 10H), 2.37 (s, 6H), 2.40 (m, 1H), 3.01 (dd, 1H, J=11.1, 3.3 Hz), 3.39 (t, 1H, J=12.0 Hz), 6.81 (d, 2H, J=8.7 Hz), 7.05 (d, 1H, J=8.7 Hz). MS: m/z 281.3 (M$^+$+1).

$d_9$-(S)-venlafaxine (0.69 g, 2.46 mol) was dissolved in ether (30 mL) and treated with a solution of 2N HCl in ether (1.7 mL) at 0-5° C. for 10 minutes. The precipitate was filtered, washed with ether, and recrystallized from a mixture of ether and methanol to give $d_9$-(S)-venlafaxine HCl salt as a white solid (optical purity>99.5% by chiral HPLC).

Yield: 0.55 g. $^1$H-NMR (CD$_3$OD) δ: 0.95-1.80 (m, 10H), 2.83 (s, 6H), 3.04 (dd, 1H, J=9.9, 5.4 Hz), 3.68 (m, 2H), 6.96 (d, 2H, J=9.0 Hz), 7.30 (d, 1H, J=9.0 Hz). Chiral HPLC: RT=23.45 min.

Example 24—(R)-$d_9$-1-[2-Dimethylamino-1-(4-methoxyphenyl)-ethyl]-cyclohexanol Hydrochloride Salt ((R)-$d_9$-venlafaxine HCl)

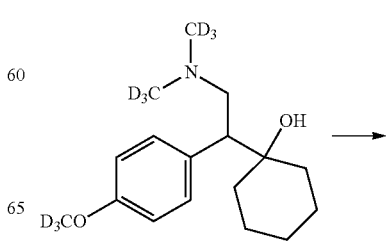

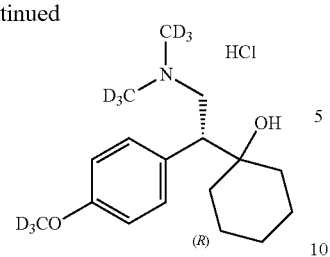

The filtrate obtained in Example 23 was concentrated under reduced pressure, and the resulting residue (1.80 g) was dissolved in dichloromethane and treated with 2N aqueous sodium hydroxide as in Example 23, washed with brine, and concentrated to give a white solid (1.01 g), which was dissolved in ethyl acetate (15 mL) and treated with (+)-di-p-toluoyl-D-tartaric acid in ethyl acetate (10 mL). The mixture was stirred at room temperature for 4 hours. The resulting white precipitate was collected by filtration and recrystallized from a mixture of ethyl acetate and methanol to provide $d_9$-(R)-venlafaxine di-p-toluoyl-D tartarate salt (optical purity>99.5% by chiral HPLC). The corresponding free base of $d_9$-(R)-venlafaxine (optical purity>99.5% by chiral HPLC) were prepared as in Example 23.

Example 25—(S)-$d_3$-1-[2-Dimethylamino-1-(4-methoxyphenyl)-ethyl]-cyclohexanol hydrochloride ((S)-$d_3$-venlafaxine HCl)

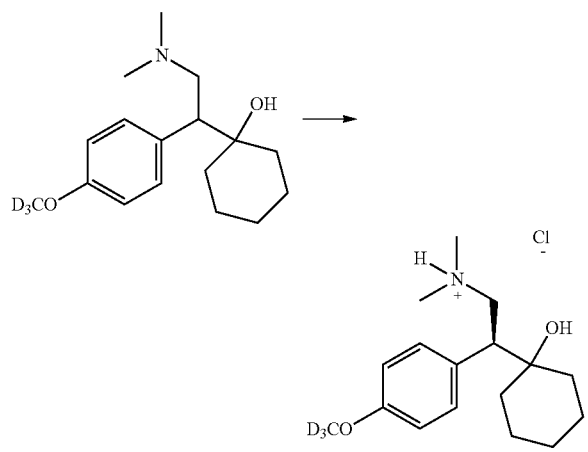

Prepared according to Example 23.

Example 26—(R)-$d_3$-1-[2-Dimethylamino-1-(4-methoxyphenyl)-ethyl]-cyclohexanol hydrochloride ((R)-$d_3$-venlafaxine HCl)

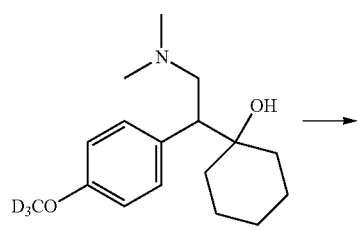

Prepared according to Example 23.

Example 27—$d_8$-5-(4-Methoxy-phenyl)-3-methyl-1-oxa-3-aza-spiro[5.5]undecane

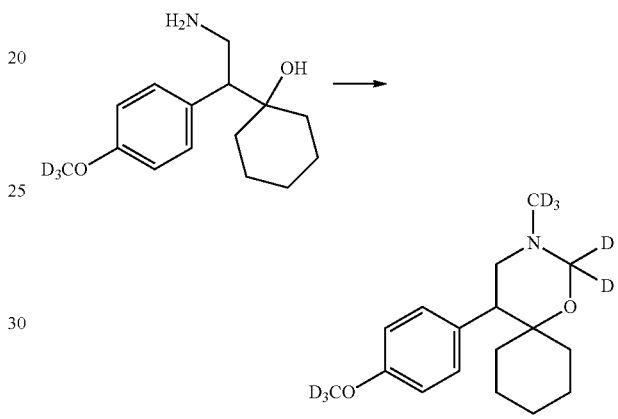

A solution of $d_3$-1-[2-amino-1-(4-methoxyphenyl)-ethyl]-cyclohexanol (0.126 g, 0.5 mmol), $d_2$ formic acid (0.3 mL), and $d_2$-formaldehyde (20 wt % in deuterium oxide, 0.25 mL) in deuterium oxide (1.5 mL) was heated at 100° C. for 16 hours, cooled to ambient temperature, diluted with water (5 mL), neutralized with 35% aqueous ammonia, and extracted with ethyl acetate. The combined organic layers were dried over sodium sulfate and concentrated under reduced pressure to yield a crude residue which was purified by flash chromatography (ethyl acetate-methanol-ammonium hydroxide) to give the desired product, $d_8$-5-(4-methoxy-phenyl)-3-methyl-1-oxa-3-aza-spiro[5.5]undecane.
$^1$H-NMR (CDCl$_3$) δ: 0.75-1.80 (m, 9H), 2.28 (br d, 1H), 2.70 (dd, 1H, J=12.3, 3.6 Hz), 3.03 (dd, 1H, J=12.3, 3.6 Hz), 3.21 (t, 1H, J=12.3 Hz), 6.81 (d, 2H, J=8.7 Hz), 7.05 (d, 2H, J=8.7 Hz). MS: m/z 284 (M+1).

Example 28—$d_9$-1-[2-Dimethylamino-1-(4-methoxyphenyl)-ethyl]-cyclohexanol ($d_9$-venlafaxine)

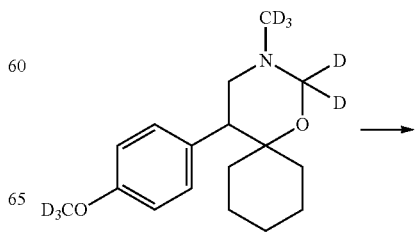

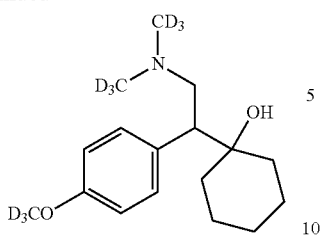

A stirred emulsion of d$_8$-5-(4-methoxyphenyl)-3-methyl-1-oxa-3-aza-spiro[5.5]undecane (1.93 g, 6.82 mmol) in deuterium oxide (25 mL) was treated with d$_2$-formic acid (1.96 g, 40.92 mmol), and 30% sodium deuteroxide in deuterium oxide (2.8 mL, 20.46 mmol) at ambient temperature. The resulting clear solution was heated at 100° C. for 20 hours, cooled to ambient temperature, diluted with water, basified to pH=11 with 2N aqueous sodium hydroxide, and extracted with ethyl acetate. The combined organic extracts were dried and concentrated under reduced pressure to give a crude residue, which was purified by flash column chromatography to afford d$_9$-venlafaxine (1.21 g, 62%) as a white solid.

Example 29—d$_8$-1-[2-Dimethylamino-1-(4-methoxyphenyl)-ethyl]-cyclohexanol (d$_8$-venlafaxine)

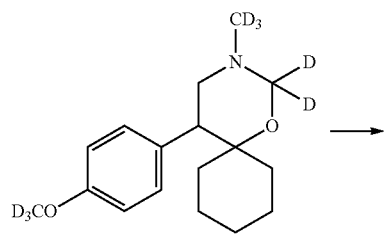

A stirred emulsion of d$_8$-5-(4-methoxyphenyl)-3-methyl-1-oxa-3-aza-spiro[5.5]undecane (123 mg, 0.434 mmol) in water (1 mL) was treated with formic acid (100 mg, 2.17 mmol), and sodium formate at 100° C. for 18 hours, cooled to ambient temperature, diluted with water, basified to pH=11 with 2N aqueous sodium hydroxide, and extracted with ethyl acetate. The combined organic extracts were dried and concentrated under reduced pressure to give a crude residue, which was purified by flash column chromatography to afford d$_8$-venlafaxine (68 mg, 55%) as a white solid. $^1$H-NMR (CDCl$_3$) δ: 0.75-1.80 (m, 10H), 2.28 (s, 1H), 2.32 (dd, 1H, J=12.3, 3.3 Hz), 2.96 (dd, 1H, J=12.3, 3.3 Hz), 3.31 (t, 1H, J=12.3 Hz), 6.81 (d, 2H, J=8.7 Hz), 7.05 (d, 2H, J=8.7 Hz). MS: m/z 286.4 (M+1).

Example 30—d$_8$-1-[2-Dimethylamino-1-(4-methoxyphenyl)-ethyl]-cyclohexanol hydrochloride (d$_8$-venlafaxine hydrochloride)

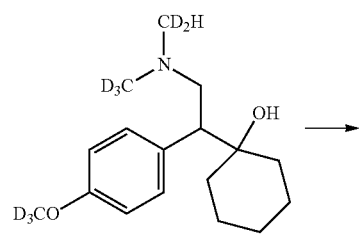

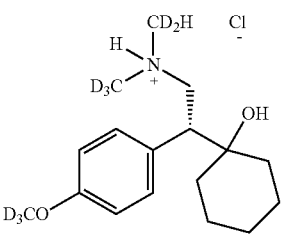

Prepared according to Example 23. $^1$H-NMR (CD$_3$OD) δ: 0.85-1.80 (m, 10H), 2.80 (s, 1H), 3.04 (dd, 1H, J=9.9, 5.4 Hz), 3.59-3.75 (m, 2H), 6.96 (d, 2H, J=8.4 Hz), 7.30 (d, 2H, J=8.4 Hz).

Example 31—d$_5$-1-[2-Amino-1-(4-methoxyphenyl)-ethyl]-cyclohexanol

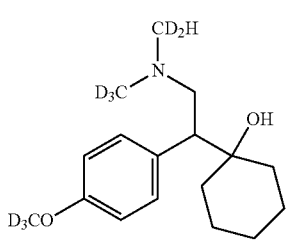

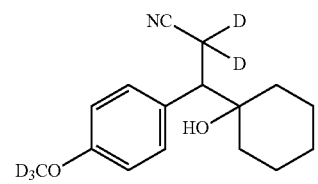

The title compound can be prepared according to the procedure of Example 7, by substituting the water reservoir with a deuterium oxide reservoir for the generation of deuterium gas.

Example 32—(R)-d$_6$-4-[2-Dimethylamino-1-(1-hydroxycyclohexyl)-ethyl]phenol ((R)-d$_6$-O-desmethylvenlafaxine)

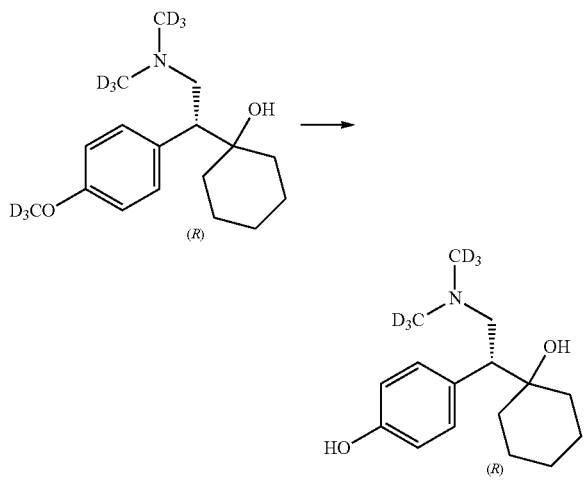

The title compound was prepared from (R)-d$_9$-venlafaxine according to Example 20.

Example 33—(S)-d$_6$-4-[2-Dimethylamino-1-(1-hydroxycyclohexyl)-ethyl]phenol ((S)-d$_6$-O-desmethylvenlafaxine)

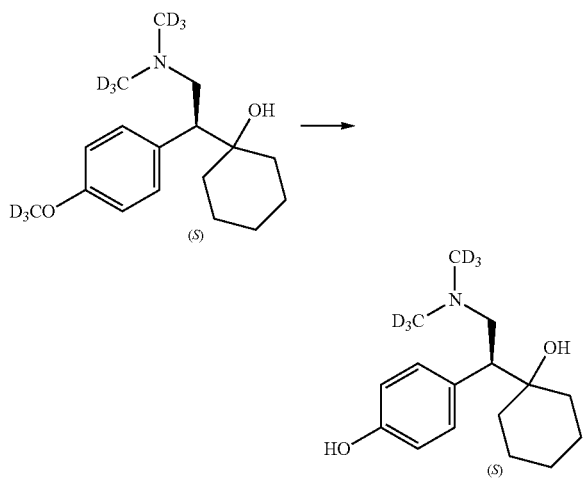

The title compound was prepared from (S)-d$_9$-venlafaxine according to Example 20.

Figure 7:
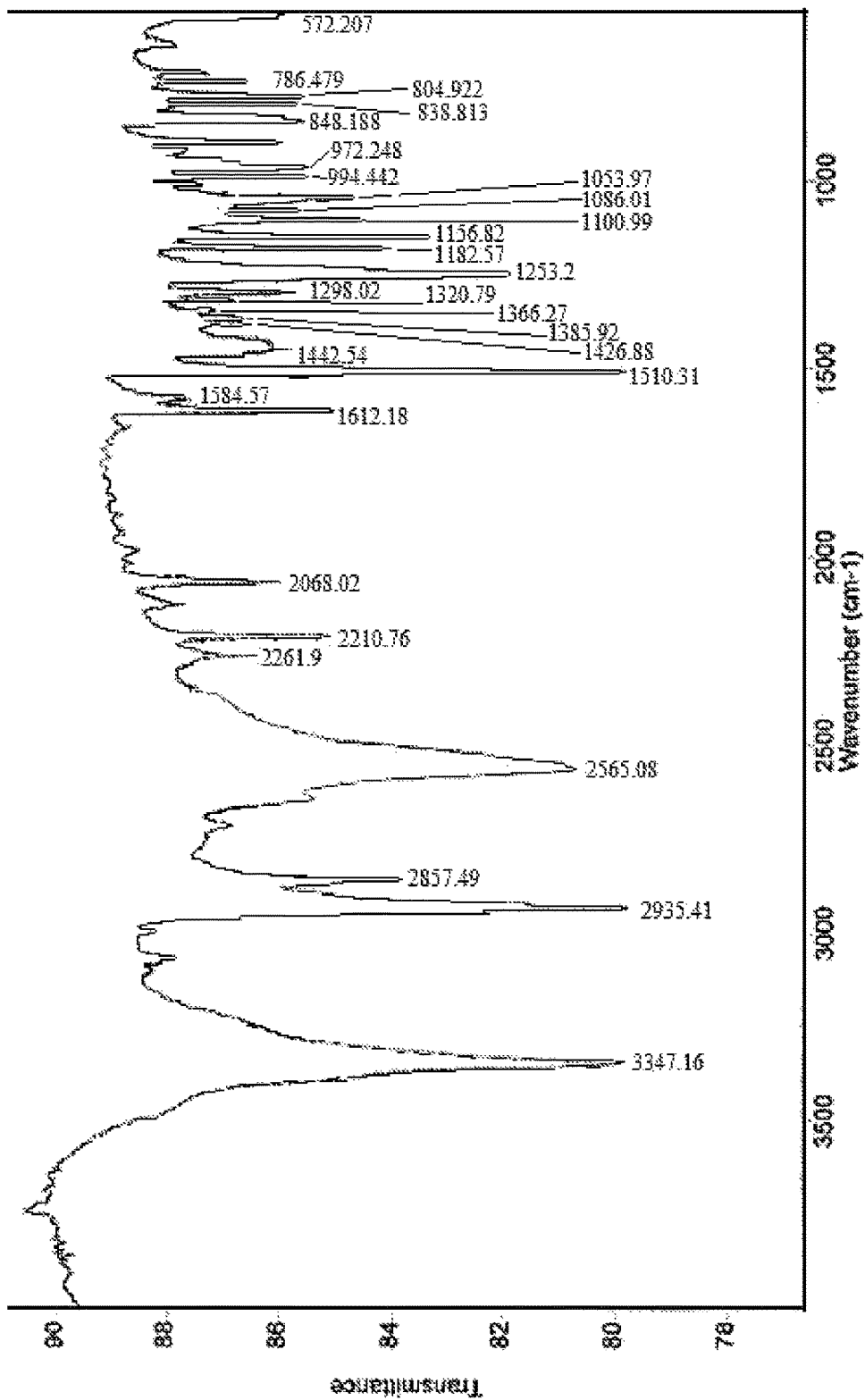
FIG. 7 is a solid state infrared absorption spectrum of $d_9$-1-[2-dimethylamino-1-(4-methoxyphenyl)-ethyl]-cyclohexanol hydrochloride ($d_9$-venlafaxine hydrochloride, Form A) which was prepared and isolated according to the process disclosed in Example 34.

Example 34—d$_9$-1-[2-Dimethylamino-1-(4-methoxyphenyl)-ethyl]-cyclohexanol hydrochloride Form A (d$_9$-venlafaxine hydrochloride Form A)

d$_9$-Venlafaxine hydrochloride (500 mg) was dissolved in isopropanol (8 mL) at about 60° C., and subsequently cooled to 0-5° C. in ice-water bath and kept at that temperature for about 3 hours. The solid was filtered, washed with cold isopropanol and dried under high vacuum to give d$_9$-venlafaxine hydrochloride Form A (248 mg). Characteristic X-ray powder diffraction peaks (2-theta, [% relative intensity]): 6.703 [29.3], 8.321 [19], 12.681 [77.5], 13.5 [47.9], 15.54 [17.7], 18.915 [24.4], 20.359 [100], 21.161 [38.3], 21.762 [26.1], 25.04 [27.8], 28.518 [18.2], and 35.181 [15.5]. A sample of d$_9$-venlafaxine hydrochloride Form A was analyzed by infrared spectroscopy. The results are shown in FIG. 7.

Figure 8:
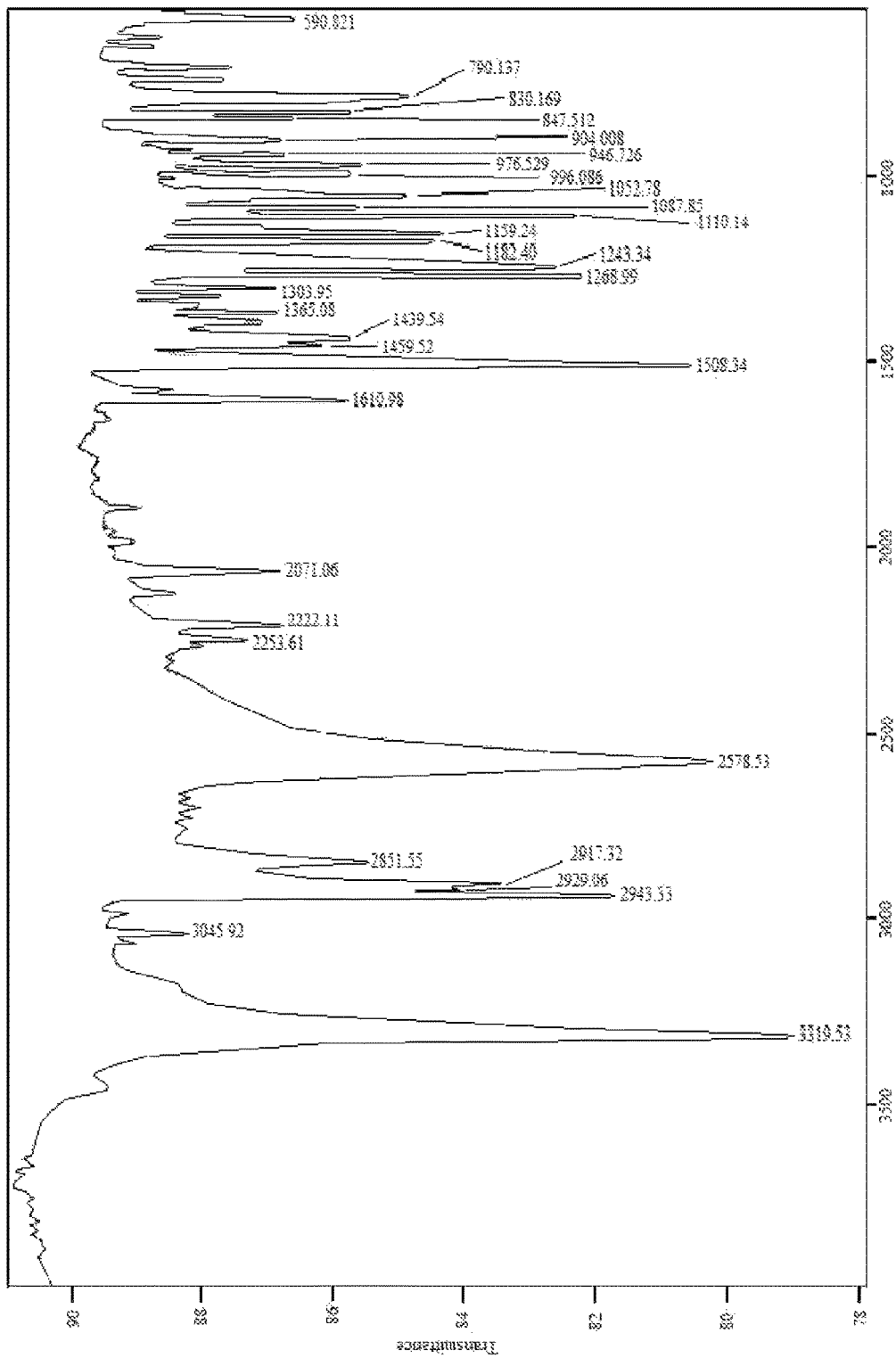
FIG. 8 is a solid state infrared absorption spectrum of $d_9$-1-[2-dimethylamino-1-(4-methoxyphenyl)-ethyl]-cyclohexanol hydrochloride ($d_9$-venlafaxine hydrochloride, Form B) which was prepared and isolated according to the process disclosed in Example 35.
Figure 13:
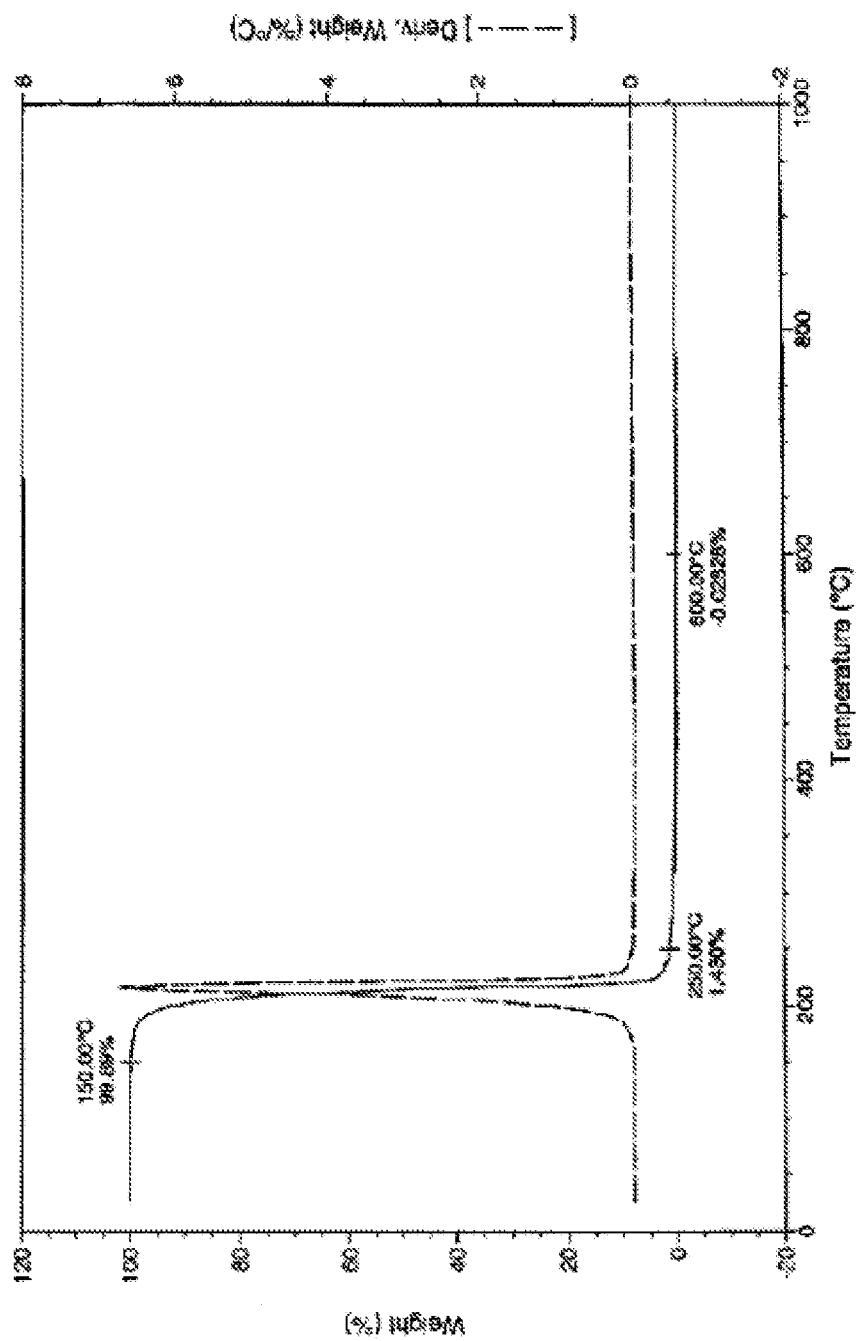
FIG. 13 is a thermogravimetric analysis (TGA) of $d_9$-1-[2-dimethylamino-1-(4-methoxyphenyl)-ethyl]-cyclohexanol hydrochloride ($d_9$-venlafaxine hydrochloride, Form B) which was prepared and isolated according to the process disclosed in Example 35, heated at 10° C./min from ambient temperature to approximately 700° C. and then in regular mode to 1000° C., in a nitrogen atmosphere (25 cc/min).

Example 35—d$_9$-1-[2-Dimethylamino-1-(4-methoxyphenyl)-ethyl]-cyclohexanol hydrochloride Form B (d$_9$-venlafaxine hydrochloride Form B)

d$_9$-Venlafaxine hydrochloride (150 mg) was triturated in a vial with acetone at about 60° C. for about 1 hour and cooled to 0-5° C. for about 1 hour. The solid was filtered, washed with cold acetone and dried at 50° C. on rotary evaporator to a constant weight to give ds-venlafaxine hydrochloride Form B (102 mg). Characteristic X-ray powder diffraction peaks (2-theta, [% relative intensity]): 6.683 [15.5], 10.201 [93.6], 13.441 [27.8], 15.517 [66.2], 18.198 [41], 19.719 [34.1], 20.258 [100], 21.68 [71.2], 22.668 [24.8], 25.543 [22.4], 28.022 [20.9], and 35.02 [33.4]. A sample of d$_9$-venlafaxine hydrochloride Form B was analyzed by infrared spectroscopy. The results are shown in FIG. 8. A sample of d$_9$-venlafaxine hydrochloride Form B was heated at 10° C./min from ambient to approximately 700° C. and then in regular mode to 1000° C., in a nitrogen atmosphere (25 cc/min). The results are shown in FIG. 13.

Example 36—d$_9$-1-[2-Dimethylamino-1-(4-methoxyphenyl)-ethyl]-cyclohexanol hydrochloride Form C (d$_9$-venlafaxine hydrochloride Form C)

Figure 9:
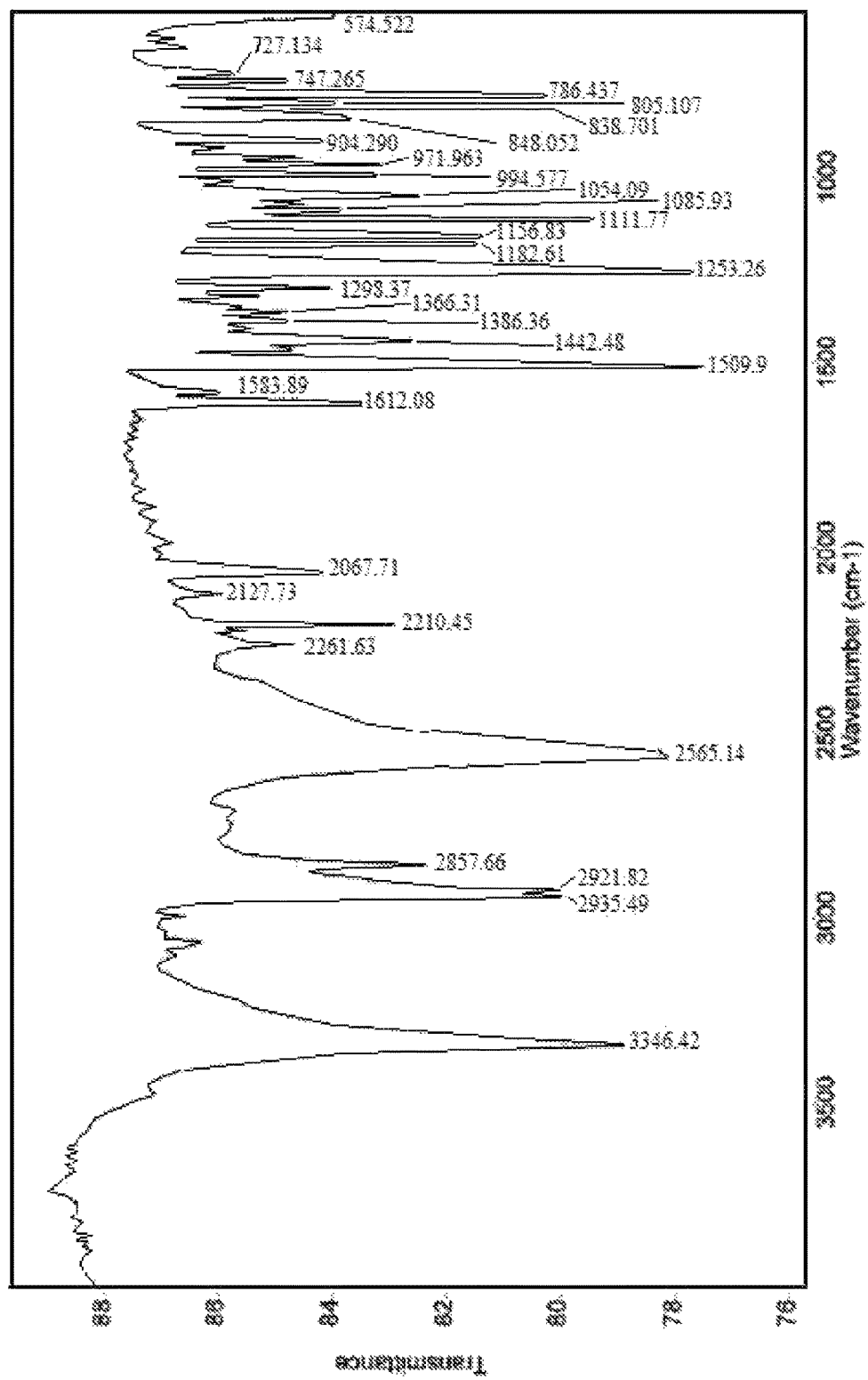
FIG. 9 is a solid state infrared absorption spectrum of $d_9$-1-[2-dimethylamino-1-(4-methoxyphenyl)-ethyl]-cyclohexanol hydrochloride ($d_9$-venlafaxine hydrochloride, Form C) which was prepared and isolated according to the process disclosed in Example 36.
Figure 14:
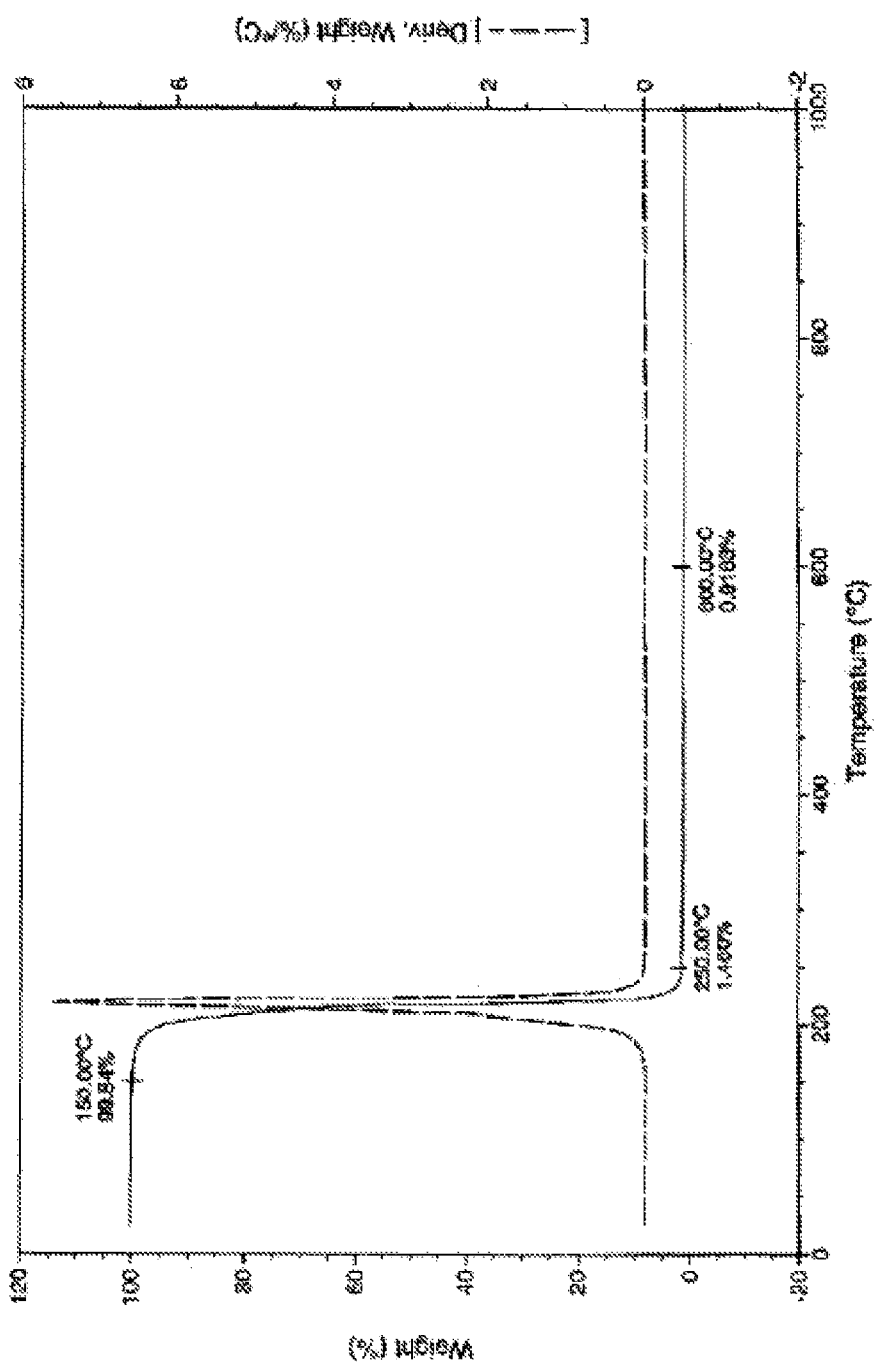
FIG. 14 is a thermogravimetric analysis (TGA) of $d_9$-1-[2-dimethylamino-1-(4-methoxyphenyl)-ethyl]-cyclohexanol hydrochloride ($d_9$-venlafaxine hydrochloride, Form C) which was prepared and isolated according to the process disclosed in Example 36, heated at 10° C./min from ambient to approximately 700° C. and then in regular mode to 1000° C., in a nitrogen atmosphere (25 cc/min).

A slurry of d$_9$-venlafaxine hydrochloride Form A (70 mg) in isopropanol (0.56 mL) was stirred in a vial at ambient temperature for 3 days. The solid was filtered, washed with cold isopropanol and dried under high vacuum to give d$_9$-venlafaxine hydrochloride Form C (30 mg). Characteristic X-ray powder diffraction peaks (2-theta, [% relative intensity]): 6.715 [21.4], 8.385 [20.6], 12.68 [80], 13.5 [40.7], 15.539 [20.2], 16.282 [24.3], 18.902 [48.9], 19.737 [17.4], 20.34 [100], 21.161 [79.4], 21.756 [30.5], 25.02, 25.601 [18.9], 26.231 [15.2], 28.518 [30.2], 31.54 [18.7], 33.156, 33.637 [16.5], and 35.158 [21.3]. A sample of d$_9$-venlafaxine hydrochloride Form C was analyzed by infrared spectroscopy. The results are shown in FIG. 9. A sample of d$_9$-venlafaxine hydrochloride Form C was heated at 10° C./min from ambient to approximately 700° C. and then in regular mode to 1000° C., in a nitrogen atmosphere (25 cc/min). The results are shown in FIG. 14.

Example 37—d$_9$-1-[2-Dimethylamino-1-(4-methoxyphenyl)-ethyl]-cyclohexanol hydrochloride Form D (d$_9$-venlafaxine hydrochloride Form D)

A suspension of d$_9$-venlafaxine hydrochloride (1.45 g) in ether (40 mL) was heated under reflux at 65° C. Methanol was added dropwise to the mixture until it became homogeneous and the solution was cooled to ambient temperature, and kept at that temperature for 1 hour and at 0-5° C. for an additional 3 hours. The solid was filtered and dried under high vacuum to provide d$_9$-venlafaxine hydrochloride Form D (1.08 g). Characteristic X-ray powder diffraction peaks (2-theta, [% relative intensity]): 6.74 [21.2], 7.421 [14], 8.341 [35.5], 10.219 [23], 12.7 [99.5], 13.502 [40.7], 14.9 [17.5], 15.581 [37.3], 20.36 [100], 21.221 [23.7], 21.761 [41], 25.078 [26.3], 31.04 [17.7], and 13.136 [22.7].

Figure 10:
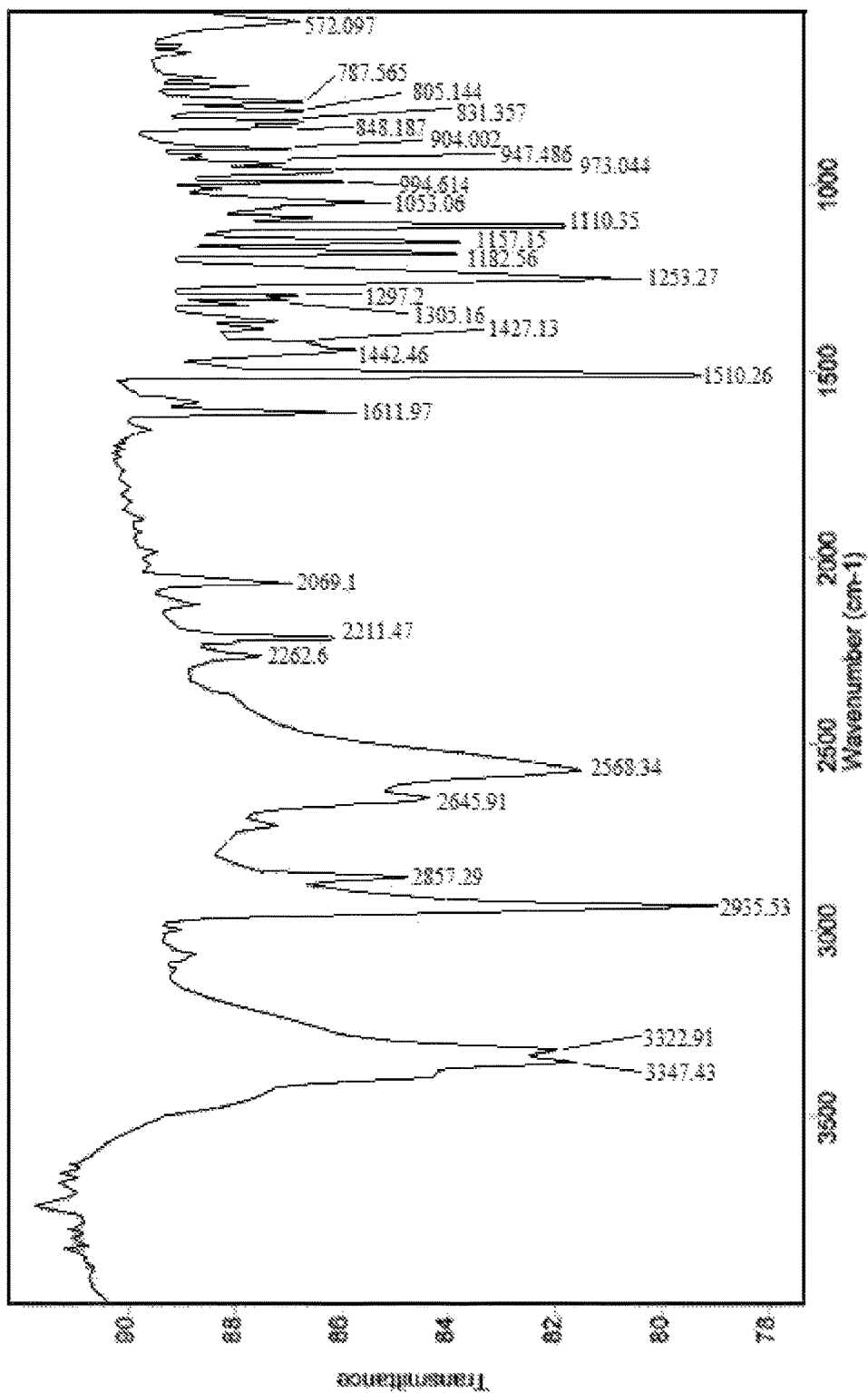
FIG. 10 is a solid state infrared absorption spectrum of $d_9$-1-[2-dimethylamino-1-(4-methoxyphenyl)-ethyl]-cyclohexanol hydrochloride ($d_9$-venlafaxine hydrochloride, Form D) which was prepared and isolated according to the process disclosed in Example 37.

A sample of $d_9$-venlafaxine hydrochloride Form D was analyzed by infrared spectroscopy. The results are shown in FIG. 10.

Example 38—$d_9$-1-[2-Dimethylamino-1-(4-methoxyphenyl)-ethyl]-cyclohexanol hydrochloride Form E ($d_9$-venlafaxine hydrochloride Form E)

Figure 11:
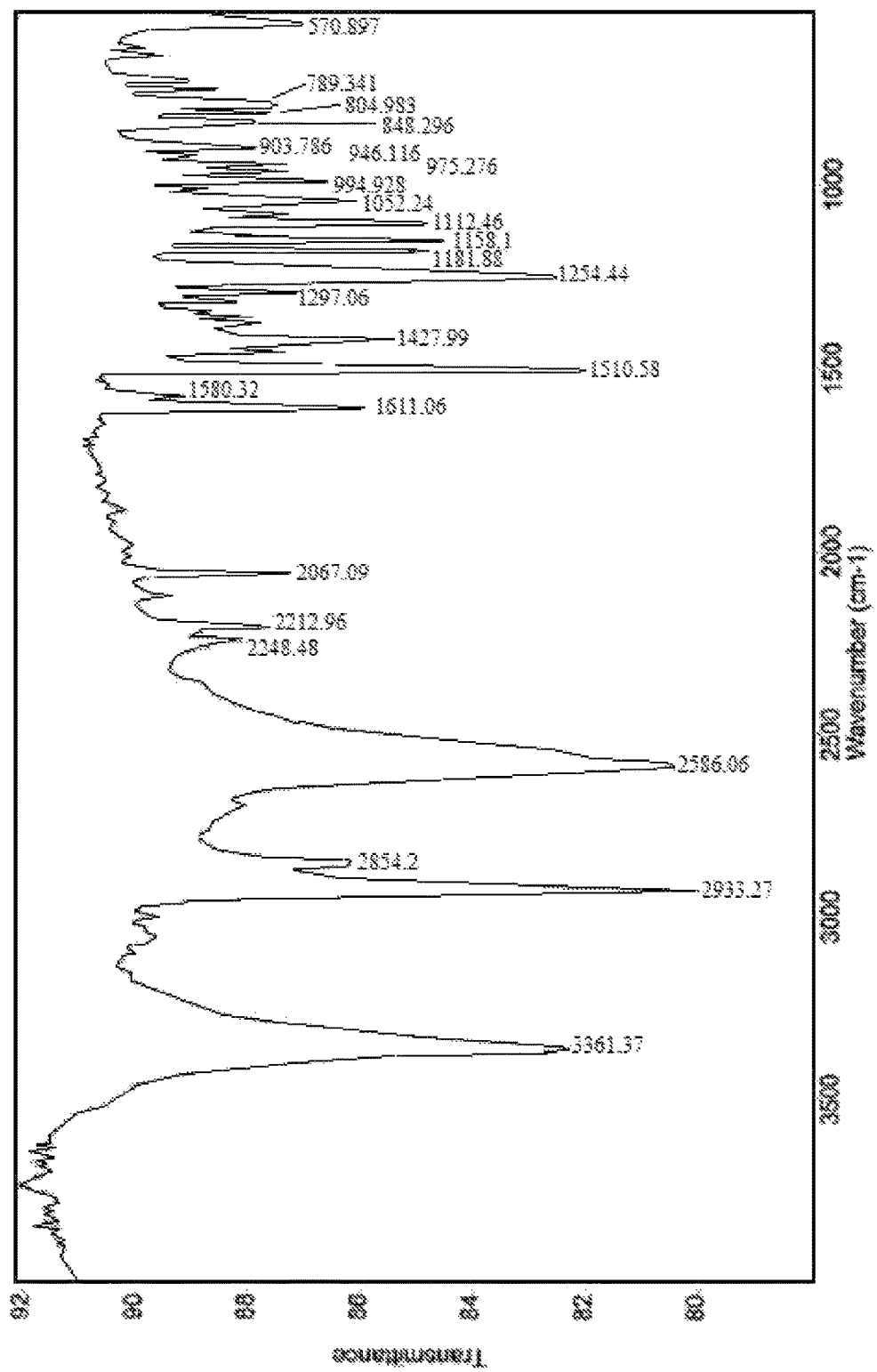
FIG. 11 is a solid state infrared absorption spectrum of $d_9$-1-[2-dimethylamino-1-(4-methoxyphenyl)-ethyl]-cyclohexanol hydrochloride ($d_9$-venlafaxine hydrochloride, Form E) which was prepared and isolated according to the process disclosed in Example 38.
Figure 15:
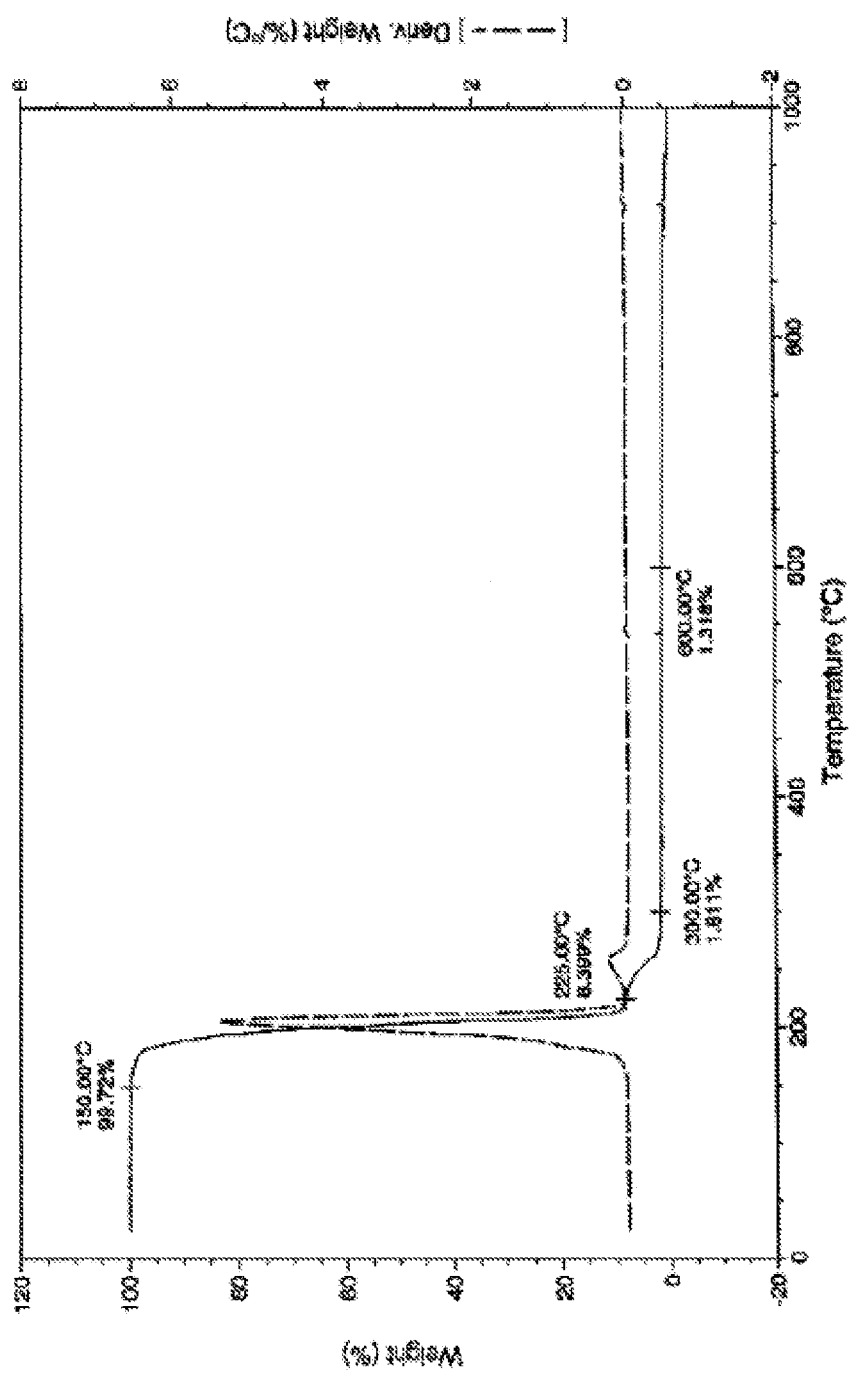
FIG. 15 is a thermogravimetric analysis (TGA) spectrum of $d_9$-1-[2-dimethylamino-1-(4-methoxyphenyl)-ethyl]-cyclohexanol hydrochloride ($d_9$-venlafaxine hydrochloride, Form E) which was prepared and isolated according to the process disclosed in Example 38, heated at 10° C./min from ambient to approximately 700° C. and then in regular mode to 1000° C., in a nitrogen atmosphere (25 cc/min).

$d_9$-Venlafaxine hydrochloride Form D (98 mg) was heated in a sealed tube for 1.5 hours at 200-200° C. and cooled to ambient temperature. Characteristic X-ray powder diffraction peaks (2-theta, [% relative intensity]): 5.527 [28], 7.162 [36.2], 9.075 [24.1], 9.567 [14.9], 11.201 [100], 14.45 [40.2], 14.76 [40.4], 16.86 [71.7], 17.467 [15.7], 19.201 [66.5], 19.619 [19.6], 20.241 [35.2], 20.65 [19.6], 21.76 [22.5], 22.695 [26.4], 23.05 [13.2], 24.4 [15.3], 25.02, 26.519, 26.642 [18.7], 31.52 [12.6], and 35.435 [17.9]. A sample of $d_9$-venlafaxine hydrochloride Form E was analyzed by infrared spectroscopy. The results are shown in FIG. 11. A sample of $d_9$-venlafaxine hydrochloride Form E was heated at 10° C./min from ambient to approximately 700° C. and then in regular mode to 1000° C., in a nitrogen atmosphere (25 cc/min). The results are shown in FIG. 15.

Example 39—$d_9$-1-[2-Dimethylamino-1-(4-methoxyphenyl)-ethyl]-cyclohexanol hydrochloride Form F ($d_9$-venlafaxine hydrochloride Form F)

Figure 12:
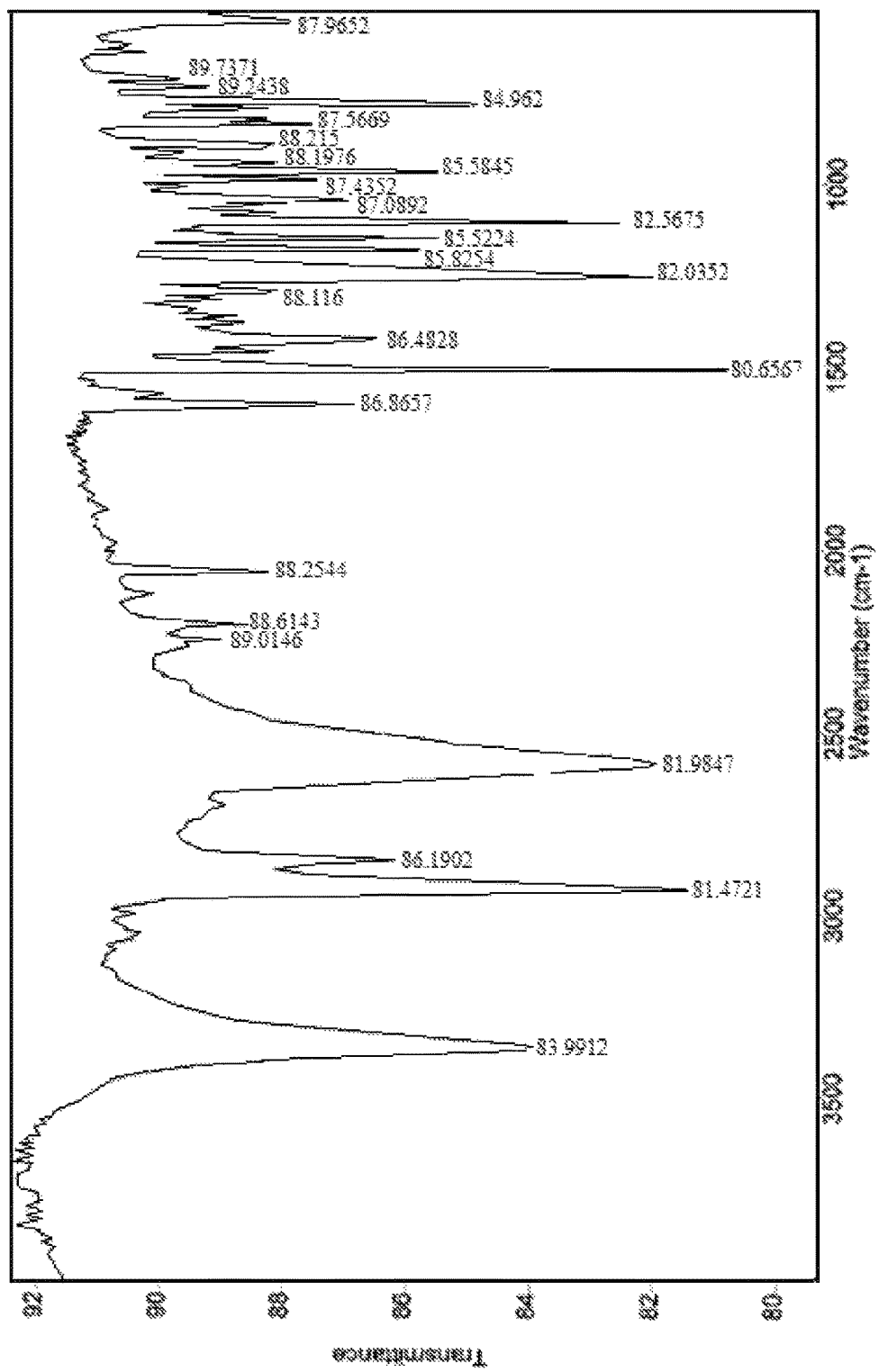
FIG. 12 is a solid state infrared absorption spectrum of $d_9$-1-[2-dimethylamino-1-(4-methoxyphenyl)-ethyl]-cyclohexanol hydrochloride ($d_9$-venlafaxine hydrochloride, Form F) which was prepared and isolated according to the process disclosed in Example 39.

$d_9$-Venlafaxine hydrochloride Form A (68 mg) was heated at 205° C. for 2 hours and cooled to ambient temperature. The crystals that formed at the top of the flask were collected. Characteristic X-ray powder diffraction peaks (2-theta, [% relative intensity]): 5.581 [26.1], 7.183 [18.3], 11.22 [100], 14.499 [18.8], 14.802 [20.5], 16.662 [63.9], 19.242 [38.4], 20.317 [51.6], 21.728 [17.5], 22.637 [26.3], and 35.445 [16.2]. A sample of $d_9$-venlafaxine hydrochloride Form F was analyzed by infrared spectroscopy. The results are shown in FIG. 12.

Example 40—In Vitro Liver Microsomal Stability Assay

Liver microsomal stability assays were conducted at 1 mg per mL liver microsome protein with an NADPH-generating system in 2% NaHCO$_3$ (2.2 mM NADPH, 25.6 mM glucose 6-phosphate, 6 units per mL glucose 6-phosphate dehydrogenase and 3.3 mM MgCl$_2$). Test compounds were prepared as solutions in 20% acetonitrile-water and added to the assay mixture (final assay concentration 5 microgram per mL) and incubated at 37° C. Final concentration of acetonitrile in the assay were <1%. Aliquots (50 µL) were taken out at times 0, 15, 30, 45, and 60 minutes, and diluted with ice cold acetonitrile (200 µL) to stop the reactions. Samples were centrifuged at 12000 RPM for 10 minutes to precipitate proteins. Supernatants were transferred to microcentrifuge tubes and stored for LC/MS/MS analysis of the degradation half-life of the test compounds. It has thus been found that the compounds as disclosed herein that have been tested in this assay showed an increase of 10% or more in the degradation half-life, as compared to the non-isotopically enriched drug. For example, the degradation half-life of (±)-$d_3$-venlafaxine, (R)-$d_3$-venlafaxine, (S)-$d_3$-venlafaxine, (±)-$d_8$-venlafaxine, (±)-$d_9$-venlafaxine, (R)-$d_9$-venlafaxine, (S)-$d_9$-venlafaxine, $d_{14}$-venlafaxine, and $d_{20}$-venlafaxine were increased by 50-300% as compared to non-isotopically enriched venlafaxine.

Example 41—In Vitro Metabolism Using Human Cytochrome P$_{450}$ Enzymes

The cytochrome P$_{450}$ enzymes are expressed from the corresponding human cDNA using a baculovirus expression system (BD Biosciences). A 0.25 milliliter reaction mixture containing 0.8 milligrams per milliliter protein, 1.3 millimolar NADP$^+$, 3.3 millimolar glucose-6-phosphate, 0.4 U/mL glucose-6-phosphate dehydrogenase, 3.3 millimolar magnesium chloride and 0.2 millimolar of a compound of Formula I, the corresponding non-isotopically enriched compound or standard or control in 100 millimolar potassium phosphate (pH 7.4) is incubated at 37° C. for 20 min. After incubation, the reaction is stopped by the addition of an appropriate solvent (e.g. acetonitrile, 20% trichloroacetic acid, 94% acetonitrile/6% glacial acetic acid, 70% perchloric acid, 94% acetonitrile/6% glacial acetic acid) and centrifuged (10,000 g) for 3 minutes. The supernatant is analyzed by HPLC/MS/MS.

| Cytochrome P$_{450}$ | Standard |
|---|---|
| CYP1A2 | Phenacetin |
| CYP2A6 | Coumarin |
| CYP2B6 | [$^{13}$C]-(S)-mephenytoin |
| CYP2C8 | Paclitaxel |
| CYP2C9 | Diclofenac |
| CYP2C19 | [$^{13}$C]-(S)-mephenytoin |
| CYP2D6 | (+/−)-Bufuralol |
| CYP2E1 | Chlorzoxazone |
| CYP3A4 | Testosterone |
| CYP4A | [$^{13}$C]-Lauric acid |

Example 42—Monoamine Oxidase A Inhibition and Oxidative Turnover

The procedure is carried out as described in Weyler, *Journal of Biological Chemistry* 1985, 260, 13199-13207. Monoamine oxidase A activity is measured spectrophotometrically by monitoring the increase in absorbance at 314 nm on oxidation of kynuramine with formation of 4-hydroxyquinoline. The measurements are carried out, at 30° C., in 50 mM NaP$_i$ buffer, pH 7.2, containing 0.2% Triton X-100 (monoamine oxidase assay buffer), plus 1 mM kynuramine, and the desired amount of enzyme in 1 mL total volume.

Example 43—Monoamine Oxidase B Inhibition and Oxidative Turnover

The procedure is carried out as described in Uebelhack, *Pharmacopsychiatry* 1998, 31, 187-192.

Pharmacology

The pharmacological profile of compounds of Formula I or the corresponding non-isotopically enriched compounds or standards or controls can be demonstrated as follows. The preferred exemplified compounds exhibit a K$_i$ value less than 1 micromolar, more preferably less than 500 nanomolar at the Serotonin transporter as determined using the scintillation proximity assay (SPA) described below. See WO 2005/060949. Furthermore, the preferred exemplified compounds selectively inhibit the Serotonin transporter relative to the Norepinephrine and dopamine transporters by a factor of at least five using such SPAs.

Example 44—Generation of Stable Cell Lines Expressing the Human Dopamine, Norepinephrine and Serotonin Transporters Standard molecular cloning techniques are used to generate stable cell-lines expressing the human dopamine, norepinephrine and serotonin transporters. The polymerase chain reaction (PCR) is used in order to isolate and amplify each of the three full-length cDNAs from an appropriate cDNA library. PCR Primers for the following neurotransmitter transporters are designed using published sequence data. The PCR products are cloned into a mammalian expression vector, such as for example pcDNA3.1 (Invitrogen), using standard ligation techniques, followed by co-transfection of HEK293 cells using a commercially available lipofection reagent (Lipofectamine™—Invitrogen) following the manufacturer's protocol.

Human Dopamine transporter: GenBank M95167. Vandenbergh et al, *Molecular* Brain Research 1992, 15, 161-166, which is hereby incorporated by reference in its entirety.

Human Norepinephrine transporter: GenBank M65105. Pacholczyk et al, *Nature* 1991, 350, 350-354, which is hereby incorporated by reference in its entirety.

Human Serotonin transporter: GenBank L05568. Ramamoorthy et al, *Proceedings of the National Academy of Sciences of the USA* 1993, 90, 2542-2546, which is hereby incorporated by reference in its entirety.

Example 45—In Vitro SPA Binding Assay for the Norepinephrine Transporter

The assay is preformed according to the procedure described in Gobel et al, *Journal of Pharmacological and Toxicological Methods* 1999, 42(4), 237-244, which is hereby incorporated by reference in its entirety. Compound of Formula I or the corresponding non-isotopically enriched compounds are serotonin/norepinephrine reuptake inhibitors; $^3$H-nisoxetine binding to norepinephrine re-uptake sites in a cell line transfected with DNA encoding human norepinephrine transporter binding protein has been used to determine the affinity of ligands at the norepinephrine transporter.

Membrane Preparation

Cell pastes from large scale production of HEK-293 cells expressing cloned human norepinephrine transporters are homogenized in 4 volumes of 50 millimolar Tris-HCl containing 300 millimolar NaCl and 5 millimolar KCl, pH 7.4. The homogenate is centrifuged twice (40,000 g, 10 minutes, 4° C.) with pellet re-suspension in 4 volumes of Tris-HCl buffer containing the above reagents after the first spin, and 8 volumes after the second spin. The suspended homogenate is centrifuged (100 g, 10 minutes, 4° C.), the supernatant is kept and re-centrifuged (40,000 g, 20 minutes, 4° C.). The pellet is re-suspended in Tris-HCl buffer containing the above reagents along with 10% w/v sucrose and 0.1 millimolar phenylmethylsulfonyl fluoride (PMSF). The membrane preparation is stored in aliquots (1.0 milliliter) at −80° C. until required. The protein concentration of the membrane preparation is determined using a Bicinchoninic acid (BCA) protein assay reagent kit (available from Pierce).

[$^3$H]-Nisoxetine Binding Assay

Each well of a 96 well microtiter plate is set up to contain 50 microliters of 2 nanomolar [N-methyl-$^3$H]-Nisoxetine hydrochloride (70-87 Ci/millimole, from NEN Life Science Products), 75 microliters Assay buffer (50 millimolar Tris-HCl pH 7.4 containing 300 millimolar NaCl and 5 millimolar KCl), 25 microliter of diluted compounds of Formula I or the corresponding non-isotopically enriched compounds, assay buffer (total binding) or 10 micromolar Desipramine HCl (non-specific binding), 50 microliter wheat germ agglutinin coated poly(vinyltoluene) (WGA PVT) SPA Beads (Amersham Biosciences RPNQ0001) (10 milligram/milliliter), 50 microliter membrane (0.2 milligram protein per milliliter). The microtiter plates are incubated at room temperature for 10 hours prior to reading in a Trilux scintillation counter. The results are analyzed using an automatic spline-fitting program (Multicalc, Packard, Milton Keynes, UK) to provide $K_i$ values for each of the test compounds.

Example 46—In Vitro SPA Binding Assay for the Serotonin Transporter

The assay is preformed according to the procedure described in Ramamoorthy et al, *J. Biol. Chem.* 1998, 273(4), 2458-2466, which is hereby incorporated by reference in its entirety. The ability of a compound of Formula I or the corresponding non-isotopically enriched compound to compete with [$^3$H]-Citalopram for its binding sites on cloned human Serotonin transporter containing membranes has been used as a measure of test compound ability to block Serotonin uptake via its specific transporter.

Membrane Preparation

Membrane preparation is essentially similar to that for the norepinephrine transporter containing membranes as described above. The membrane preparation is stored in aliquots (1 milliliter) at −70° C. until required. The protein concentration of the membrane preparation is determined using a BCA protein assay reagent kit.

[$^3$H]-Citalopram Binding Assay

Each well of a 96 well microtiter plate is set up to contain 50 microliters of 2 nanomolar [$^3$H]-citalopram (60-86 Ci/millimole, Amersham Biosciences), 75 microliters Assay buffer (50 millimolar Tris-HCl pH 7.4 containing 150 millimolar NaCl and 5 millimolar KCl), 25 microliters of diluted compounds of Formula I or the corresponding non-isotopically enriched compounds, assay buffer (total binding) or 100 micromolar fluoxetine (non-specific binding), 50 microliters WGA PVT SPA Beads (40 milligram/milliliter), 50 microliters membrane preparation (0.4 milligram protein per milliliter). The microtiter plates are incubated at room temperature for 10 hours prior to reading in a Trilux scintillation counter. The results are analyzed using an automatic spline-fitting program (Multicalc, Packard, Milton Keynes, UK) to provide $K_i$ (nanomolar) values for each of the test compounds.

Example 47—In Vitro SPA Binding Assay for the Dopamine Transporter

The assay is preformed according to the procedure described in Ramamoorthy et al, *J. Biol. Chem.* 1998, 273(4), 2458-2466, which is hereby incorporated by reference in its entirety. The ability of a test compound to compete with [$^3$H]-WIN35,428 for its binding sites on human cell membranes containing cloned human dopamine transporter has been used as a measure of the ability of such test compounds to block dopamine uptake via its specific transporter.

Membrane Preparation

Membrane preparation is performed in the same manner as membranes containing cloned human Serotonin transporter as described above.

[$^3$H]-WIN35,428 Binding Assay

Each well of a 96 well microtiter plate is set up to contain 50 microliters of 4 nanomolar [$^3$H]-WIN35,428 (84-87 Ci/millimole, from NEN Life Science Products), 5 microliters Assay buffer (50 millimolar Tris-HCl pH 7.4 containing 150 millimolar NaCl and 5 millimolar KCl), 25 microliters of diluted compounds of Formula I or the corresponding non-isotopically enriched compounds, assay buffer (total binding) or 100 micromolar nomifensine (non-specific binding), 50 microliters WGA PVT SPA Beads (10 milligram/milliliter), 50 microliters membrane preparation (0.2 milligram protein per milliliter). The microtiter plates are incubated at room temperature for 120 minutes prior to reading in a Trilux scintillation counter. The results are analyzed using an automatic spline-fitting program (Multicalc, Packard, Milton Keynes, UK) to provide $K_i$ values for each of the test compounds.

Example 48—In Vivo Assay for Behavioral Despair in Rats

The assay is performed according to the procedure described in Porsolt et al, *Archives Internationales de Pharmacodynamie et de Therapie*, 1977, 229(2), 327-336. which is hereby incorporated by reference in its entirety. After intraperitoneal administration of test compound in rats, animals are put in a cylinder containing water for 6 minutes. Immobility time is measured during the last 4 minutes. Diminished time of immobility is indicative of increased efficacy.

The examples set forth above are disclosed to give a complete disclosure and description of how to make and use the claimed embodiments, and are not intended to limit the scope of what is disclosed herein. Modifications that are obvious, are intended to be within the scope of the following claims. All publications, patents, and patent applications cited in this specification are incorporated herein by reference as if each such publication, patent or patent application were specifically and individually indicated to be incorporated herein by reference. However, with respect to any similar or identical terms found in both the incorporated publications, references, patent or patent applications and those explicitly put forth or defined in this document, then those terms definitions or meanings explicitly put forth in this document shall control in all respects.

REFERENCES CITED

The disclosures of each of the following references are incorporated by reference herein in their entireties.

Patent Documents

U.S. Pat. No. 4,069,346 Feb. 14, 1977 McCarty
U.S. Pat. No. 5,386,032 Jan. 31, 1995 Brandstrom
EP0654264 May 24, 1995 Thor
U.S. Pat. No. 5,846,514 Dec. 8, 1998 Foster
U.S. Pat. No. 6,221,335 Apr. 24, 2001 Foster
U.S. Pat. No. 6,333,342 Dec. 25, 2001 Foster
U.S. Pat. No. 6,334,997 Jan. 1, 2002 Foster
U.S. Pat. No. 6,342,507 Jan. 29, 2002 Foster
U.S. Pat. No. 6,476,058 Nov. 5, 2002 Foster
U.S. Pat. No. 6,503,921 Jan. 7, 2003 Naicker
U.S. Pat. No. 6,605,593 Aug. 12, 2003 Naicker
U.S. Pat. No. 6,613,739 Sep. 2, 2003 Naicker
U.S. Pat. No. 6,710,053 Mar. 23, 2004 Naicker
U.S. Pat. No. 6,818,200 Nov. 16, 2004 Foster
U.S. Pat. No. 6,884,429 Apr. 26, 2005 Koziak
WO 2002064543 Aug. 22, 2002 Hadfield Other References Altermatt, *Cancer* 1988, 62(3), 462-466.
Altermatt, *International Journal of Cancer* 1990, 45(3), 475-480.
Baldwin, *International Journal of Neuropsychopharmacology* 2005, 8(2), 293-302.
Baselt, *Disposition of Toxic Drugs and Chemicals in Man*, 2004, 7th Edition.
Bassapa et al, *Bioorganic & Medicinal Chemistry Letters* 2004, 14, 3279-3281.
Browne, *Synthesis and Applications of Isotopically Labelled Compounds, Proceedings of the International Symposium*, 7th, Dresden, Germany, Jun. 18-22, 2000, 519-532.
Browne, *Pharmacochemistry Library*, 1997, 26.
Browne, *Pharmacochemistry Library*, 1997, 26, 13-18.
Browne, *Clinical Pharmacology & Therapeutics*, 1981, 29(4), 511-515.
Browne, *Journal of Clinical Pharmacology* 1982, 22(7), 309-315.
Browne, *Synth. Appl. Isot. Labeled Compd., Proc. Int. Symp.* 1983, Meeting Date 1982, 343-348.
Browne, *Therapeutic Drug Monitoring* 1984, 6(1), 3-9.
Chavan et al, *Tetrahedron Letters* 2004, 45, 7291-7295.
Davies et al, *Journal of the Chemical Society, Abstracts* 1945, 352-354.
Ding et al *Journal of Neurochemistry* 1995, 65(2), 682-690.
Eap et al, *Pharmacogenetics* 2002, 13, 39-47.
Foster, *Trends in Pharmacological Sciences* 1984, 5(12), 524-527.
Garland, *Synth. Appl. Isot. Labeled Compd. Proc. Int. Symp.* $2^{nd}$, 1986, Meeting Date 1985, 283-284.
Gobel et al, *Journal of Pharmacological and Toxicological Methods* 1999, 42(4), 237-244
Goeringer, *Journal of Forensic Sciences* 2000, 45(3), 633-648.
Katzman, *Expert Review of Neurotherapeutics*, 2005, 5(1), 129-139.
Kaufman, *Phys. Rev.* 1954, 93, 1337-1344.
Ko et al *British Journal of Clinical Pharmacology* 2000, 49(4), 343-351.
Kritchevsky, *Annals of the New York Academy of Science* 1960, vol. 84, article 16.
Kushner, *Can. J. Physiol. Pharmacol.* 1999, 77, 79-88.
Lamprect, *European Journal of Cell Biology* 1990, 51(2), 303-312.
Lessard et al, *Pharmacogenetics* 1999, 9(4), 435-443.
Lewis, *J. Am. Chem. Soc.* 1968, 90, 4337.
Li et al *Rapid Communications in Mass Spectrometry* 2005, 19(14), 1943-1950
March, *Advanced Organic Chemistry* 1992, 4th edition, 226-230.
Morton et al, *Annals of Pharmacotherapy* 1995, 29(4), 387-395.
Ouk et al *Green Chemistry*, 2002, 4(5), 431-435.
Pacher, *Current Medicinal Chemistry* 2004, 11(7), 925-943.
Pacher et al, *Current Pharmaceutical Design* 2004, 10(20), 2463-2475.
Pacholczyk et al, *Nature* 1991, 350, 350-354.
Phelps et al, *Annals of Pharmacotherapy* 2005, 39(1), 136-140.
Physicians Desk Reference, 2003.
Porsolt et al, *Archives Internationales de Pharmacodynamie et de Therapie*, 1977, 229(2), 327-336.
Pohl, *Drug Metabolism Reviews* 1985 (Volume Date 1984), 15(7), 1335-1351.

Preskorn et al, *Handbook of Experimental Pharmacology. Antidepressants: Past, Present and Future*, 2004, Volume 157.

Raggi, *Current Topics in Medicinal Chemistry* 2003, 3, 203-220.

Ramamoorthy et al, *J. Biol. Chem.* 1998, 273(4), 2458-2466.

Ramamoorthy et al, *Proceedings of the National Academy of Sciences of the USA* 1993, 90, 2542-2546.

Reis et al, *Therapeutic Drug Monitoring* 2002, 24, 545-553.

Roecker, *J. Am. Chem. Soc.* 1987, 109, 746.

Schroeter, *European Journal of Cell Biology* 1992, 58(2), 365-370.

Sicat et al, *Pharmacotherapy* 2004, 24(1), 79-93.

Silverstone, *Journal of Clinical Psychiatry* 2004, 65(Suppl. 17), 19-28.

Tolonen, *European Journal of Pharmaceutical Sciences* 2005, 25, 155-162.

Thomson, *International Series of Monographs on Pure and Applied Biology, Modern trends in Physiological Sciences*, 1963, "Biological Effects of Deuterium".

Urey, *Phys. Rev.* 1932, 39, 164 "A Hydrogen Isotope of Mass 2".

Vandenbergh et al, *Molecular Brain Research* 1992, 15, 161-166.

Yardley et al, *Journal of Medicinal Chemistry* 1990, 33(10), 2899-2905.

What is claimed is:

1. Polymorph Form B of $d_9$-1-[2-dimethylamino-1-(4-methoxyphenyl)-ethyl]-cyclohexanol hydrochloride ($d_9$-venlafaxine hydrochloride) having the formula:

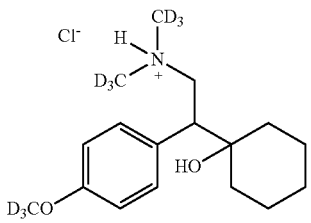

wherein:
each position designated as D has a deuterium enrichment of no less than 1% above the naturally occurring distribution of deuterium; and
said polymorph produces an X-ray powder diffraction spectrum comprising peaks at diffraction angles (2θ±5%) of 6.683, 10.201, 13.441, 15.517, 18.198, 19.719, 20.258, 21.68, 22.668, 25.543, 28.022, and 35.02.

2. The Polymorph Form B of $d_9$-1-[2-dimethylamino-1-(4-methoxyphenyl)-ethyl]-cyclohexanol hydrochloride ($d_9$-venlafaxine hydrochloride) as recited in claim 1, wherein said X-ray powder diffraction spectrum further comprises one or more peaks at diffraction angles (2θ±5%) of 16.64, 17.206, 23.923, 25.322, 26.502, 27.122, 27.567, 28.64, 29.241, 29.650, 31.079, 31.379, 31.978, 32.260, 32.701, 32.961, 34.12, 36.024, 36.842, 37.5, or 38.341.

3. A pharmaceutical composition comprising the compound as recited in claim 1 and one or more pharmaceutically acceptable carriers.

4. The pharmaceutical composition as recited in claim 3, further comprising one or more release-controlling carriers.

5. The pharmaceutical composition as recited in claim 3, further comprising one or more non-release controlling carriers.

6. The pharmaceutical composition as recited in claim 3, wherein the composition is suitable for oral, parenteral, or intravenous infusion administration.

7. The pharmaceutical composition as recited in claim 6, wherein the oral dosage form is a tablet or capsule.

8. The pharmaceutical composition as recited in claim 3, wherein the compound is administered in a dose of about 0.5 milligrams to about 1,000 milligrams.

9. The pharmaceutical composition as recited in claim 3, wherein the compound is administered in a dose of about 0.5 milligrams to about 400 milligrams.

Figure 2:
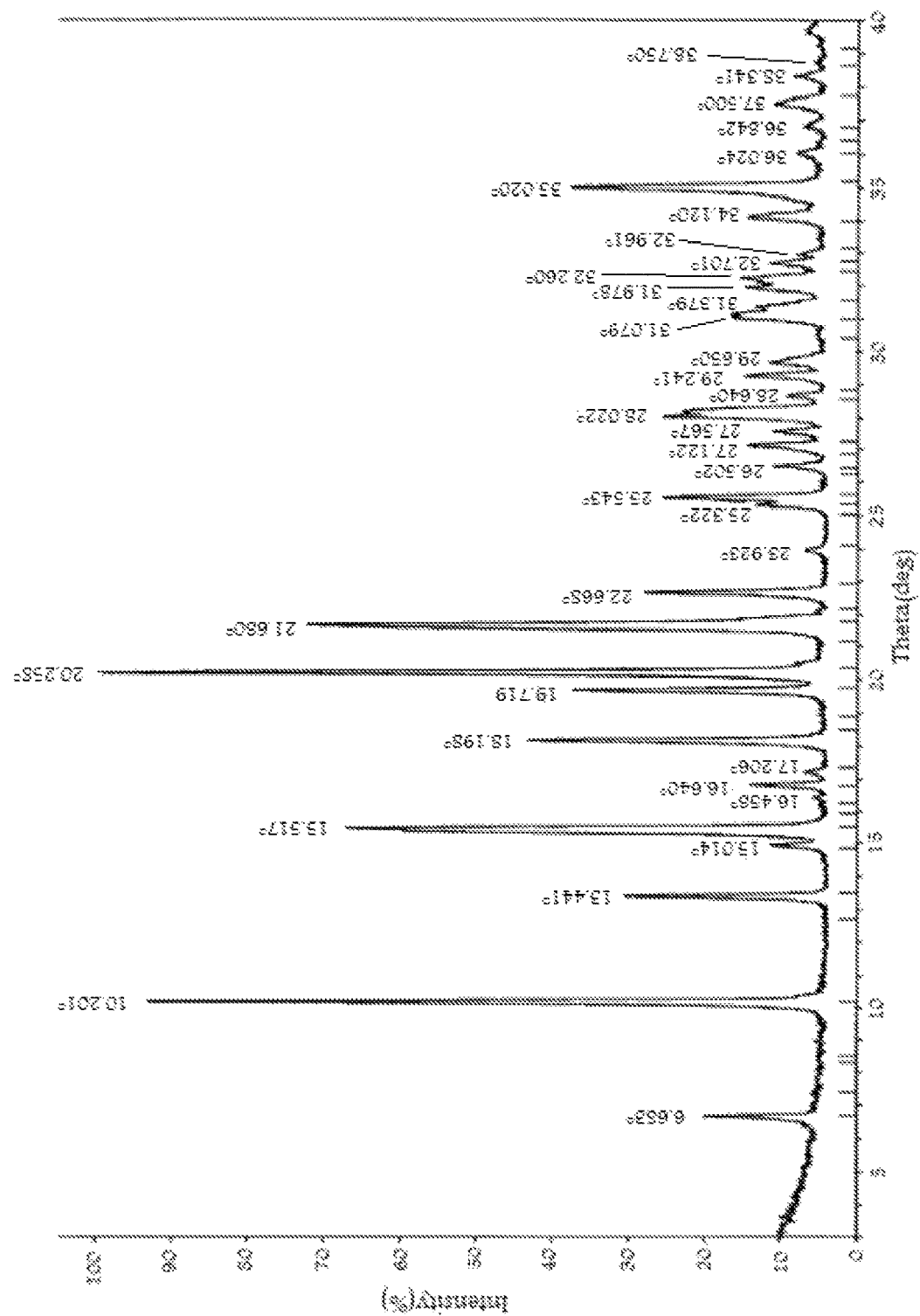
FIG. 2 is an X-ray powder diffraction spectrum of $d_9$-1-[2-dimethylamino-1-(4-methoxyphenyl)-ethyl]-cyclohexanol hydrochloride ($d_9$-venlafaxine hydrochloride, Form B) which was prepared and isolated according to the process disclosed in Example 35.
Figure 3:
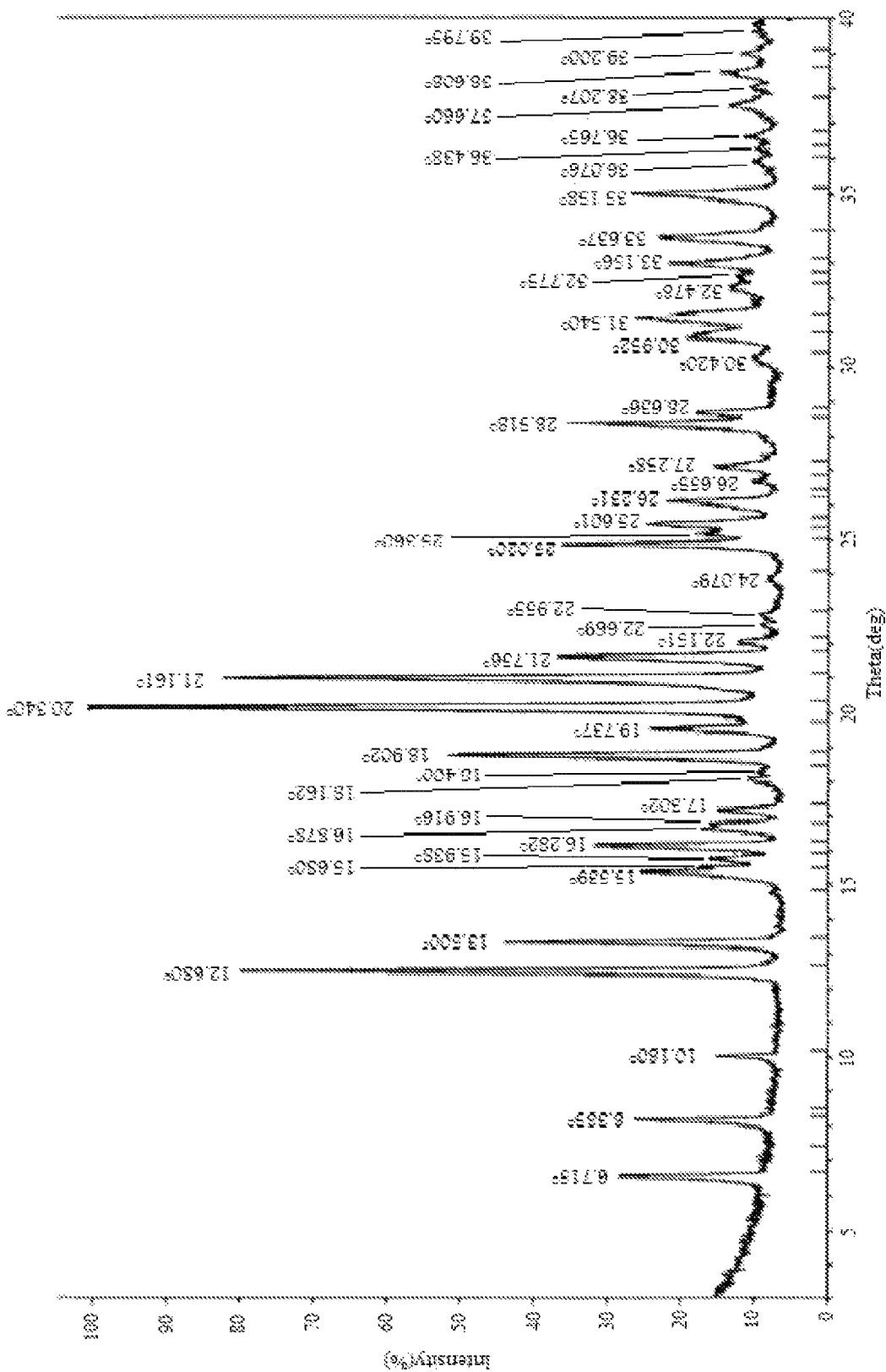
FIG. 3 is an X-ray powder diffraction spectrum of $d_9$-1-[2-dimethylamino-1-(4-methoxyphenyl)-ethyl]-cyclohexanol hydrochloride ($d_9$-venlafaxine hydrochloride, Form C) which was prepared and isolated according to the process disclosed in Example 36.
Figure 4:
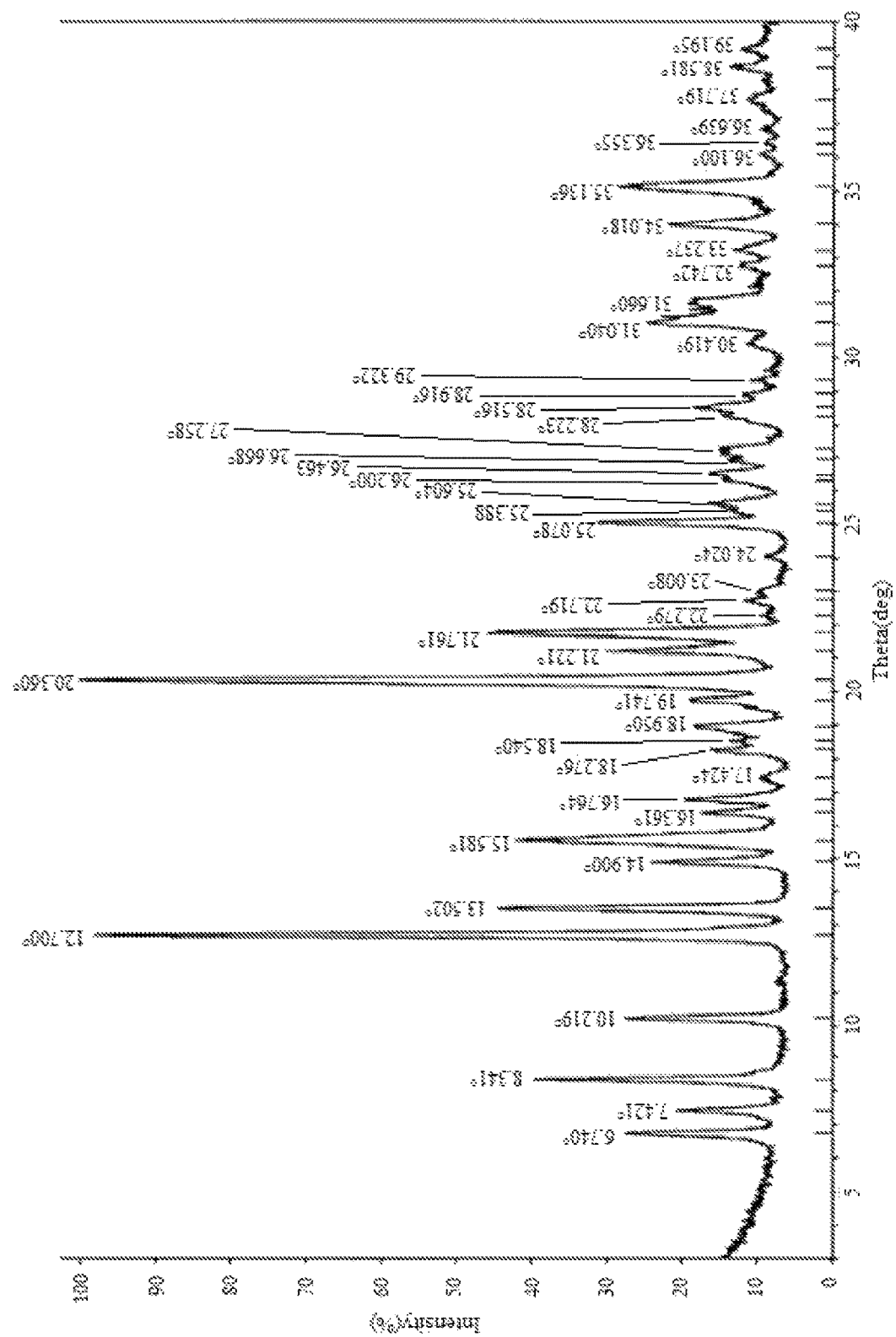
FIG. 4 is an X-ray powder diffraction spectrum of $d_9$-1-[2-dimethylamino-1-(4-methoxyphenyl)-ethyl]-cyclohexanol hydrochloride ($d_9$-venlafaxine hydrochloride, Form D) which was prepared and isolated according to the process disclosed in Example 37.
Figure 5:
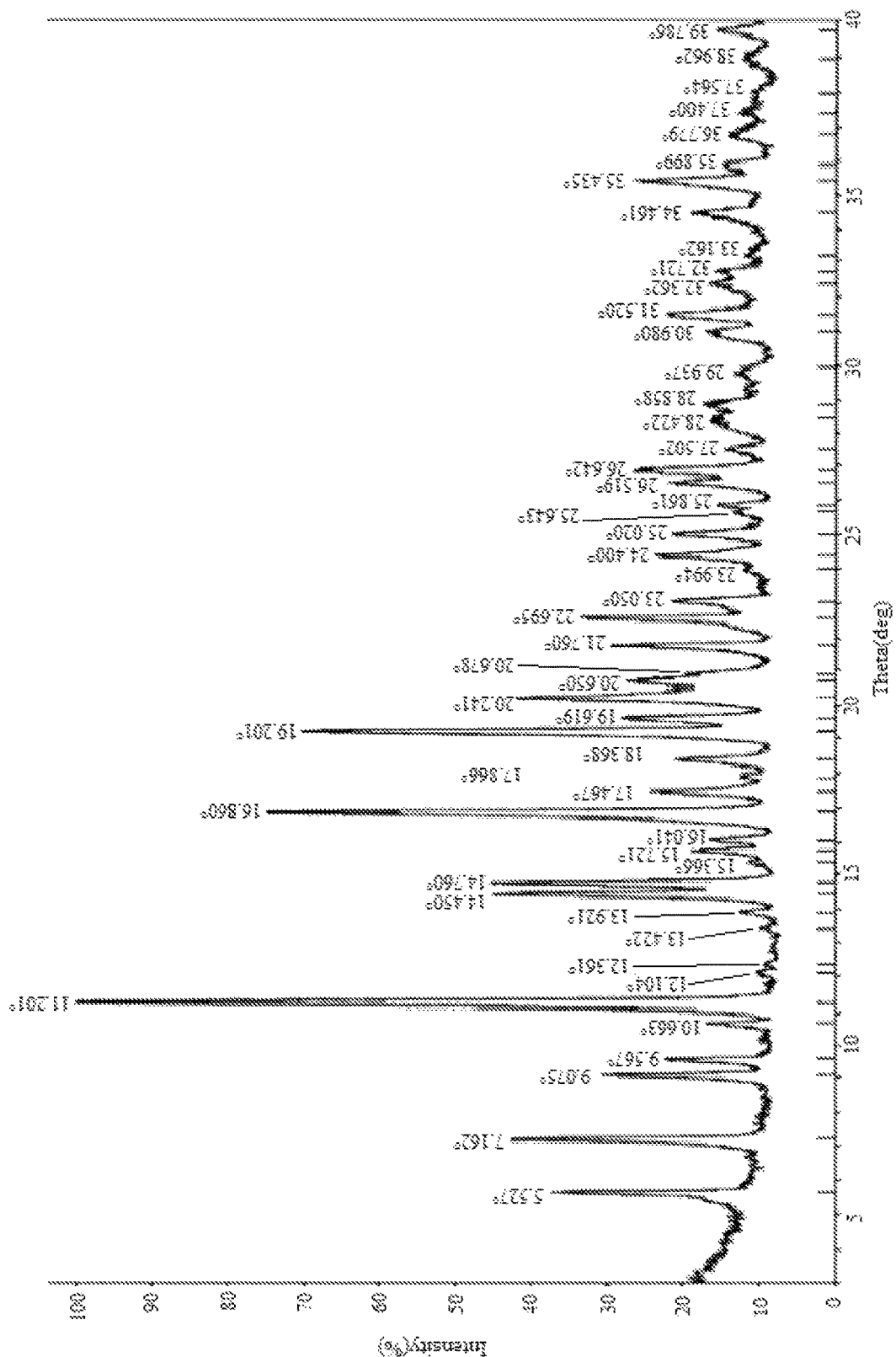
FIG. 5 is an X-ray powder diffraction spectrum of $d_9$-1-[2-dimethylamino-1-(4-methoxyphenyl)-ethyl]-cyclohexanol hydrochloride ($d_9$-venlafaxine hydrochloride, Form E) which was prepared and isolated according to the process disclosed in Example 38.
Figure 6:
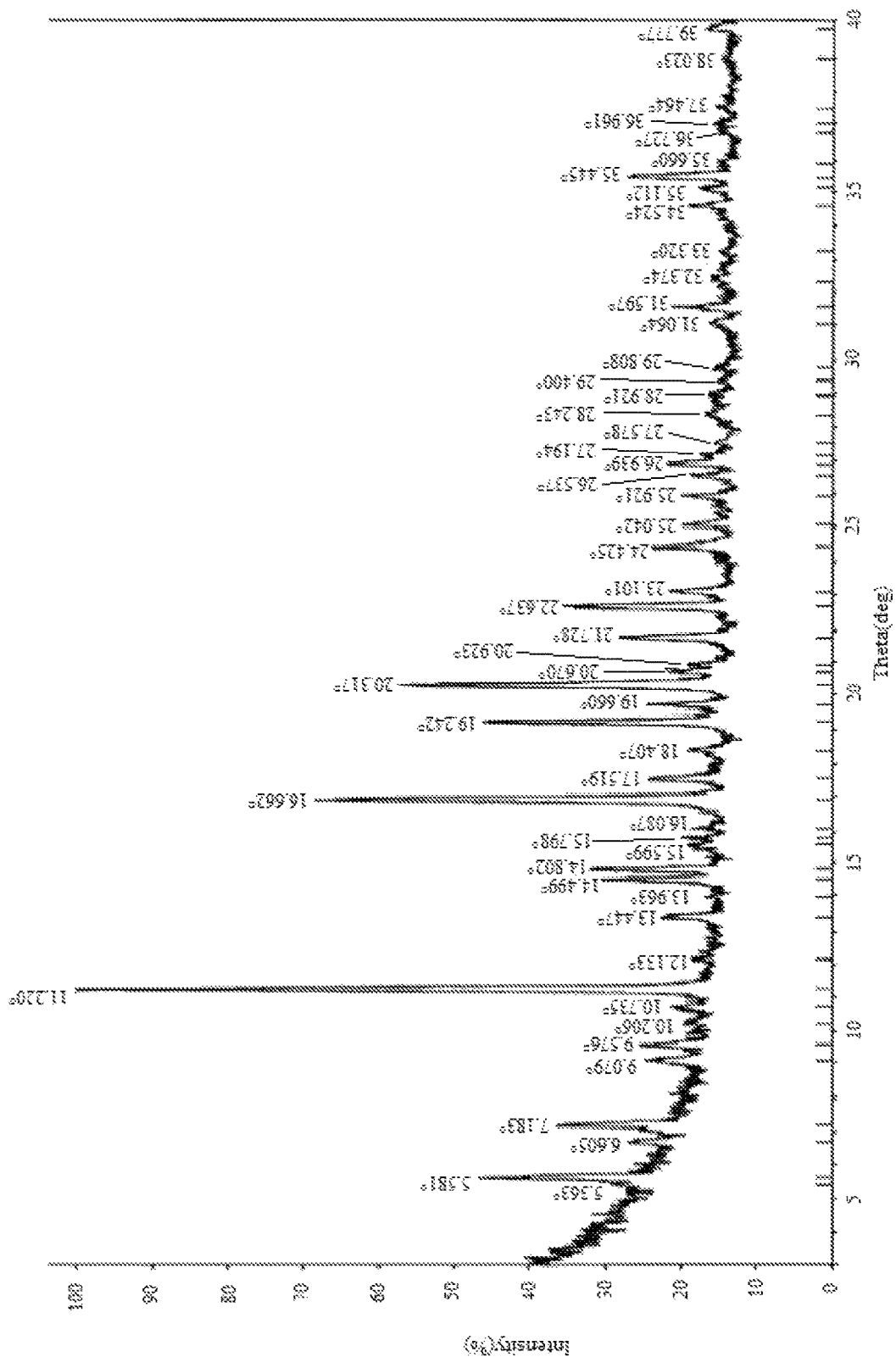
FIG. 6 is an X-ray powder diffraction spectrum of $d_9$-1-[2-dimethylamino-1-(4-methoxyphenyl)-ethyl]-cyclohexanol hydrochloride ($d_9$-venlafaxine hydrochloride, Form F) which was prepared and isolated according to the process disclosed in Example 39.

10. The Polymorph Form B of $d_9$-1-[2-dimethylamino-1-(4-methoxyphenyl)-ethyl]-cyclohexanol hydrochloride ($d_9$-venlafaxine hydrochloride) wherein said polymorph produces an X-ray powder diffraction spectrum substantially the same as shown in FIG. 2.

11. The Polymorph Form B of $d_9$-1-[2-dimethylamino-1-(4-methoxyphenyl)-ethyl]-cyclohexanol hydrochloride ($d_9$-venlafaxine hydrochloride) as recited in claim 1, wherein each position designed as D has a deuterium enrichment of no less than 5% above the naturally occurring distribution of deuterium.

12. The Polymorph Form B of $d_9$-1-[2-dimethylamino-1-(4-methoxyphenyl)-ethyl]-cyclohexanol hydrochloride ($d_9$-venlafaxine hydrochloride) as recited in claim 1, wherein each position designed as D has a deuterium enrichment of no less than 10% above the naturally occurring distribution of deuterium.

13. The Polymorph Form B of $d_9$-1-[2-dimethylamino-1-(4-methoxyphenyl)-ethyl]-cyclohexanol hydrochloride ($d_9$-venlafaxine hydrochloride) as recited in claim 1, wherein each position designed as D has a deuterium enrichment of no less than 20% above the naturally occurring distribution of deuterium.

14. The Polymorph Form B of $d_9$-1-[2-dimethylamino-1-(4-methoxyphenyl)-ethyl]-cyclohexanol hydrochloride ($d_9$-venlafaxine hydrochloride) as recited in claim 1, wherein each position designed as D has a deuterium enrichment of no less than 50% above the naturally occurring distribution of deuterium.

15. The Polymorph Form B of $d_9$-1-[2-dimethylamino-1-(4-methoxyphenyl)-ethyl]-cyclohexanol hydrochloride ($d_9$-venlafaxine hydrochloride) as recited in claim 1, wherein each position designed as D has a deuterium enrichment of no less than 70% above the naturally occurring distribution of deuterium.

16. The Polymorph Form B of $d_9$-1-[2-dimethylamino-1-(4-methoxyphenyl)-ethyl]-cyclohexanol hydrochloride ($d_9$-venlafaxine hydrochloride) as recited in claim 1, wherein each position designed as D has a deuterium enrichment of no less than 80% above the naturally occurring distribution of deuterium.

17. The Polymorph Form B of $d_9$-1-[2-dimethylamino-1-(4-methoxyphenyl)-ethyl]-cyclohexanol hydrochloride ($d_9$-venlafaxine hydrochloride) as recited in claim 1, wherein each position designed as D has a deuterium enrichment of no less than 90% above the naturally occurring distribution of deuterium.

18. The Polymorph Form B of $d_9$-1-[2-dimethylamino-1-(4-methoxyphenyl)-ethyl]-cyclohexanol hydrochloride ($d_9$-venlafaxine hydrochloride) as recited in claim 1, wherein each position designed as D has a deuterium enrichment of no less than 98% above the naturally occurring distribution of deuterium.

19. The Polymorph Form B of $d_9$-1-[2-dimethylamino-1-(4-methoxyphenyl)-ethyl]-cyclohexanol hydrochloride ($d_9$- venlafaxine hydrochloride) of claim 1, which further produces a solid state infrared spectrum comprising peaks at about 3319 and 2917 cm$^{-1}$.

20. The Polymorph Form B of $d_9$-1-[2-dimethylamino-1-(4-methoxyphenyl)-ethyl]-cyclohexanol hydrochloride ($d_9$-venlafaxine hydrochloride) of claim 1, wherein:

each position designed as D has a deuterium enrichment of no less than 90% above the naturally occurring distribution of deuterium; and said polymorph produces:

(i) an X-ray powder diffraction spectrum comprising at least four peaks at diffraction angles (2θ) of 6.683, 10.201, 13.441, 15.014, 15.517, 16.84, 17.206, 18.198, 19.179, 20.258, 21.68, 22.668, 23.923, 25.322, 25.543, 26.502, 27.122, 27.567, 28.022, 28.64, 29.241, 29.650, 31.079, 31.379, 31.978, 32.260, 32.701, 32.961, 34.12, 35.02, 36.024, 36.842, 37.5, or 38.341 2θ; and (ii) a solid state infrared spectrum comprising peaks at about 3319 and 2917 cm$^{-1}$.

* * * * *